US009357755B2

(12) United States Patent
Fraser et al.

(10) Patent No.: US 9,357,755 B2
(45) Date of Patent: Jun. 7, 2016

(54) PRODUCTION OF HUMAN GLYCOSYLATED PROTEINS IN SILK WORM

(75) Inventors: Malcolm J. Fraser, Granger, IN (US); Donald L. Jarvis, Laramie, WY (US)

(73) Assignees: The University of Wyoming, Laramie, WY (US); University of Notre Dame, Notre Dame, IN (US)

( * ) Notice: Subject to any disclaimer, the term of this patent is extended or adjusted under 35 U.S.C. 154(b) by 400 days.

(21) Appl. No.: 12/627,697

(22) Filed: Nov. 30, 2009

(65) Prior Publication Data

US 2010/0186099 A1 Jul. 22, 2010

Related U.S. Application Data

(63) Continuation-in-part of application No. 10/577,528, filed as application No. PCT/US2004/035553 on Oct. 28, 2004, now abandoned.

(60) Provisional application No. 60/514,741, filed on Oct. 28, 2003.

(51) Int. Cl.
*A01K 67/04* (2006.01)
*A01K 67/033* (2006.01)
*C12N 15/85* (2006.01)

(52) U.S. Cl.
CPC ........ *A01K 67/0333* (2013.01); *C12N 15/8509* (2013.01); *A01K 2227/70* (2013.01); *A01K 2267/01* (2013.01)

(58) Field of Classification Search
CPC .............. A01K 67/0333; A01K 67/04; A01K 2227/70; A01K 2267/01; C12N 15/8509
USPC .......................................................... 800/13
See application file for complete search history.

(56) References Cited

U.S. PATENT DOCUMENTS

| 6,090,584 A * | 7/2000 | Iatrou et al. ................. 435/69.1 |
| 6,153,409 A | 11/2000 | Bentley et al. |
| 2002/0116723 A1 | 8/2002 | Grigliatti et al. |
| 2002/0137134 A1 | 9/2002 | Gerngross et al. |

FOREIGN PATENT DOCUMENTS

| WO | 98/06835 | 2/1998 |
| WO | 01/42492 | 6/2001 |

OTHER PUBLICATIONS

Rancourt et al, Mol. Cell Biol. 7(6):2188-2195, 1987; abstract only.*
Johansen et al, Genes Dev. 3(6):882-889, 1989; abstract only.*
Raeber et al, Mech. Dev. 51(2-3):317-327, 1995; abstract only.*
Reis et al, Biotechnology 10(8):910-912, 1992; abstract only.*
Nikolaev et al, Mol. Gen. Genet. 236(2-3):326-30, 1993; abstract only.*
Sun et al, Genes and Development 2(6):743-753, 1988; abstract only.*
Toshiki et al, Nature Biotechnology 18:81-84, 2000.*
Nony et al, Biol. Cell 84(1-2):43-52, 1995.*
Lobo, N., et al. "Transposition of the piggyBac element in embryos of *Drosophila melanogaster, Aedes aegypti* and *Trichoplusia ni.*" Mol Gen Genet. Jun. 1999;261(4-5):803-10.
Fabini, G., et al. "Identification of core alpha 1,3-fucosylated glycans and cloning of the requisite fucosyltransferase cDNA from *Drosophila melanogaster*. Potential basis of the neural anti-horseadish peroxidase epitope." J Biol Chem. Jul. 27, 2001;276(30):28058-67. Epub May 29, 2001.
Hammond, S.M., et al. "Post-transcriptional gene silencing by double-stranded RNA." Nat Rev Genet. Feb. 2001;2 (2):110-9.
Kaiser, M., et al. "P-element inserts in transgenic flies: a cautionary tale." Heredity. Jan. 1997;78(Pt 1):1-11.
Clark, A.G., et al. "Spontaneous mutation rate of modifiers of metabolism in *Drosophila*." Genetics. Feb. 1995;139 (2):767-79.
Henikoff, S. "Conspiracy of silence among repeated transgenes." Bioessays. Jul. 1998;20(7):532-5.
Adelman, Z.N., et al. "Formation and loss of large, unstable tandem arrays of the piggyBac transposable element in the yellow fever mosquito, *Aedes aegypti*." Transgenic Res. Oct. 2004;13(5):411-25.
Kennerdell, J.R., et al. "Heritable gene silencing in *Drosophila* using double-stranded RNA." Nat Biotechnol. Aug. 2000;18(8):896-8.
Stein, C.A. "The experimental use of antisense oligonucleotides: a guide for the perplexed." J Clin Invest. Sep. 2001;108(5):641-4.
Tomiya, N., et al. "Humanization of lepidopteran insect-cell-produced glycoproteins." Acc Chem Res. Aug. 2003;36 (8):613-20.
Aumiller, J.J., et al. "A transgenic insect cell line engineered to produce CMP-sialic acid and sialylated glycoproteins." Glycobiology. Jun. 2003;13(6):497-507. Epub Feb. 20, 2003.
Hollister, J., et al. "Engineering the protein N-glycosylation pathway in insect cells for production of biantennary, complex N-glycans." Biochemistry. Dec. 17, 2002;41(50):15093-104.
Jarvis, D.L. "Developing baculovirus-insect cell expression systems for humanized recombinant glycoprotein production." Virology. May 25, 2003;310(1):1-7.
Breitbach, K., et al. "Improved glycosylation of a foreign protein by Tn-5B1-4 cells engineered to express mammalian glycosyltransferases." Biotechnol Bioeng. Aug. 5, 2001;74(3):230-9.
Hollister, J., et al. "Evidence for a sialic acid salvaging pathway in lepidopteran insect cells." Glycobiology. Jun. 2003;13(6):487-95. Epub Feb. 20, 2003.
Aumiller, J.J., et al. "Expression and functional characterization of a nucleotide sugar transporter from *Drosophila melanogaster*: relevance to protein glycosylation in insect cell expression systems." Protein Expr Purif. Dec. 2002;26 (3):438-48.
Abdul-Rahman, B., et al. "Beta-(1 → 4)-galactosyltransferase activity in native and engineered insect cells measured with time-resolved europium fluorescence." Carbohydr Res. Nov. 19, 2002;337(21-23):2181-6.
Vadaie, N., et al. "Identification and characterization of a *Drosophila melanogaster* ortholog of human beta1,4-galactosyltransferase VII." Glycobiology. Oct. 2002;12(10):589-97.
Jarvis, D.L., et al. "Novel baculovirus expression vectors that provide sialylation of recombinant glycoproteins in lepidopteran insect cells." J Virol. Jul. 2001;75(13):6223-7.

(Continued)

*Primary Examiner* — Kevin Hill
(74) *Attorney, Agent, or Firm* — Kathleen D. Rigaut; Patrick J. Hagan; Dann, Dorfman, Herrell and Skillman, P.C.

(57) ABSTRACT

A transgenic silkworm system for recombinant glycoprotein production is provided.

6 Claims, 22 Drawing Sheets

(56) References Cited

OTHER PUBLICATIONS

Seo, N.S., et al. "Mammalian glycosyltransferase expression allows sialoglycoprotein production by baculovirus-infected insect cells." Protein Expr Purif. Jul. 2001;22(2):234-41.

Kawar, Z., et al. "Insect cells encode a class II alpha-mannosidase with unique properties." J Biol Chem. May 11, 2001;276(19):16335-40. Epub Feb. 9, 2001.

Kawar, Z., et al. "Biosynthesis and subcellular localization of a lepidopteran insect alpha 1,2-mannosidase." Insect Biochem Mol Biol. Mar. 15, 2001;31(4-5):289-97.

Marchal, I., et al. "Glycoproteins from insect cells: sialylated or not?" Biol Chem. Feb. 2001;382(2):151-9.

Hollister, J.R., et al. "Engineering lepidopteran insect cells for sialoglycoprotein production by genetic transformation with mammalian beta 1,4-galactosyltransferase and alpha 2,6-sialyltransferase genes." Glycobiology. Jan. 2001;11(1):1-9.

Ailor, E., et al. "N-glycan patterns of human transferrin produced in Trichoplusia ni insect cells: effects of mammalian galactosyltransferase." Glycobiology. Aug. 2000;10(8):837-47.

Kawar, Z., et al. "N-Glycan processing by a lepidopteran insect alpha1,2-mannosidase." Glycobiology. Apr. 2000;10 (4):347-55.

Wolff, M.W., et al. "Electrophoretic analysis of glycoprotein glycans produced by lepidopteran insect cells infected with an immediate early recombinant baculovirus encoding mammalian beta1,4-galactosyltransferase." Glycoconj J. Dec. 1999;16(12):753-6.

Jarvis, D.L., et al. "Engineering N-glycosylation pathways in the baculovirus-insect cell system." Curr Opin Biotechnol. Oct. 1998;9(5):528-33.

Hollister, J.R., et al. "Stable expression of mammalian beta 1,4-galactosyltransferase extends the N-glycosylation pathway in insect cells." Glycobiology. May 1998;8(5):473-80.

Kawar, Z., et al. "Isolation and characterization of an alpha 1,2-mannosidase cDNA from the lepidopteran insect cell line Sf9." Glycobiology. Apr. 1997;7(3):433-43.

Jarvis, D.L., et al. "Modifying the insect cell N-glycosylation pathway with immediate early baculovirus expression vectors." Nat Biotechnol. Oct. 1996;14(10):1288-92.

Jarvis, D.L., et al. "Immediate-early baculovirus vectors for foreign gene expression in transformed or infected insect cells." Protein Expr Purif. Sep. 1996;8(2):191-203.

Jarvis, D.L., et al. "Biochemical analysis of the N-glycosylation pathway in baculovirus-infected lepidopteran insect cells." Virology. Oct. 1, 1995;212(2):500-11.

Wu, S.C., et al. "Heterologous protein expression affects the death kinetics of baculovirus-infected insect cell cultures: a quantitative study by use of n-target theory." Biotechnol Prog. Jan.-Feb. 1994;10(1):55-9.

Jarvis, D.L. "Effects of baculovirus infection on IE1-mediated foreign gene expression in stably transformed insect cells." J Virol. May 1993;67(5):2583-91.

Licari, P.J., et al. "Insect cell hosts for baculovirus expression vectors contain endogenous exoglycosidase activity." Biotechnol Prog. Mar.-Apr. 1993;9(2):146-52.

Jarvis, D.L. "Foreign gene expression in insect cells." Bioprocess Technol. 1993;17:195-219.

Jarvis, D.L., et al. "Role of glycosylation in the transport of recombinant glycoproteins through the secretory pathway of lepidopteran insect cells." J Cell Biochem. Apr. 1990;42(4):181-91.

Jarvis, D.L., et al. "Glycosylation and secretion of human tissue plasminogen activator in recombinant baculovirus-infected insect cells." Mol Cell Biol. Jan. 1989;9(1):214-23.

\* cited by examiner pDIE1-GnTII/GalT-DsRed1-TOPO.4
8930 bp pDIE1-ST6.1/ST3.4-ECFP-TOPO.4
8630 bp

A

B

SEQUENCE LISTING

```
<160> NUMBER OF SEQ ID NOS: 3

<210> SEQ ID NO 1
<211> LENGTH: 218
<212> TYPE: DNA
<213> ORGANISM: Trichoplusia ni

<400> SEQUENCE: 1
gtggcgtggt ttgtttggaa ctgccacgcc cgcaaccgcc gcctgcagta cgcgcggcag      60
ctcagcaggc acatccaggt ggacatctac ggtgcgtgcg gctcgcacca ctgcccccgc     120
```

```
actgacccca actgcctgga gatgctcgac agggactaca agttctacct cgcatttgaa    180
aattctaact gtcgtgatta catcacagag aagttctt                            218
```

<210> SEQ ID NO 2
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 2

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 3
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 3

```
Asn Phe Asp Leu Leu Lys Leu Ala Gly Asp Val Glu Ser Asn Pro Gly
1               5                   10                  15
```

US 9,357,755 B2

PRODUCTION OF HUMAN GLYCOSYLATED PROTEINS IN SILK WORM

CROSS REFERENCE TO RELATED APPLICATIONS

This application is a continuation-in-part of U.S. patent application Ser. No. 10/577,528 filed Apr. 28, 2006 which is a §371 application of PCT/US2004/035553, filed Oct. 28, 2004, which claims priority to U.S. Provisional Application 60/514,741 filed Oct. 28, 2003.

FIELD OF THE INVENTION

This invention relates to complex N-glycosylation of therapeutically and commercially valuable proteins in the silk worm. More specifically, the invention provides methods, vectors, and transgenic silkworms for the production thereof.

BACKGROUND OF THE INVENTION

Several publications and patent documents are cited throughout the specification in order to describe the state of the art to which this invention pertains. Each of these citations is incorporated herein by reference as though set forth in full.

The biotechnology revolution has created vast new potential for pharmaceuticals, yet this potential remains unrealized due largely to problems in manufacturing. Biopharmaceuticals, which have greatly expanded targets for therapeutic intervention, now represent about 30% of the drugs in the development pipeline. However, the biopharmaceutical industry does not have the manufacturing infrastructure required to meet patient needs. In other words, discovery has far outpaced production. Drug development is associated with a variety of hurdles, including cycle-process changes, scale-up problems, and capacity shortages, all of which give rise to the need to repeat clinical trials thereby exhausting developers' money often before drugs can be approved for use.

Methods have been developed for producing biopharmaceuticals, particularly recombinant proteins such as enzymes and antibodies, in a variety of hosts, including bacteria, yeast, mammalian cell culture, and transgenic mammals and plants. However, each of these systems suffers from shortcomings. For example, proteins produced by bacterial fermentation fail to include biochemically important mammalian modifications. Mammalian cell culture cannot easily be scaled up to produce enough protein of commercial value and transgenic mammals are expensive and time consuming to produce and raise problems of public acceptance.

To be fully functional, most proteins require "post-translational modification" or further changes to overall structure and composition. The most common change involves a process called glycosylation, an enzyme-mediated addition of specific sugars to the protein backbone. Glycosylation is important for protein use in humans, as it can affect the efficacy, stability and often safety of a potential drug. The best known biotherapeutics are treatments for diabetes, Multiple sclerosis, Hodgkin's lymphoma, Crohn's disease, and various promising therapies for AIDS and cancer. Seven of the current top ten biopharmaceuticals (Procrit, Epogen, Intron A/Rebetron, Neupogen, Humulin, Avonex, Rituxan, Enbrel, Remicade, and Cerezyme) require glycosylation.

It would be desirable to produce recombinant proteins that have proper mammalian (e.g., human) glycosylation patterns, in insect cells. Such a process could provide the industry a flexible, low-capital-intensive, fast-turnaround, linearly scalable process for manufacturing authentic human-type glycoproteins for therapeutic applications.

SUMMARY OF THE INVENTION

In accordance with the present invention, a transgenic silk worm comprising a plurality of nucleic acids encoding mammalian glycosylation enzymes and optionally a nucleic acid encoding a heterologous protein of interest is provided wherein the glycosylation enzymes are selected from the group consisting of at least one beta-1,2-N-acetylglucosaminyltransferase, a β1,4-galactosyltransferase, one or more sialyltransferases, a sialic acid synthase, and CMP sialic acid synthetase, wherein each recombinant nucleic acid encoding a glycosylation enzyme is integrated in the insect genome, and is present in one or more copies, wherein each recombinant nucleic acid encoding a glycosylation enzyme is operably linked to an expression control sequence, and wherein expression of said glycosylation enzymes allows for production of a partially or completely mammalianized glycosylated protein in the insect. The transgenic silk worm of the invention may also comprise recombinant nucleic acid encoding one or more of the following auxiliary glycosylation proteins: UDP-N-acetylglucosamine 2 epimerase/N-acetylmannosamine kinase; beta-1,4-N-acetylglucosaminyltransferase III; beta-1,4-N-acetylglucosaminyltransferase IV, beta-1,6-N-acetylglucosaminyltransferase V, beta-1,4-N-acetylglucosaminyltransferase VI, beta 1,4-N-acetylgalactosaminyltransferase, CMP-sialic acid transporter, UDP-galactose transporter, wherein each recombinant nucleic acid encoding an auxiliary glycosylation protein is genomically integrated in the insect genome and is present in one or more copies, and wherein each recombinant nucleic acid is operably linked to an expression control sequence. In one embodiment, the expression or activity of endogenous alpha 1,3-fucosyltransferase is inhibited.

In a preferred embodiment of the invention, the transgenic silk worm comprises Gn-TII/β4GalT, ST6GalI/ST3GalIII, SAS/CMP-SAS and a nucleic acid encoding a heterologous protein of interest. Heterologous glycosylated proteins produced by the transgenic silk worm also comprise an aspect of the invention.

In yet another embodiment, a method for producing a partially or completely mammalianized glycoslyated protein of interest, comprising cultivating the silk worm of the invention under conditions effective to produce the mammalianized glycosylated protein is provided. The method optionally entails isolation and/or purification of the glycosylated protein. DNA constructs encoding the glycosylating enzymes useful in the practice of the aforementioned methods are also encompassed by the present invention.

Figure 1A:
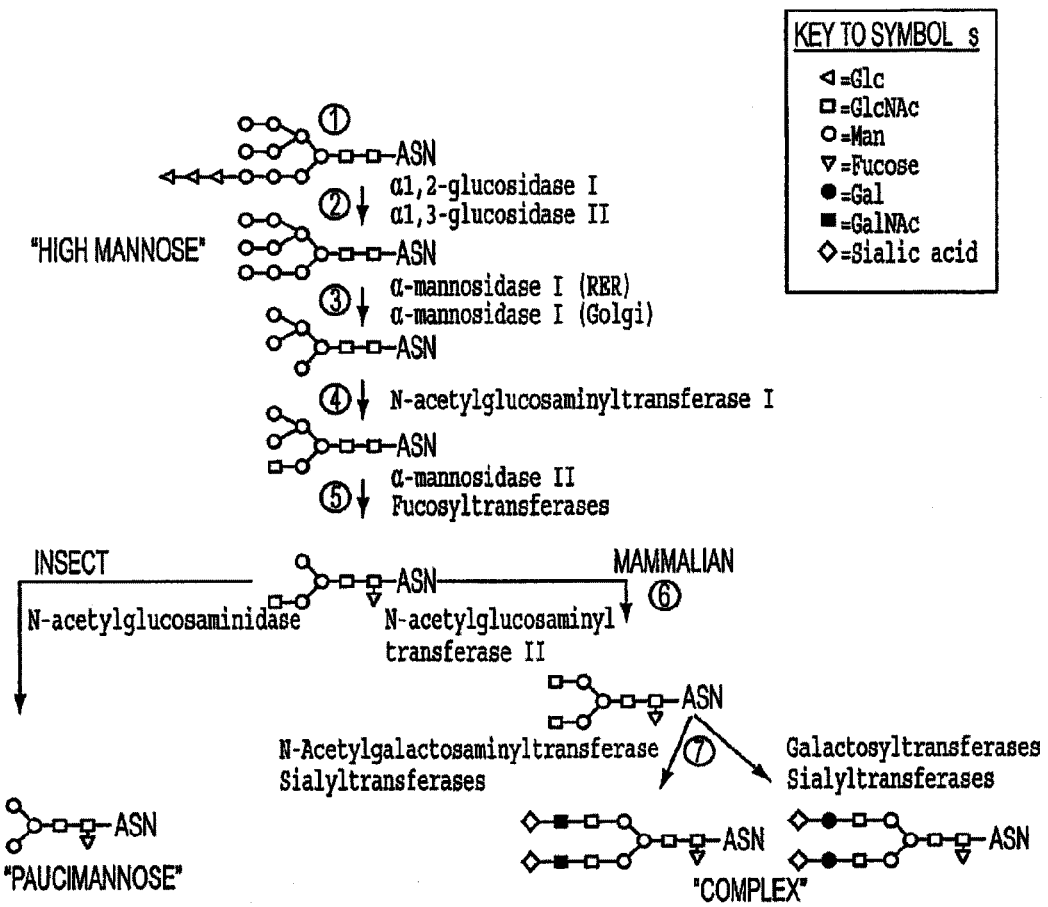
FIG. 1A shows protein N-glycosylation pathways. (Jarvis et al. (1998) Current Opinion in Biotechnology 2, 528-533 and Jarvis, D. L. (2003) Virology 310, 1-7.)

| Promoter sizes: | piggyBac size: |
|---|---|
| (2X) iel promoter 2.4 Kb, hr 5 fragment 0.5 Kbp, total 2.9 Kb<br>(2X) hsp70 0.94 Kb, hr 5 fragment 0.5 Kb, total 1.44 Kb<br>(2X) CMV 0.13 Kb, (7X) TetO 0.3 Kb, total | 5'TR 0.1 Kb, 3'TR 0.3 Kb, total 0.4 Kb |

| Enzyme pair size: | GFP marker gene size: |
|---|---|
| 2.6 Kb human GlcNAc-TI, 1.34 Kb human GlcNAc-TII, total 3.94 Kb | 3XP3/GFP gene 1.29 Kb |
| 1.65 Kb rat alpha 2,6-sialyltransferase, 1.00 Kb mouse alpha 2,3-sialyltransferase, total 2.6 Kb | |
| 1.3 Kb mouse SAS, 1.7 Kb mouse CMP-SAS, total 3 Kb | |

Figure 4A:
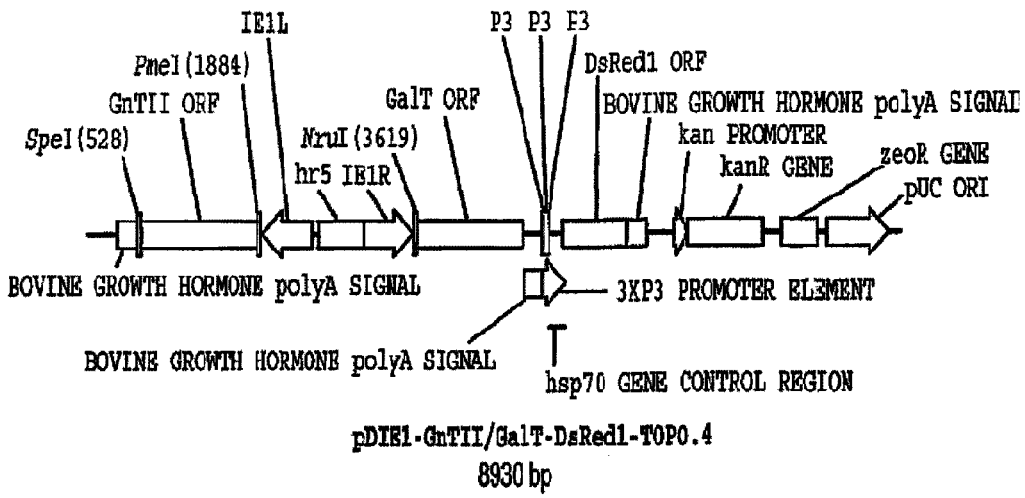
Figure 4B:
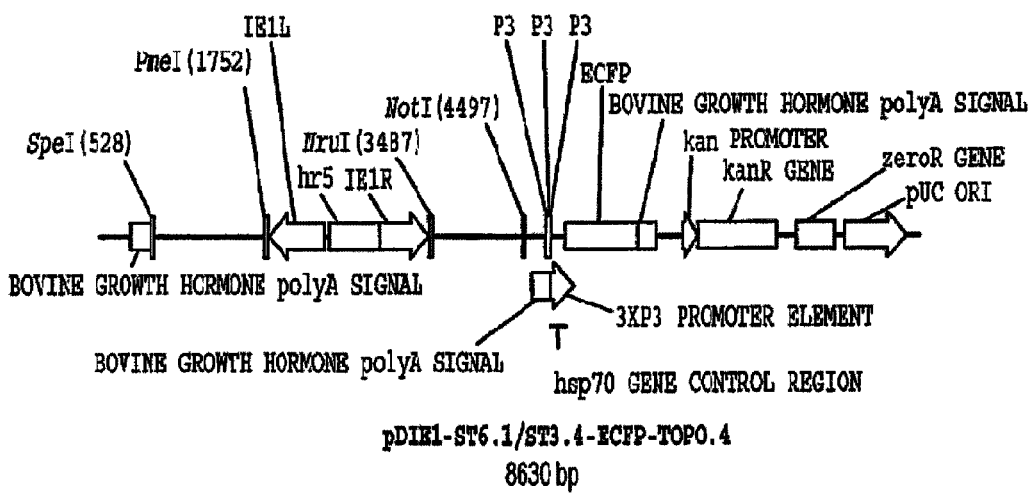
Figure 4C:
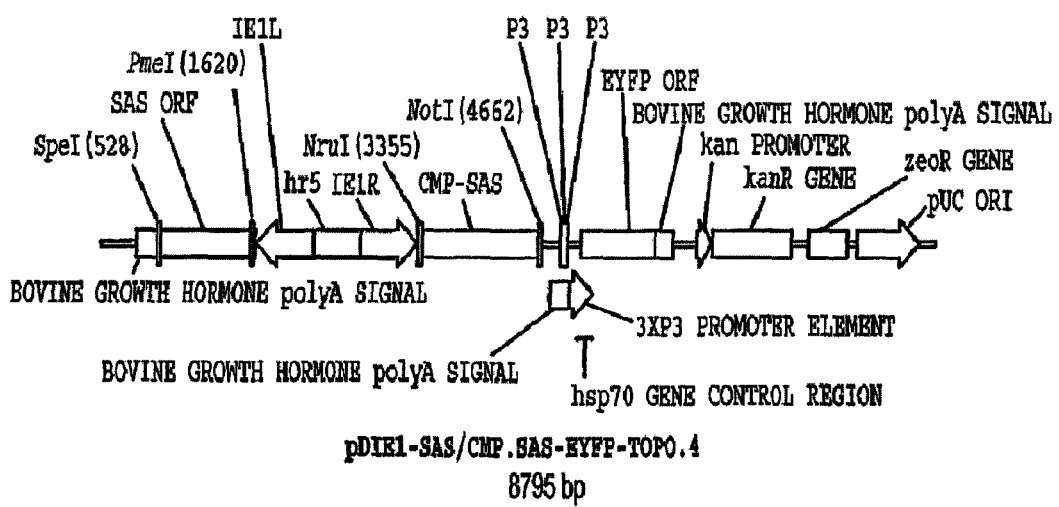

Largest size for an individual piggyBac transposon construct will be 8.13K6, well within the limits of demonstrated mobility FIG. 4 shows three constructs. FIG. 4A shows pDIE1-GnTII/GalT-DsRed1-TOPO. 4; FIG. 4B shows pDIE1-ST6.1/ST3. 4-ECFP-TOPO. 4; FIG. 4C shows pDIE-SAS/CMP. SAS-EYFP-TOPO. 4. Abbreviations: DIE1, dual immediate early 1; GnTII, N-acetylglucosaminyltransferase II; GalT, β4-galactosyltransferase, ST6.1, alpha 2,6-sialyltransferase; ST3.4, alpha 2,3-sialyltransferase; ECFP, enhanced cyano fluorescent protein; SAS, sialic acid synthase; CMP. SAS, CMP-sialic acid synthetase; EYFP, enhanced yellow fluorescent protein.

Figure 5:
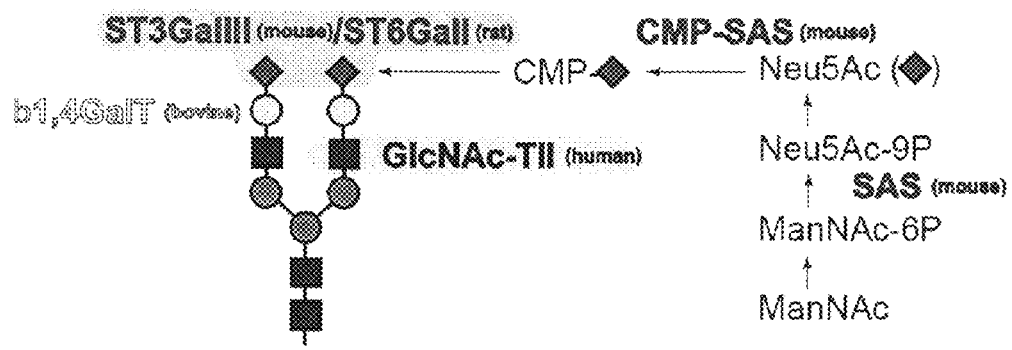

FIG. 5 shows complex N-linked glycans produced in *Drosophila*.

Figure 6:
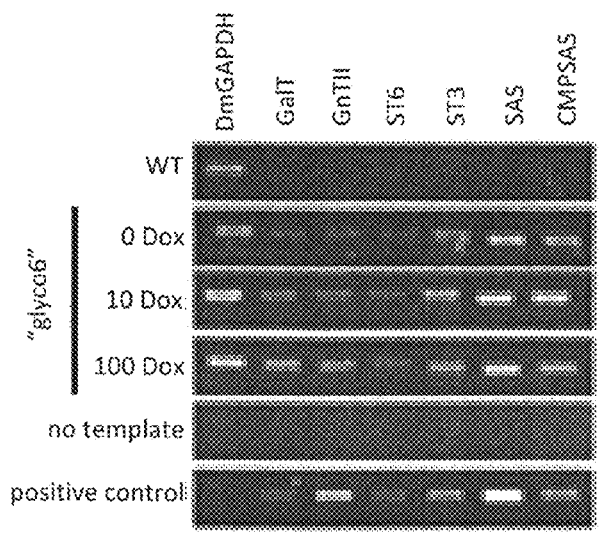
Figure 6:
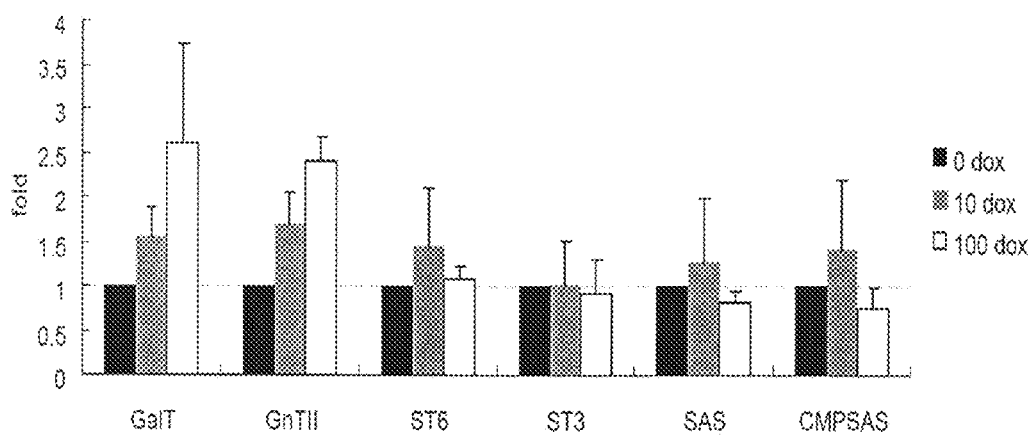
Figure 7A:
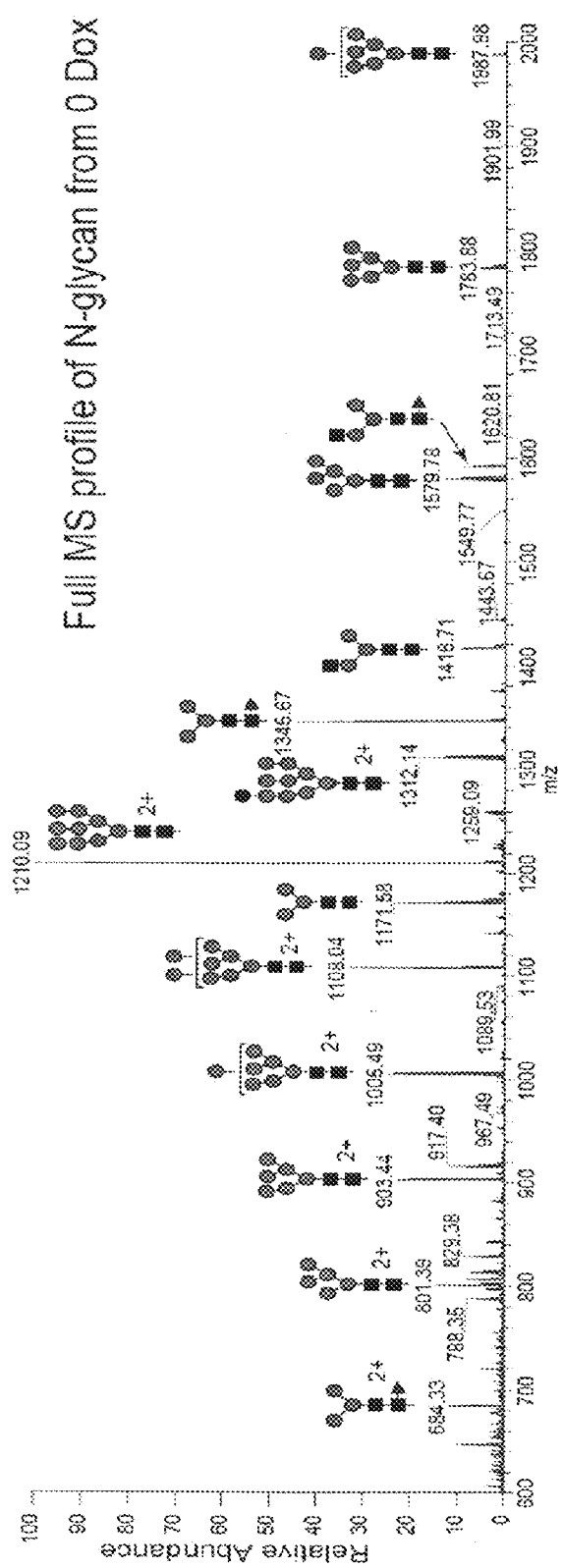
Figure 7B:
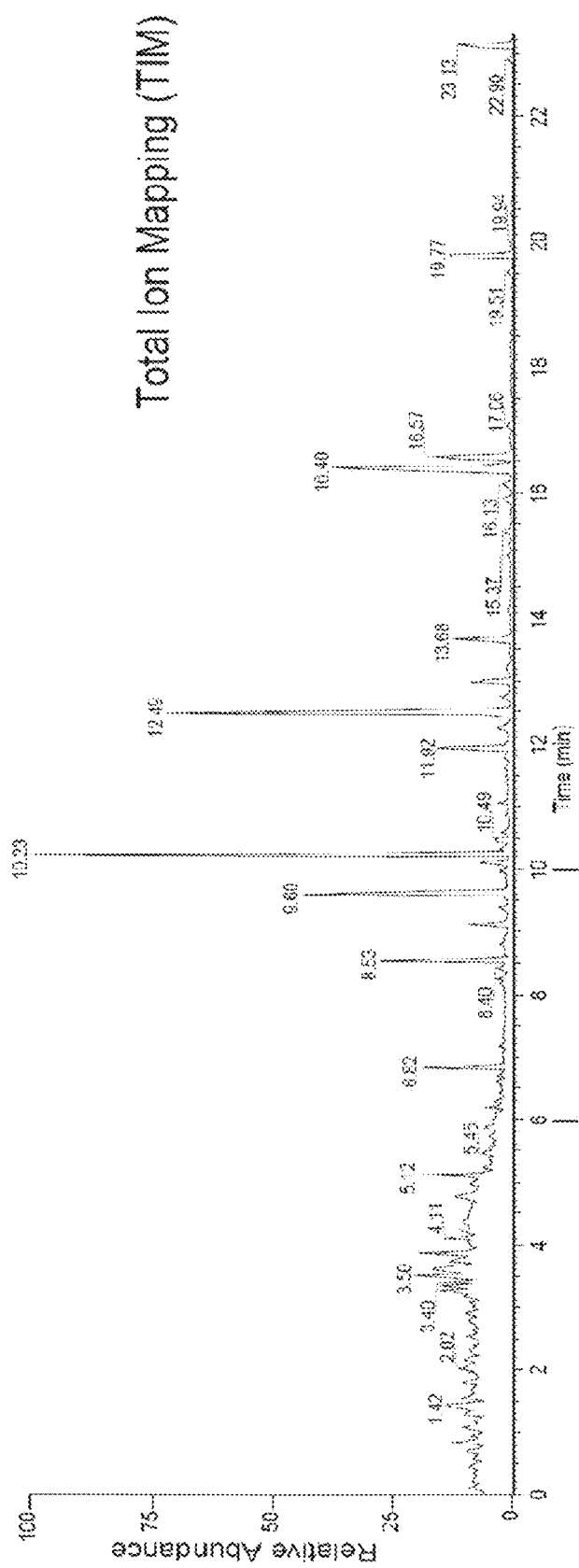
Figure 7C:
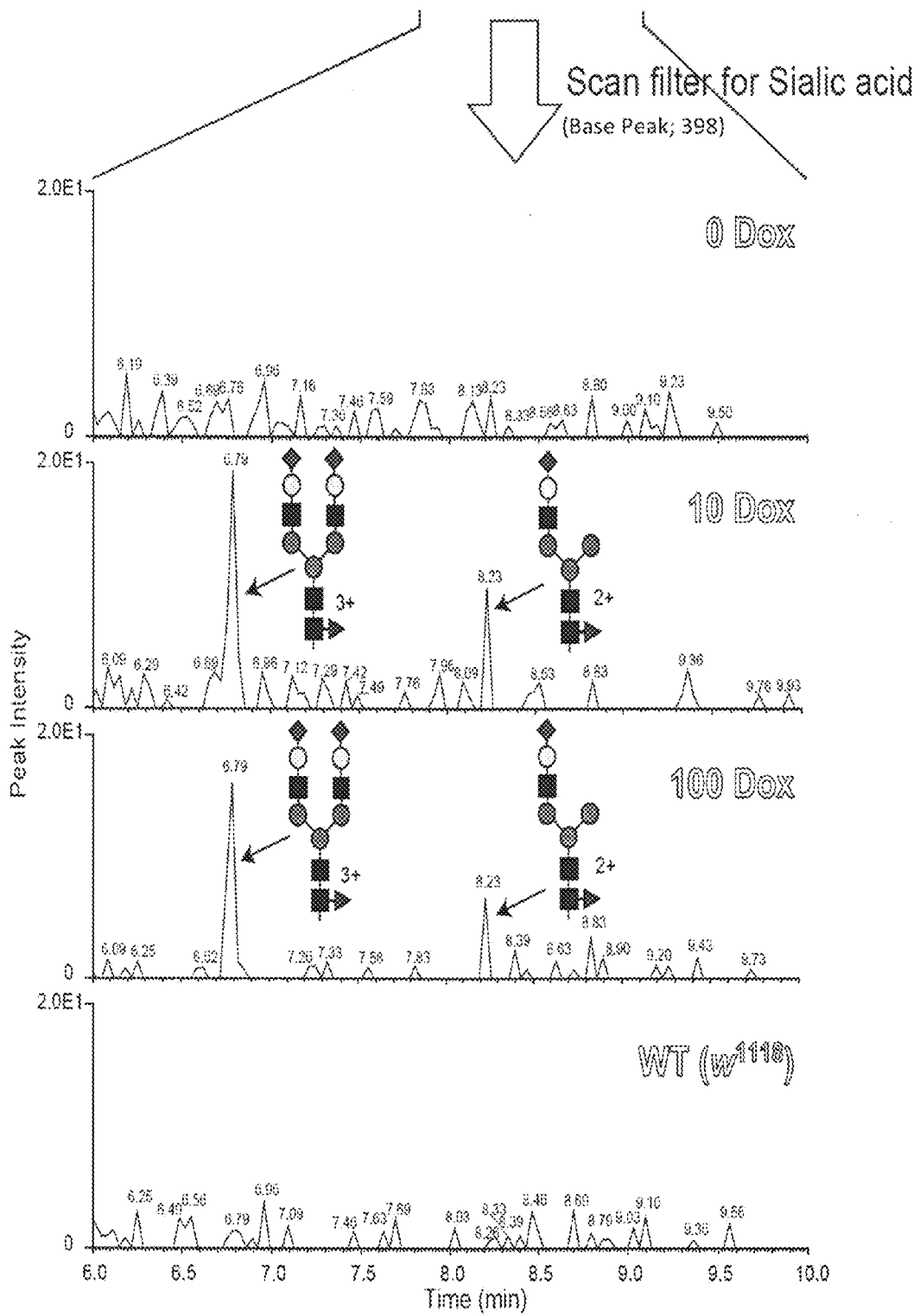
Figure 7D:
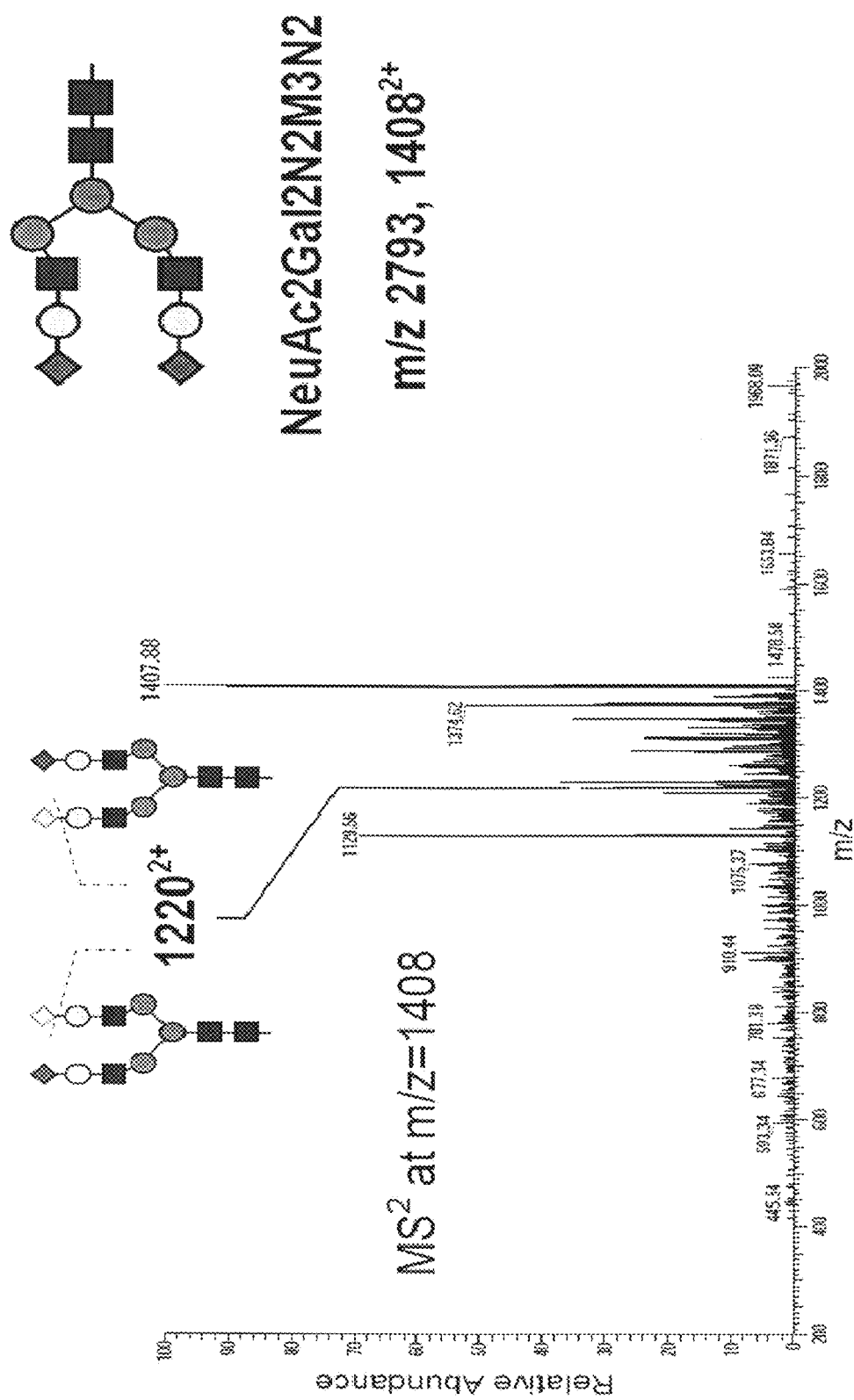
Figure 7E:
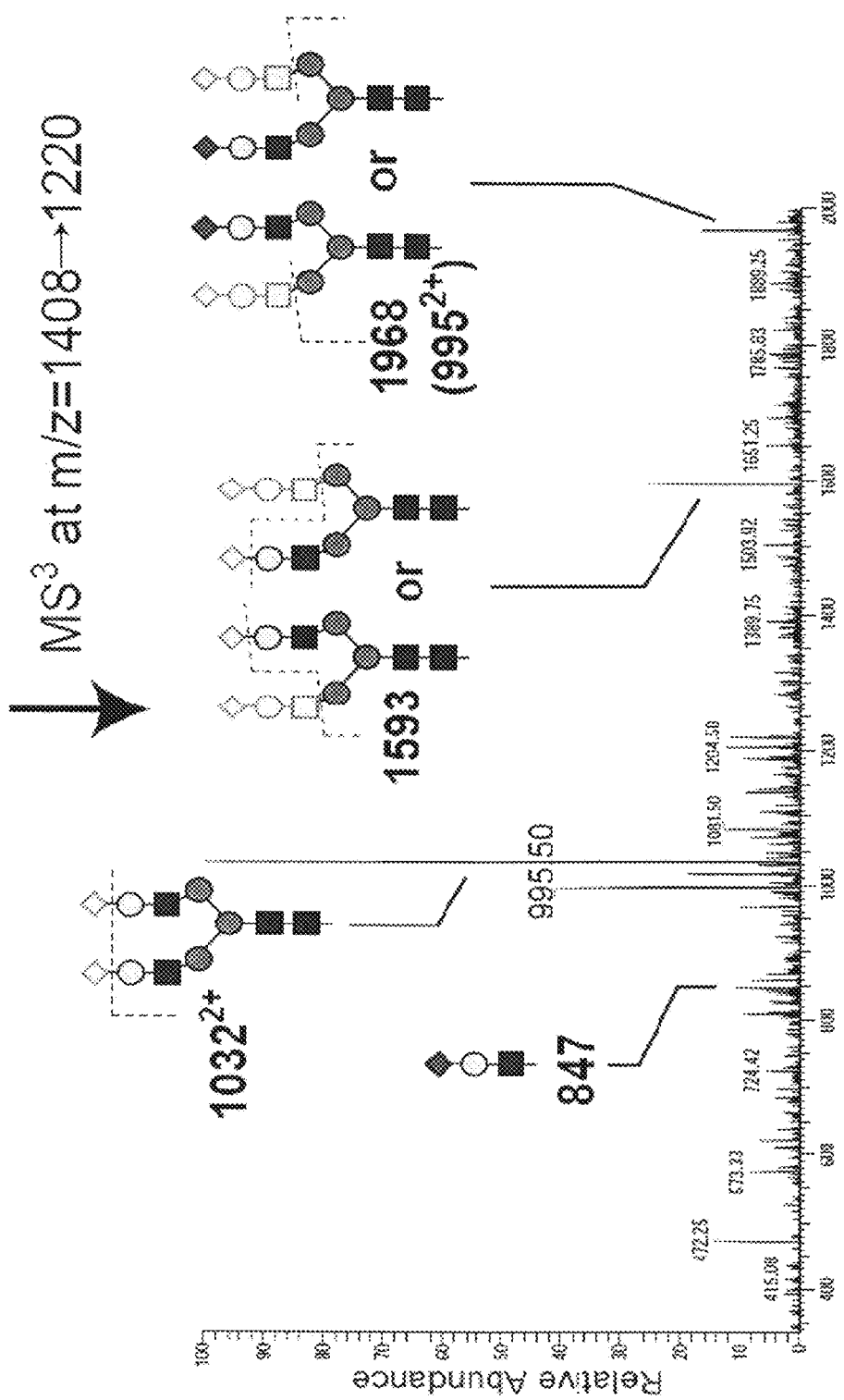
Figure 8A:
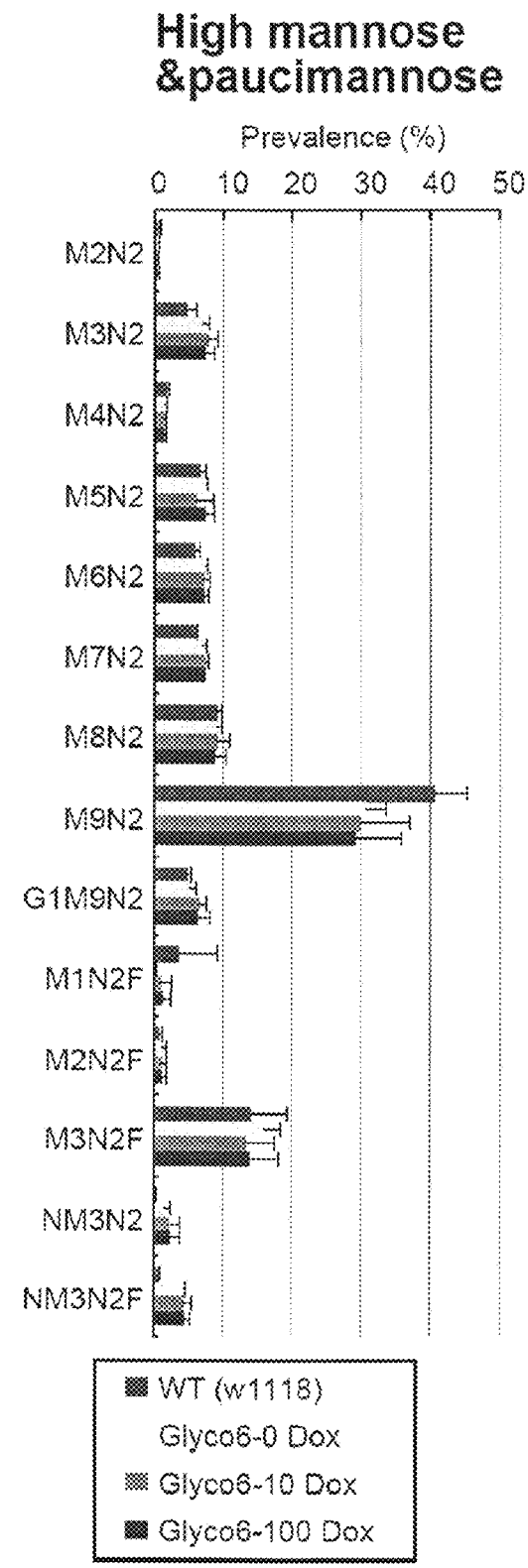
Figure 8B:
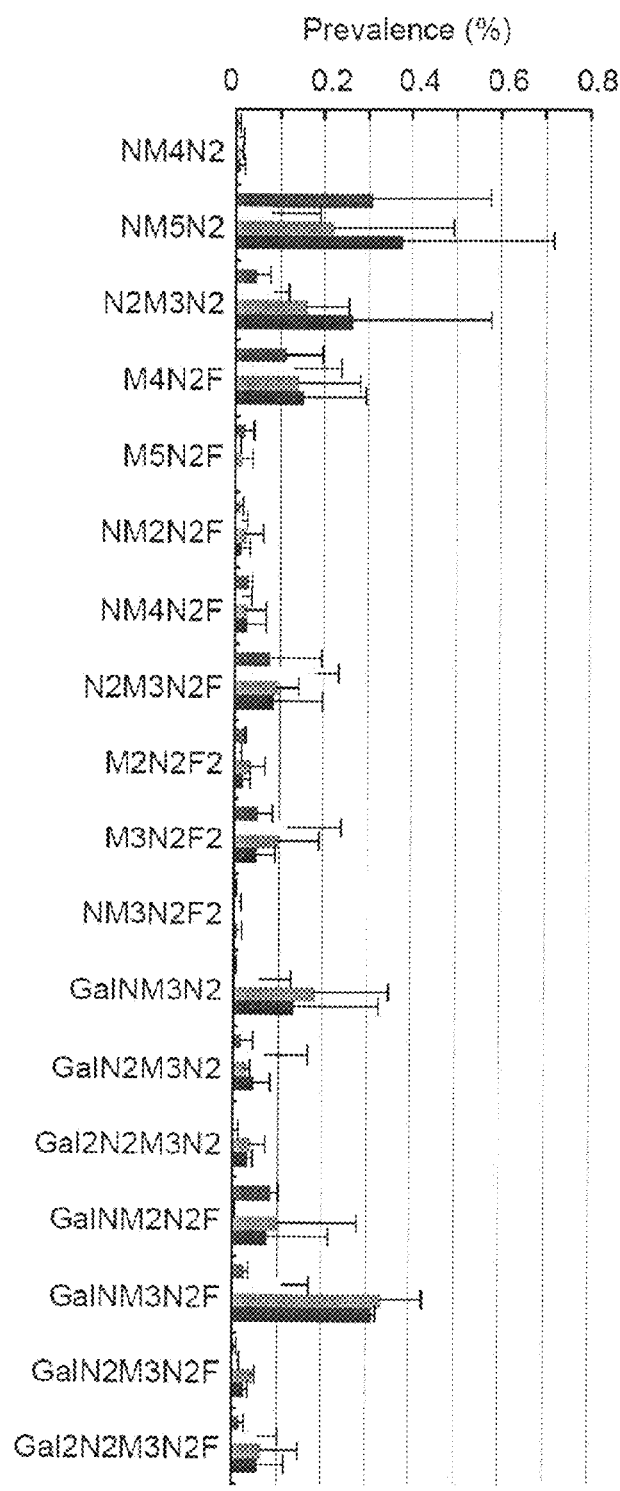
Figure 8C:
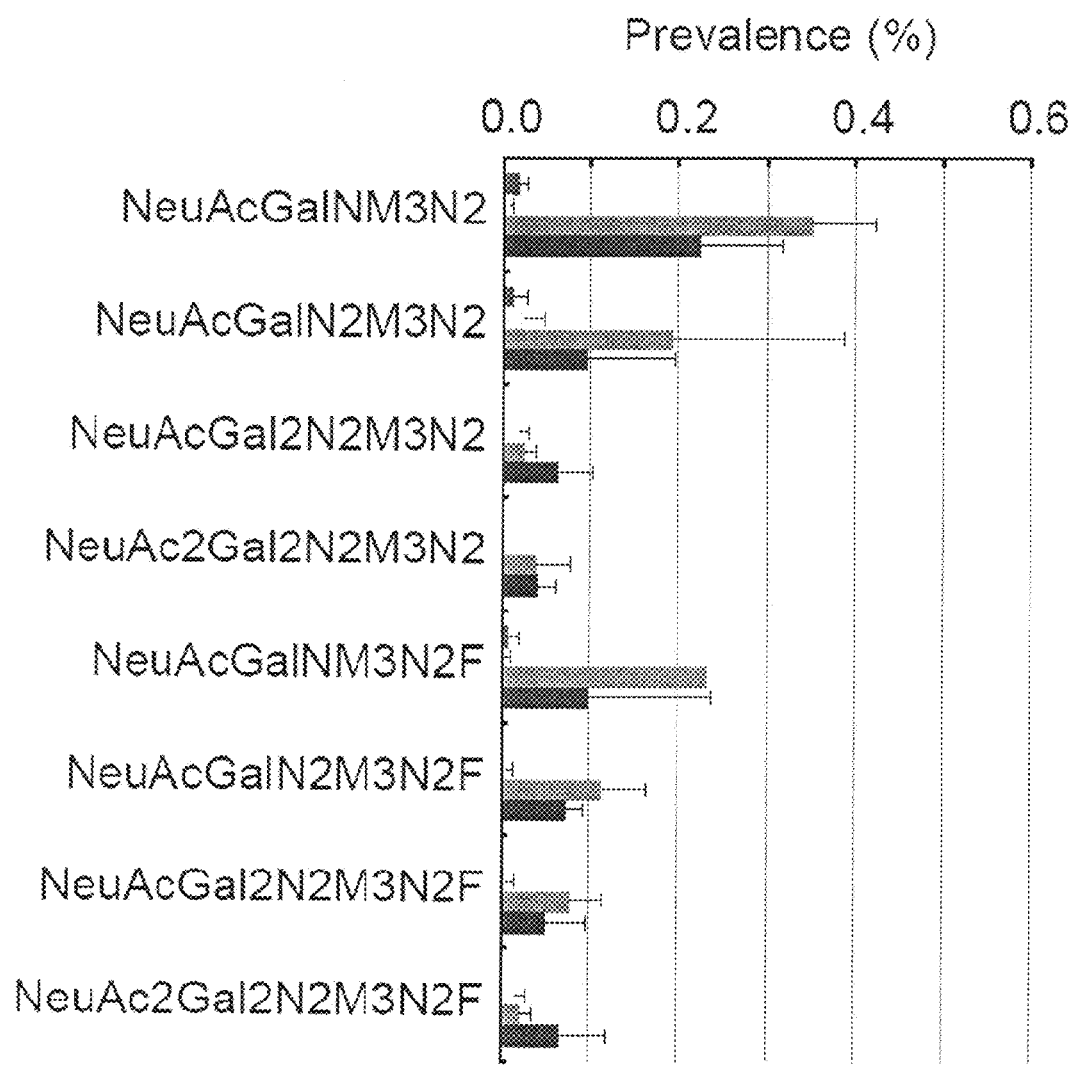
Figure 8D:
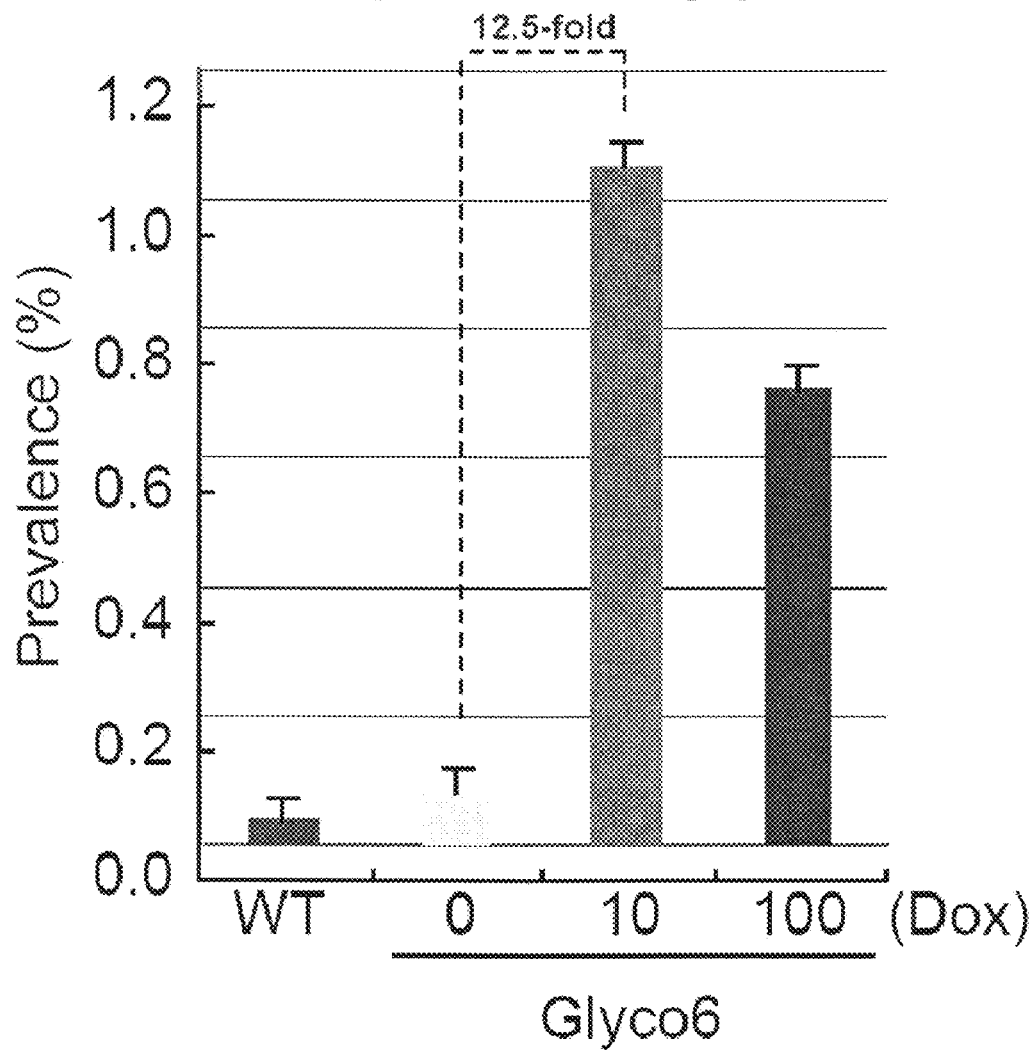

FIG. 6 is a blot and a graph showing semi-quantitative RT-PCR confirms the induction of expression of the Tet-O regulated Glyco6 genes (GalT and GnTII). (A) RT-PCR products. DmGAPDH is an internal constitutive control gene. (B) Induction of Glyco6 genes normalized to DmGAPDH. Values are mean±sd of three independent experiments. Inducible GalT and GnTII genes were up-regulated by the addition of dox to the food, while transcription of the constitutive genes ST6, ST3, SAS and CMP-SAS was not affected.

FIG. 7 shows the results of NSI-MS analysis of permethylated N-glycan profiles of dox-induced strains revealing increased expression of sialylated glycans. (A) Full MS spectrum of N-glycan profiles from uninduced (0 dox) Glyco6 larvae, dominated by high- and paucimannose type strucutures. (B) Total Ion Mapping (TIM) profile of (0 dox) N-glycans. The TIM signal reports the abundance of fragment ions ($MS^2$) detected within overlapping collection windows, each 2 mass units in width, stepped across the full mass range of the instrument. (C) TIM scans filtered for the presence of diagnostic $MS^2$ fragments demonstrated increased abundance of sialylated N-linked glycans in Glco6 larvae treated with doxycyclin. Filtered scans highlight TIM scan times (analogous to m/z values) for parent ions that give rise to specific MS2 fragments. Here, we show scan filter profiles for loss of sialic acid (base peak 398; 375+Na+) for 0, 10, and 100 dox-treated Glyco6 larvae and wild-type across the TIM range of 6-10 min. In 10 and 100 dox, dominant peaks correspond to triply and doubly charged ions of NeuAc2Gal2N2M3N2F and NeuAcGalNM3N2F, respectively, indicating that doxycyclin induces the expression of sialylated glycans that are barely detectable in control larvae. (D and E) Confirmation of the biantennary sialylated glycan structure based on MS2/MS3 fragmentation. Sialylated glycan structures in larvae were confirmed from their molecular mass (m/z) and from their fragmention patterns by MSn. For example, molecular mass of an expected sialylated glycan, NeuAc2Gal2N2M3N2, is 2793 (sodium adduct) singly charged and 1408 doubly charged. Fragmentation of the molecular ion by $MS^2$ produces loss of a single sialic acid as NeuAc (12202+). Subsequent fragenstation of this ion reveals an MS3 pattern which is consistent with the NeuAcGal2N2M3N2 glycan.

FIGS. 8A-8D show chows the glycan prevalences in control and doxycyclin induced Glyco6. The total glycan profile produced by PNGaseA digestion is presented for nominally wild-type (w1118), uninduced Glyco6 (Glyco6-0 Dox with ManNAc) and induced Glyco6 (10 or 100 Dox with ManNAc). The prevalences of individual glycans are determined as a percent of the total glycan profile.

Figure 9:
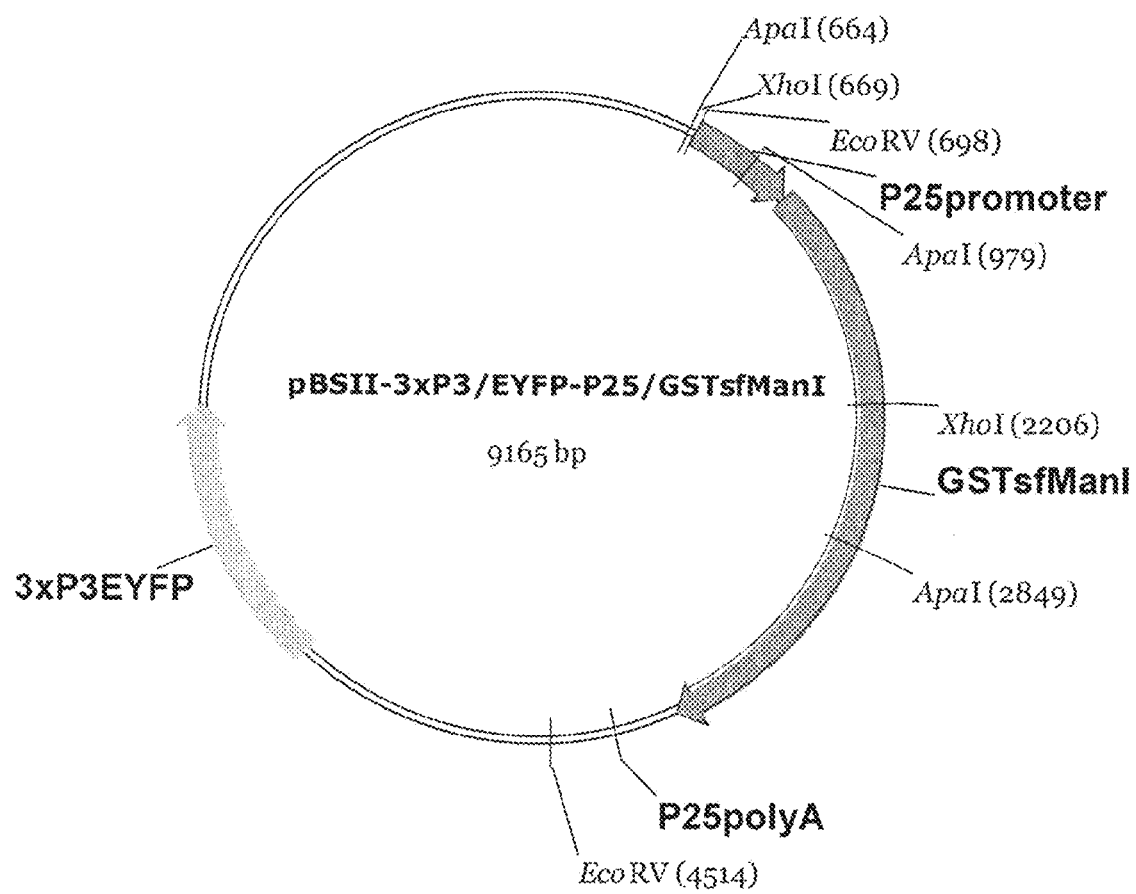

FIG. 9 is a target gene construct suitable for expressing a GST fusion protein in *B. mori*.

Figure 10:
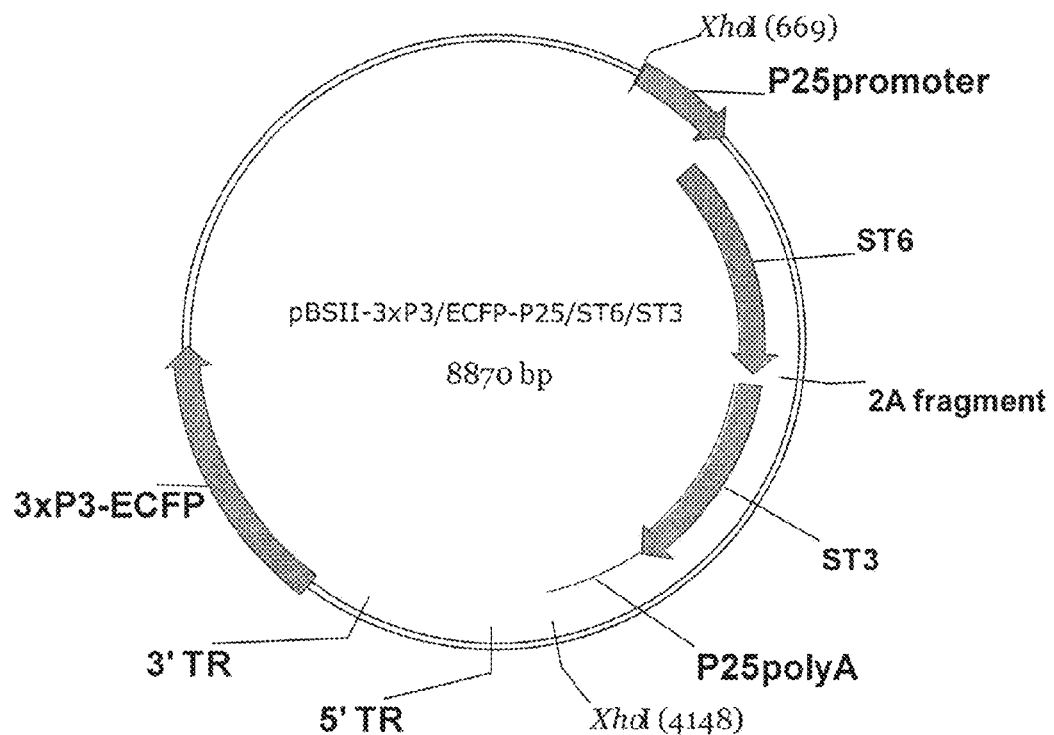

FIG. 10 shows a two gene construct encoding ST6/ST3 suitable for expression in *B. mori*.

Figure 11:
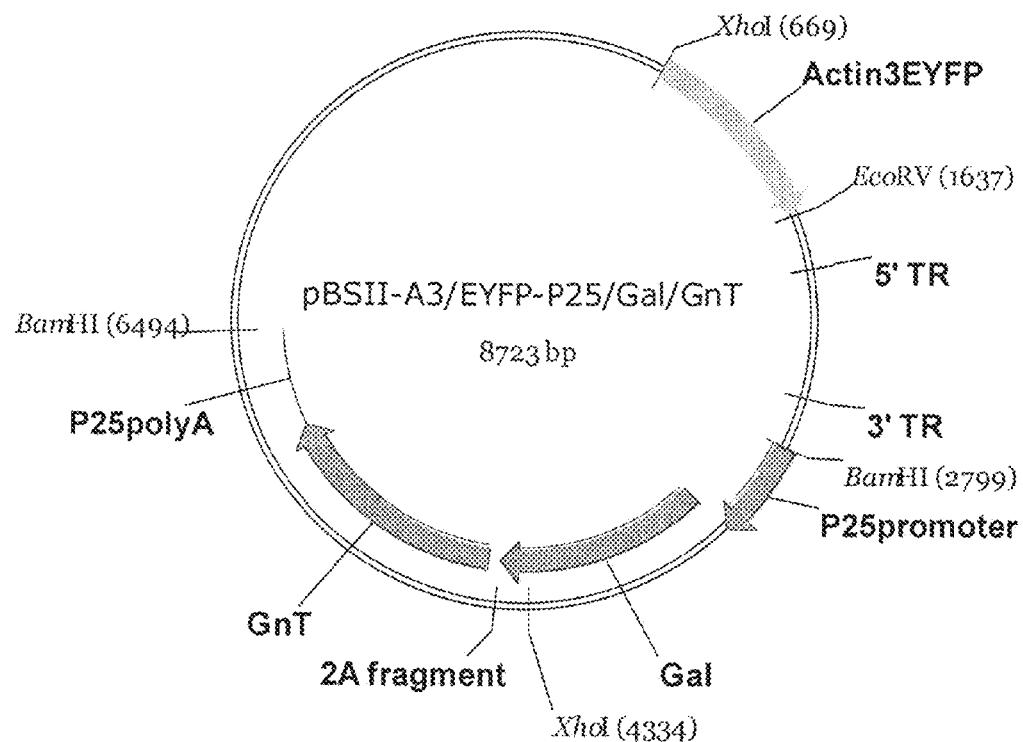

FIG. 11 shows a two gene construct encoding Gal/GnT suitable for expression in *B. mori*.

Figure 12:
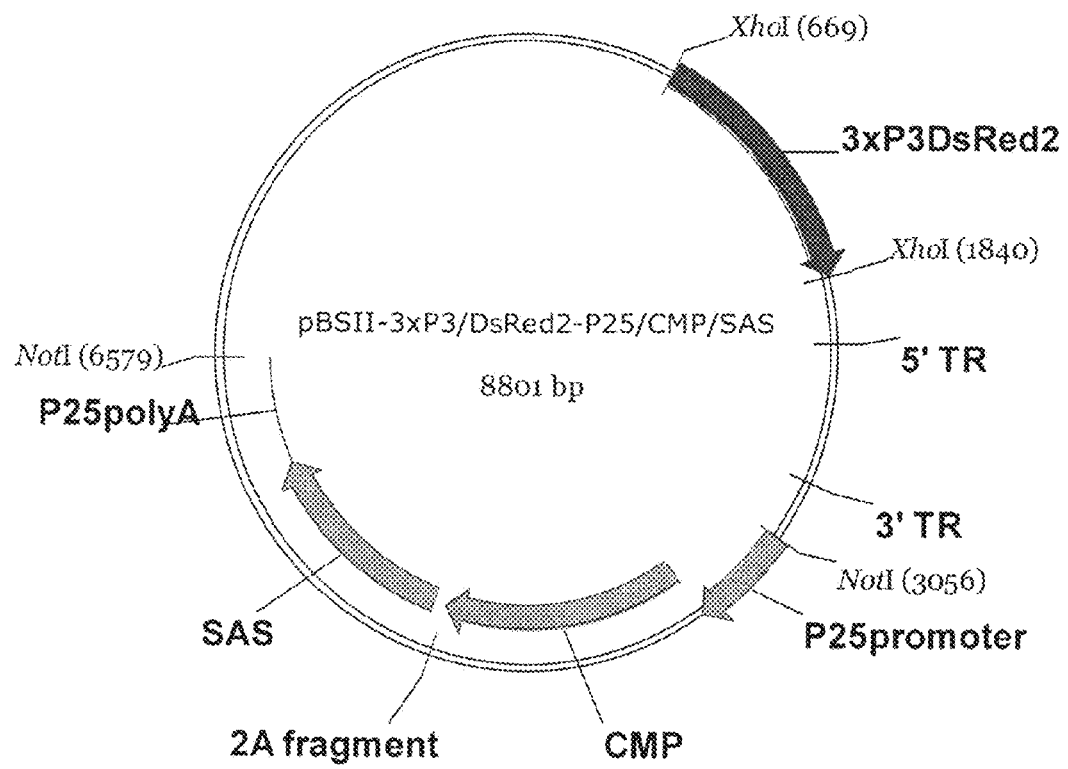

FIG. 12 shows a two gene construct encoding CMP/SAS suitable for expression in *B. mori*.

Figure 13:
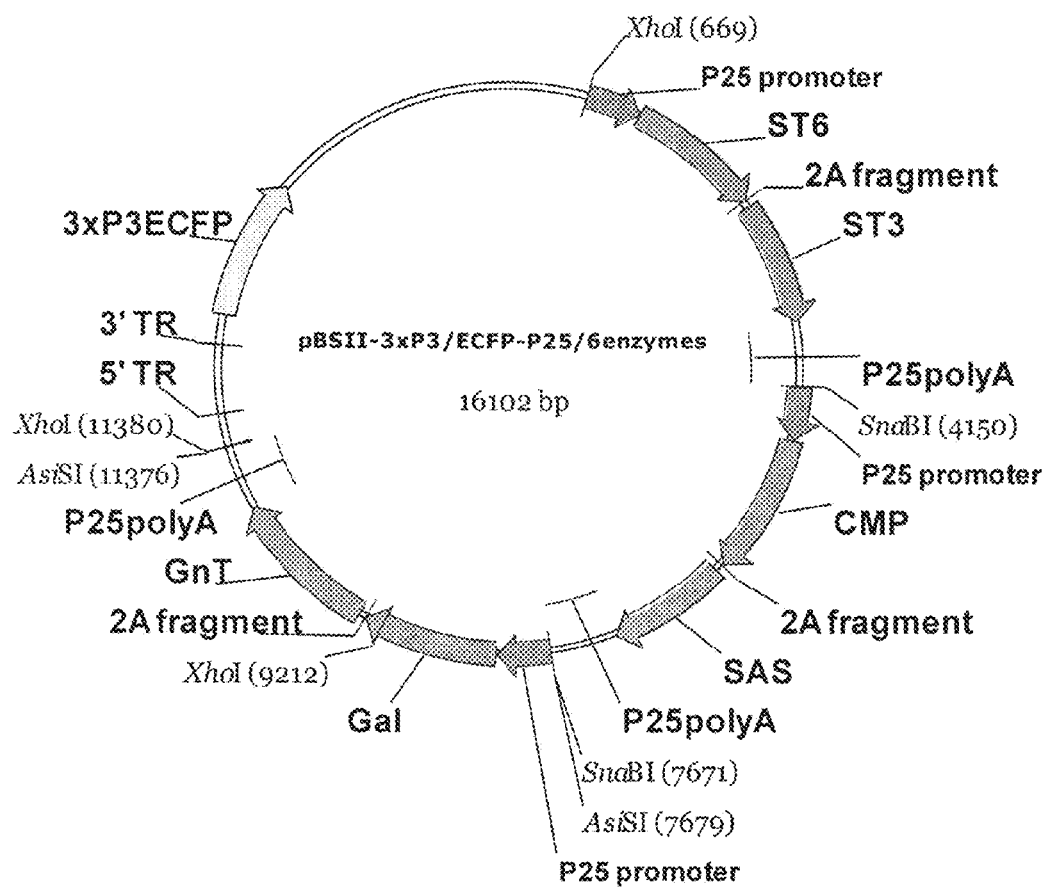

FIG. 13 shows a construct encoding six genes suitable for producing mammalianized glycoproteins in the silk worm.

DESCRIPTION OF THE INVENTION

This invention relates to insects (such as insect larvae) which contain, in at least some of their cells, expressible nucleic acid sequences encoding one or more (e.g., two or more) of a set of glycosylation enzymes noted below, such that expression of the glycosylation enzyme(s) allows for the production of partially or completely mammalianized (e.g., humanized) glycosylated polypeptides of interest that is introduced into, or that is present endogenously in, the insect. The introduced nucleic acid encoding the polypeptide is generally a recombinant nucleic acid (which may comprise coding sequences that are endogenous to, or heterologous to, the insect). Preferably, the recombinant polypeptide of interest is heterologous to the insect. In some embodiments, the glycosylation enzymes are produced in catalytic amounts. That is, the expression of the glycosylation enzyme(s) is effective and sufficient to glycosylate, in the insect, a polypeptide of interest (e.g., a heterologous polypeptide) in a mammalianized glycosylation pattern, yet is not so great that it significantly inhibits viability of the insect, or compromises the ability of the insect to produce high yield of the mammalianized polypeptide of interest. In other embodiments, one or more of the glycosylation enzymes are produced in greater amounts (e.g., at the same level as a heterologous polypeptide that is to be glycosylated). An "effective amount" of a glycosylation protein is an amount that results in partial or completely mammalianized glycosylation of a heterologous polypeptide that is introduced into, or is endogenously present in, the insect. In some embodiments, the glycosylation enzymes are produced in a coordinate fashion. The expressible nucleic acid sequences can be stably integrated into the somatic and germ line cells of the insect (in a transgenic insect); or they can be integrated in the somatic cells (e.g., following introduction into the insect with, for example, a suitable transposon-based vector or retrovirus vector); or they can be transiently produced (e.g., following introduction into the insect with, for example, a baculovirus-based vector).

The invention also relates to methods using an insect as above for producing a polypeptide of interest, such as a heterologous polypeptide, such that the polypeptide of interest exhibits a partially or completely mammalianized glycosylation pattern. For example, an expressible nucleic acid encoding the polypeptide of interest can be introduced an insect which is transgenic for the mentioned glycosylation enzyme(s) (e.g., the expressible nucleic acid is fed to the transgenic insect) in either a baculovirus-based vector, a transposon-based vector, or a retrovirus vector, such that the introduced nucleic acid becomes either transiently or stably introduced into a somatic cell of the insect, and the protein of interest is expressed and glycosylated in that somatic cell. Alternatively, a multiply transgenic insect can be generated, in which expressible nucleic acid encoding the polypeptide of interest and expressible nucleic acid encoding the glycosylation enzyme(s) are both stably integrated in the somatic and germ line cells of the insect. The polypeptide of interest can then be produced and glycosylated in the multiply transgenic insect cells. In another embodiment, a nucleic acid comprising expressible nucleic acid sequences encoding the glycosylation enzyme(s) and a nucleic acid comprising expressible nucleic acid sequences encoding the polypeptide of interest are co-introduced (either on the same vector or on different vectors) into somatic cells of a non-transgenic insect. The vector may be, e.g., a baculovirus-based vector, a transposon-based vector, or a retrovirus vector. The polypeptide of interest is then produced and glycosylated in somatic cells that contain both nucleic acids.

One embodiment of the invention is an insect comprising in at least some of its cells at least two of the glycosylation enzymes noted below (e.g., in catalytic amounts) and a heterologous polypeptide of interest, wherein the heterologous polypeptide is glycosylated by the glycosylation enzymes in a mammalian (e.g., human) glycosylation pattern.

Advantages of the insects and methods of the invention include that the insects are simple and economical to cultivate (for example, insects have fewer requirements for special growth conditions than do cells in culture, and can be cultivated at low cost, in a controlled environment); high yields of the glycosylated polypeptide can be produced rapidly, for large scale production; polypeptides produced in insect cells by the methods of the invention are unlikely to be contaminated by mammalian viruses or prions; insect cultures (e.g., larval cultures) can be grown under space-efficient conditions and can be synchronized to reach the same level of maturity at the same time; and one can control toxicity to the insect, thereby achieving high survivability, in spite of the complexities of heterogeneity of cells in the insect, a complex physiological environment, and the variety of life phases during insect development. Each larva (caterpillar) is effectively a self-contained mini-bioreactor consisting of millions of host cells. Mass rearing, infecting, and harvesting proteins from these larval bioreactors allows one to capitalize on the low cost and great scalability of the insect as a protein production system. In some embodiments, expression of the glycosylation enzyme(s) is regulatable (e.g., inducible). The ability to avoid constitutive production of glycosylation enzymes, which might be toxic to the insect, or might reduce the yield of a glycosylated protein of interest, is an advantage of this embodiment of the invention.

Glycosylation enzymes involved in the present invention include the following:

N-glycoproteins are one subclass of eukaryotic glycoproteins that are particularly important in biotechnology. Many pharmaceutically relevant products, such as immunoglobulins, cytokines, blood clotting factors, and anticoagulants are N-glycosylated. The glycans on these molecules play important roles in their functions and influence their therapeutic potential. For example, terminal sialic acids influence the pharmacokinetics of N-glycoproteins because nonsialylated N-glycoproteins are rapidly cleared from the circulatory system.

The Mammalian N-glycosylation Pathway.

Important enzymatic functions involved in the mammalian protein N-glycosylation are well defined (see, e.g., Komfeld et al. (1985) Ann. Rev. Biochem. 54, 631-664; Montreuil et al. (1995) "Glycoproteins". New Comprehensive Biochemistry (A. Neuberger, and L. L. M. Van Deenen, Eds.), 29a Elsevier, Amsterdam; Varki et al. (1999). "Essentials of Glycobiology." Cold Spring Harbor Press, Cold Spring Harbor, N.Y.). The products of this processing pathway are termed "N-glycoproteins" because their carbohydrate side chains are linked to the polypeptide backbone by an N-glycosidic bond to the asparagine residue. This pathway begins with the transfer of a pre-assembled glycan, $Glc_3Man_9GlcNAc_2$, from a lipid carrier to an asparagine residue within a specific recognition site in a nascent polypeptide (see FIG. 1A, Step 1). Standard monosaccharide abbreviations used in this application include: Glc (glucose), Man (mannose), GlcNAc (N-acetylglucosamine), Gal (galactose), GalNAc (N-acetylgalactosamine), Fuc (fucose), Sia (sialic acid), ManNAc (N-acetylmannosamine). Transfer occurs as the nascent polypeptide enters the lumen of the rough endoplasmic reticulum (RER) and is followed by trimming of the glucose residues (FIG. 1A, step 2) to produce $Man_9GlcNAc_2$, which is generally termed a "high-mannose" N-glycan.

In some cases, there is no further processing and the high mannose N-glycan is the end product. In other cases, the high mannose glycan serves as an intermediate that is further processed by a sequential series of enzymatic reactions catalyzed by glycosidases and glycosyltransferases localized along the secretory pathway. Four of the nine mannose residues are trimmed by class I alpha-mannosidases (Man I's) in the ER and Golgi apparatus (FIG. 1A step 3), yielding $Mans-GlcNAc_2$. One GlcNAc residue is then added by N-acetylglucosaminyltransferase I (GlcNAc-TI; FIG. 1A, step 4), which permits alpha-mannosidase II (Man II; FIG. 1A, step 5) to remove two more mannose residues. This leads to elongation of the trimmed structures and the production of "complex" N-glycans by various Golgi glycosyltransferases, including N-acetylglucosaminyl-transferases (GlcNAc-Ts), fucosyltransferases (Fuc-Ts), galactosyltransferases (Gal-Ts), N-acetylgalactosaminyltransferases (GalNAc-T's), and sialyltransferases (Sial-Ts), as shown in steps 5-7. The complex N-glycans shown on the bottom right of FIG. 1A are common "biantennary" structures. Mammalian cells also can produce more highly branched complex N-glycans with up to five antennae.

Figure 1B:
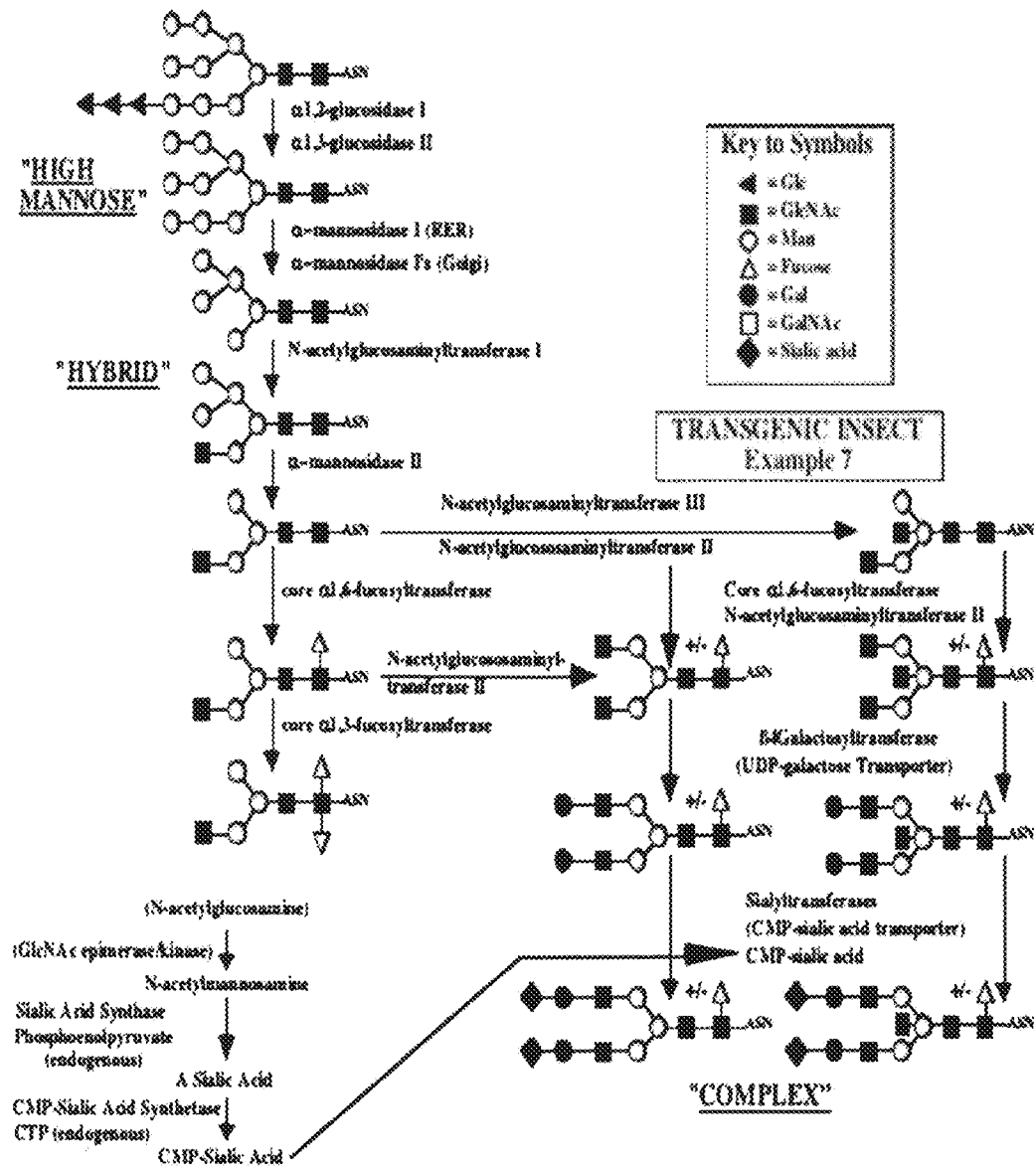
FIG. 1B shows the enzymes required to produce mammalianized N-glycans.

In addition to the glycosyltransferases shown in FIG. 1A, N-glycan elongation requires various nucleotide sugars, including UDP-GlcNAc, UDP-Gal, and CMP-sialic acid. These compounds are the donor substrates for the glycosyltransferases catalyzing the elongation reactions. The nucleotide sugars are synthesized in the cytoplasm or nucleus of the cell and are imported into the lumen of the Golgi apparatus, where the elongation reactions occur, by specific nucleotide sugar transporters. See FIG. 1B.

The insect N Glycosylation Pathway.

The initial steps in the insect N-glycosylation pathway are identical to those in the mammalian pathway, producing the common intermediate, $GlcNAcMan_3GlcNAc_2$ (+/−Fuc). While mammalian cells have sufficient levels of glycosyltransferases to elongate this common intermediate and produce complex. N-glycans, insect cells generally appear to have low or undetectable levels of these activities and no detectable CMP-sialic acid. In addition, some insect cells have a processing N-acetylglucosaminidase (GlcNAcase) that trims this intermediate to produce simple "paucimannose" N-glycans. Accordingly, the major processed N-glycans found on recombinant glycoproteins produced by baculovirus infected insect cell lines or larvae are usually paucimannose structures (FIG. 1A). This conclusion is supported by data from, e.g., structural studies on the N-glycans isolated from insect or insect cell-derived glycoproteins, the use of specific N-glycan processing inhibitors, enzyme activity assays, analyses of endogenous nucleotide sugar levels, and the isolation and characterization of insect genes encoding various N-glycan processing enzymes. Baculovirus-expressed recombinant glycoproteins almost never have terminally sialylated N-glycans. The inability to routinely produce complex, terminally sialylated N-glycans is a major technical barrier associated with the use of the baculovirus expression system for recombinant glycoprotein production, at least because baculovirus produced unsialylated glycoproteins have very short half-lives in vivo. The present inventors have created transgenic lepidopteran insect larvae that can support the production of humanized recombinant glycoproteins by baculovirus expression vectors. The inventive larvae express levels of relevant enzymes that are effective to produce complex, terminally sialylated N-glycans in high quantity and consistent quality.

In one aspect, this invention relates to a transgenic insect, or progeny thereof, whose somatic and germ cells contain recombinant nucleic acid:

A. two or more of the glycosylation enzymes: a beta-1,2-N-acetylglucosaminyltransferase (e.g., beta-1,2-N-acetylglucosaminyltransferase I and/or beta-1,2-N-acetylglucosaminyltransferase II); a β1,4-galactosyltransferase (e.g., beta 4-galactosyltransferase I); and/or a sialyltransferase [e.g., one of the many suitable alpha 2,6-sialyltransferases and/or one of the many suitable alpha 2,3-sialyltransferases (such as alpha 2,3-sialyltransferase III and/or alpha 2,3-sialyltransferase IV)]; or B. one or more of the glycosylation enzymes: a beta-1,2-N-acetylglucosaminyltransferase (e.g., beta-1,2-N-acetylglucosaminyltransferase I and/or beta-1,2-N-acetylglucosaminyltransferase II); and/or a sialyltransferase [e.g., one of the many suitable alpha 2,6-sialyltransferases and/or one of the many suitable alpha 2,3-sialyltransferases (such as alpha 2,3-sialyltransferase III and/or alpha 2,3-sialyltransferase IV)], wherein each recombinant nucleic acid encoding a glycosylation enzyme is integrated in the insect genome, and is present in one or more copies, wherein each recombinant nucleic acid encoding a glycosylation enzyme is operably linked to an expression control sequence, and wherein expression of said glycosylation enzyme(s) (e.g., in a catalytic amount) allows for production of a partially or completely mammalianized glycosylated protein in the insect.

In one embodiment, the somatic and germ cells contain recombinant nucleic acid encoding:

A. two or more of the glycosylation enzymes:
 a) beta-1,2-N-acetylglucosaminyltransferase I,
 b) beta-1,2-N-acetylglucosaminyltransferase II,
 c) a β1,4-galactosyltransferase (e.g., beta 4-galactosyltransferase I), and/or
 d) a sialyltransferase [e.g., an alpha 2,6-sialyltransferase and/or an alpha 2,3-sialyltransferase (such as alpha 2,3-sialyltransferase III and/or alpha 2,3-sialyltransferase IV)], or B. one or more of the glycosylation enzymes:
 a) beta-1,2-N-acetylglucosaminyltransferase I,
 b) beta-1,2-N-acetylglucosaminyltransferase II, and/or
 d) a sialyltransferase [e.g., an alpha 2,6-sialyltransferase and/or
 an alpha 2,3-sialyltransferase (such as alpha 2,3-sialyltransferase III and/or alpha 2,3-sialyltransferase IV)].

In another embodiment, the somatic and germ cells contain recombinant nucleic acid encoding:

A. two or more of the glycosylation enzymes:
 b) beta-1,2-N-acetylglucosaminyltransferase II,
 c) a β1,4-galactosyltransferase (e.g., beta4-galactosyltransferase I),
 d-1) an alpha 2,6-sialyltransferase, and/or
 d-2) an alpha 2,3-sialyltransferase (such as alpha 2,3-sialyltransferase III and/or alpha 2,3-sialyltransferase IV)], or B. one or more of the glycosylation enzymes:
 b) beta-1,2-N-acetylglucosaminyltransferase II,
 d-1) an alpha 2,6-sialyltransferase, and/or
 d-2) an alpha 2,3-sialyltransferase (such as alpha 2,3-sialyltransferase III and/or alpha 2,3-sialyltransferase IV).

The nucleic acid sequence information for each of these proteins is available at the NCBI website in GenBank. To illustrate, in order to retrieve the mammalian sequence information required to encode the glycosylating enzyme sequence of interest, the skilled person accesses the PUBMED website for example (there are others available on the web), and selects the "nucleotide tab" in the drop down SEARCH menu and enters the name of the enzyme. Using beta-1,2N-acetylglucosaminyltransferase II for example, the search provides the skilled person with mammalian mRNA sequences encoding this enzyme which are readily converted into cDNA sequences for expression in the silkworm. Alternatively, the skilled person can search PUBMED using the enzyme as a search term and identify literature references that provide the relevant sequence information.

The expression control sequences to which each recombinant nucleic acid encoding a glycosylation enzyme is operably linked may be the same or different. In all of the embodiments discussed herein in which expression control sequences regulate the expression of more than one nucleic acid sequence, the expression control sequences may be the same or different.

The integrated copies may be tandemly integrated, integrated into different regions of the same chromosome, or integrated into different chromosomes. As used herein, the term "recombinant" nucleic acid refers to a nucleic acid that encodes a polypeptide which is heterologous to the insect, and/or a nucleic acid which has been genetically engineered (e.g., cloned into a vector) before being introduced into the insect. Thus, a nucleic acid encoding a protein originating from a particular type of insect (endogenous to that type of insect), but engineered so as to be produced at increased levels, and then introduced back into that type of insect, is considered to be recombinant.

As used herein, the singular forms "a," "an," and "the" include plural referents unless the context clearly dictates otherwise. For example, "an" alpha sialyltransferase, as used above, means one or more alpha sialyltransferases, which can encompass two different types of alpha sialyltransferase, such as an alpha 2,6-sialyltransferase and an alpha 2,3-sialyltransferase. A coding sequence that is operably linked to an expression control sequence is sometimes referred to herein as an "expressible" nucleic acid sequence.

In embodiments of the invention, the somatic and germ cells of the transgenic insect comprise genomically integrated recombinant nucleic acid encoding enzyme a);
enzyme a) and enzyme b);
enzyme a), enzyme b) and enzyme c); or, preferably,
enzyme a), enzyme b), enzyme c) and enzyme d).

When more than one of these glycosylation enzymes are present in the transgenic insect, they may be integrated into different regions of the same chromosome, or integrated into different chromosomes.

In one embodiment, if nucleic acid encoding enzyme c) is present, nucleic acid encoding at least one of enzymes a), b) or d) is also present.

Insect cells generally do not comprise enzymes a) through d) above, or comprise such low amounts of these enzymes that little if any enzymatic activity is detectable. Therefore, N-glycosylated glycoproteins that are produced in insect cells generally exhibit structures similar to the "paucimannose" structure shown in FIG. 1A. By contrast, N-glycosylated glycoproteins that are produced in mammalian cells exhibit structures similar to the "complex" structures shown in FIG. 1B. These complex structures are generated by the sequential action of proteins a) through c) above, followed by the action of enzyme(s) d), which introduce sialic acid moieties onto the termini of the arms of the biantennary carbohydrate side chains. For example, an alpha 2,6-sialyltransferase can sialylate the lower (alpha-3) branch of a biantennary glycan; an alpha 2,3-sialyltransferase can sialylate the upper (alpha-6) branch and/or lower (alpha-3) branch of a biantennary glycan; and various other combinations can occur. Either partially or fully sialylated structures are suitable for various uses. Sialic acid residues also may be alpha 3- or alpha 6-linked to additional branches, if those branches are produced by the actions of N-acetylglucosaminyltransferases IV, V, and VI.

A polypeptide that is acted upon by, for example, enzyme a), is referred to herein as a partially mammalianized (e.g., humanized) glycopolypeptide. It differs from most naturally produced polypeptides in the insect by virtue of the presence of the carbohydrate residue provided by enzyme a). Similarly, any polypeptide glycosylated by fewer than the full set of enzymes a) through d) above is also referred to herein as a "partially mammalianized (e.g., humanized)" glycopolypeptide. A glycopolypeptide that exhibits a "complex" glycoprotein structure (e.g., a mammalian (preferably, human) glycan profile) is said to be "completely mammalianized (humanized)", or to exhibit a glycosylation pattern characteristic of mammals (e.g., humans). Partially and completely mammalianized glycosylation structures are found in many types of mammalian cells, such as bovine or human cells. The term, a "mammalianized" glycopolypeptide, as used herein, refers to a glycopolypeptide that exhibits a glycan profile characteristic of a mammalian glycoprotein, as discussed above. A "mammalianized" glycopolypeptide, as used herein, encompasses both partially and completely mammalianized glycopolypeptides. The terms "mammalianized glycopolypeptide," "mammalianized glycoprotein," "mammalianized polypeptide" and "mammalianized protein" are sometimes used interchangeably herein.

Partially or completely mammalianized polypeptides exhibit a number of advantages compared to polypeptides produced by an insect that lacks the glycosylation enzymes of the invention. These advantages include, e.g., enhanced stability when introduced into a mammal, altered activities, or the like. An insect that expresses fewer than a full set of enzymes a) through d) has a variety of utilities, which will be evident to the skilled worker. For example, such an insect can be used to generate a protein of interest that exhibits a partially mammalianized glycosylation pattern, and that consequently exhibits improved properties compared to a polypeptide produced by an insect that is not so modified.

If an insect naturally produces small amounts of, for example, one or more enzymes which lie upstream in the glycosylation pathway, expression of an enzyme that lies further downstream in the pathway can cap and stabilize the glycosylation product resulting from the small amounts of the upstream enzyme(s). Therefore, an insect that naturally makes one or more of the upstream enzymes may be transgenically modified to express one or more recombinant downstream enzymes, provided that the transgenic insect produces sufficient amounts of a sialylization enzyme to produce a sialic acid cap.

Another embodiment of the invention is a transgenic insect as above whose somatic and germ cells further comprise recombinant nucleic acid encoding one or more of the following glycosylation enzymes:

e) a sialic acid synthase and/or
f) CMP-sialic acid synthetase, wherein each recombinant nucleic acid encoding a glycosylation enzyme is genomically integrated in the insect genome, and is present in one or more copies, and wherein each recombinant nucleic acid encoding a glycosylation enzyme is operably linked to an expression control sequence. Preferably, both e) and f) are present.

Some insects may generate sufficient sialic acid, themselves, to sialylate heterologous proteins in the methods of the invention. However, many insects lack such an endogenous source of sialic acid, or produce insufficient quantities. Therefore, for those insects, the needed sialic acid can be introduced into the insects with their diet. Alternatively, and preferably, the sialic acid can be provided by introducing into the cells of the insects enzymes e) and/or f), preferably both e) and f). For example, nucleic acids expressing the enzymes can be integrated into the cells of the insect. These two enzymes together, when presented with the substrate ManNAc (N-acetylmannosamine) will generate the needed CMP-sialic acid. The ManNAc can be presented to the insect by conventional means, e.g., orally, in its diet. In a preferred embodiment, a transgenic insect of the invention expresses in its somatic and germ line cells all of enzymes a) through f).

Optionally, the somatic and germ cells of any of the transgenic insects described above further comprise recombinant nucleic acid encoding one or more of the following auxiliary glycosylation proteins:

g) UDP-N-acetylglucosamine 2 epimerase/N-acetylmannosamine kinase;
h) beta-1,4-N-acetylglucosaminyltransferase III;
i) beta-1,4-N-acetylglucosaminyltransferase IV;
j) beta-1,6-N-acetylglucosaminyltransferase V;
k) beta-1,4-N-acetylglucosaminyltransferase VI;
l) a beta 1,4-N-acetylgalactosaminyltransferase;
m) CMP-sialic acid transporter;
n) UDP-galactose transporter, wherein each recombinant nucleic acid encoding an auxiliary glycosylation protein is genomically integrated in the insect genome, in one or more copies, and wherein each recombinant nucleic acid is operably linked to an expression control sequence.

Enzyme g) converts N-acetylglucosamine to N-acetylmannosamine-phosphate, which allows one to feed larvae N-acetylglucosamine, rather than N-acetylmannosamine, to support sialoglycoprotein biosynthesis. N-acetylglucosamine is considerably less expensive than N-acetylmannosamine.

Figure 2:
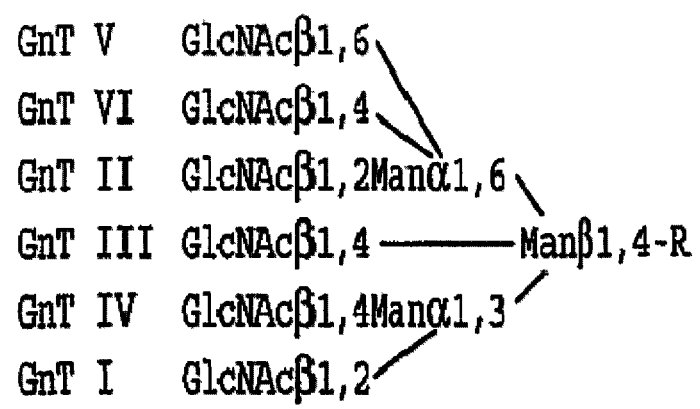
FIG. 2 shows N-glycosylation pathways by which GlcNAc-transferase I to VI incorporate GlcNAc residues into a Man (α1-6) [Man (α1-3)] Manβ-RN-glycan core. (Montreuil et al. (eds.), Glycoproteins, Vol. 29a. Elsevier, Amsterdam, 1995)

Enzymes h) through k) allow insect cells to produce tri, tetra, or pentaantennary N-glycans. See FIG. 2 for a diagram of the reactions carried out by some of these enzymes.

Enzyme h) adds "bisecting" GlcNAc in β1,4 linkage to the core.

Enzyme i) adds GlcNAc in β1,4 linkage to the alpha 3 branch mannose.

Enzyme j) adds GlcNAc in β1,6 linkage to the alpha 6 branch mannose.

Enzyme k) adds GlcNAc in β1,4 linkage to the alpha 6 branch mannose.

Enzyme l) transfers N-acetylgalactosamine in β1,4 linkage to terminal N-acetylglucosamine residues in N-glycans. It can serve as an alternative to β1,4-galactosyltransferase, transferring GalNAc, instead of Gal to outer chain positions of some N-glycoproteins.

Protein m) transports CMP-sialic acid into the Golgi apparatus. (Although it was unexpected that insect cells would have this transporter, cell culture studies performed by the present inventors indicate that insect cells can somehow move CMP-sialic acid into Golgi, even in the absence of an exogenous transporter which would enhance CMP-sialic acid transport.) Protein n) transports UDP-galactose into Golgi apparatus. (Some insect cells express low levels of this transporter. Engineering insect cells to express a mammalian UDP-galactose transporter can improve the efficiency of the transport.) These auxiliary enzymes are listed above in the approximate order of preference.

The nucleic acids encoding glycosylation enzymes that are expressed in the insects of the invention can be obtained from any suitable source, examples of which will be evident to skilled workers. For example, the enzyme can be one that is naturally produced in the insect, but at ineffectively low levels. An insect of the invention can be designed to produce increased amounts of the enzyme, which are effective for producing a partially or completely mammalianized glycosylation pattern in a polypeptide of interest. The genes encoding the glycosylation enzyme can be obtained from any vertebrate (such as a chicken or a mammal). Suitable mammalian sources include, e.g., mouse, rat, cow or human. Enzymes obtained from different sources can be used in conjunction with one another.

Methods for cloning and expressing such enzymes are known. A sequence "obtained" from a particular source does not necessarily encode a polypeptide sequence identical to that of the wild type enzyme from that source. Any glycosylation enzyme that retains the enzymatic function of the wild type enzyme, including naturally occurring allelic variants or mutations that are introduced artificially into the protein, can be used. Enzymatically active fragments of the enzyme can also be used.

As used herein, the term "insect" includes any stage of development of an insect, including a one-celled germ line cell, a fertilized egg, an early embryo, a larva, including any of a first through a fifth instar larva, a pupa, or an adult insect. For the production of mammalianized polypeptides of interest, a large larva, such as a fourth or fifth instar larva is preferred. It will be evident to a skilled worker which insect stage is suitable for a particular purpose, such as for direct production of a glycosylated polypeptide of interest, for storage or transport of an insect to a different location, for generation of progeny, for further genetic crosses, or the like.

A variety of insects are suitable for use in the present invention. Suitable insects include, without limitation, Lepidoptera (e.g., *Bombyx mori*, *Manduca sexta*, *Hyalophora cecropia*, *Spodoptera exigua*, *Spodoptera frugiperda*, *Spodoptera litoralis*, *Spodoptera litura*, *Heliothis virescens*, *Helicoverpa zea*, *Helicovepa armigera*, *Trichoplusia ni*, *Plutella xylostella*, *Anagrapha falcifera*, *Cydia pomonella*, *Cryptophlebia leucotreta*, and *Estigmene acrea*), and insect species from the orders Coleoptera, Hymenoptera, Orthoptera, and Diptera. Preferably, the insect is from the order Lepidoptera, most preferably *Bombyx mori*.

The term "expression control sequence", as used herein, refers to a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc. An expression control sequence is "operably linked" to a nucleotide coding sequence when the expression control sequence is positioned in such a manner to effect or achieve expression of the coding sequence. For example, when a promoter is operably linked 5' to a coding sequence, expression of the coding sequence is driven by the promoter.

Suitable expression control sequences that can function in insect cells will be evident to the skilled worker. In some embodiments, it is desirable that the expression control sequence comprises a constitutive promoter. Among the many suitable "strong" promoters which can be used are the baculovirus promoters for the p10, polyhedrin (polh), p 6.9, capsid, and cathepsin-like genes. Among the many "weak" promoters which are suitable are the baculovirus promoters for the ie1, ie2, ie0, et1, 39K (aka pp31), and gp64 genes. Other suitable strong constitutive promoters include the *B. mori* actin gene promoter; *Drosophila melanogaster* hsp70, actin, α-1-tubulin or ubiquitin gene promoters; RSV or MMTV promoters; copia promoter; gypsy promoter; and the cytomegalovirus IE gene promoter. If it is desired to increase the amount of gene expression from a weak promoter, enhancer elements, such as the baculovirus enhancer element, hr5, may be used in conjunction with the promoter.

In some embodiments, the expression control sequence comprises a tissue- or organ-specific promoter. Many such expression control sequences will be evident to the skilled worker. For example, suitable promoters that direct expression in insect silk glands include the *Bombyx mori* p25 promoter, which directs organ-specific expression in the posterior silk gland, and the silk fibroin Heavy chain gene promoter, which directs specific expression of genes in the median silk gland. Example XVI describes the generation and use of transgenic insects of the invention that express glycosylation enzymes specifically in their silk glands.

In general, the glycosylating enzymes of the invention are required in catalytic amounts. Therefore, in one embodiment of the invention, much lower amounts of these enzymes are present than of the heterologous polypeptides of interest, which are generated in massive, large amounts, glycosylated, and harvested for further use. For example, a suitable molar ratio of heterologous protein produced to a glycosylating enzyme may be greater than about 100:1. Alternatively, the amounts of the glycosylating enzymes may be comparable to the amounts of heterologous protein to be glycosylated. A skilled worker can readily select suitable promoters and/or conditions to express suitable amounts of the glycosylating enzymes (e.g., amounts which are sufficient to efficiently) glycosylate relatively high amounts of a protein of interest). Furthermore, a skilled worker can readily ensure that the glycosylation enzymes are present in sufficient local concentrations, and at an optimal time during insect propagation.

In some embodiments of the invention, as is discussed in more detail elsewhere herein, it is desirable that an expression control sequence is regulatable (e.g., comprises an inducible promoter and/or enhancer element). Suitable regulatable promoters include, e.g., *Drosophila* or other hsp70 promoters, the *Drosophila* metallothionein promoter, an ecdysone-regulated promoter, the *Saccharomyces cerevisciae* Gal4/UAS system, and other well-known inducible systems. A Tet-regulatable molecular switch may be used in conjunction with any constitutive promoter, such as those described elsewhere herein (e.g., in conjunction with the CMV—IE promoter, or baculovirus promoters). Another type of inducible promoter is a baculovirus late or very late promoter that is only activated following infection by a baculovirus.

Methods for designing and preparing constructs suitable for generating transgenic insects (or vectors for infection of an insect) are conventional. For these methods, as well as other molecular biology procedures related to the invention, see, e.g., Sambrook et al., Molecular Cloning: A Laboratory Manual, Second Edition, Cold Spring Harbor, N.Y., (1989); Wu et al, *Methods in Gene Biotechnology* (CRC Press, New York, N.Y., 1997), Recombinant Gene *Expression Protocols, in Methods in Molecular Biology*, Vol. 62, (Tuan, ed., Humana Press, Totowa, N.J., 1997); and *Current Protocols in Molecular Biology*, (Ausubel et al, Eds.,), John Wiley & Sons, NY (1994-1999). Some suitable methods are described elsewhere herein.

A variety of immortalized lepidopteran insect cell lines are suitable for infection by the vectors/constructs of the invention. Among these are Sf9 (Vaughn et al. (1977) In Vitro 13, 213-217) and Tn 5B1-4 (Hive Five®; Wickham et al. (1992) *Biotech. Progr.* 8, 391-6).

Methods for generating transgenic insects are conventional. For example, in one embodiment, one or more genes to be introduced are placed under the control of a suitable expression control sequence, and are cloned into a vector, such as a viral vector (e.g., an attenuated baculovirus vector, or a non-permissive viral vector that is not infective for the particular insect of interest). The sequences to be introduced into the insect are flanked by genomic sequences from the insect. The construct is then introduced into an insect egg (e.g., by microinjection), and the transgene(s) then integrate by homologous recombination of the flanking sequences into comparable sequences in the insect genome. One method according to the invention employs an approach adapted from the techniques presented in Yamao et al. (1999) Genes and Development 13, 511-516. In that publication, a non-permissive insect host (*B. mori*) was infected with a recombinant AcMNPV carrying a gene of interest flanked by sequences derived from the host genome. The virus delivered its DNA, but could not consummate its infection cycle. The viral DNA recombined with the host genome via an extremely low frequency homologous recombination event between the host sequences in the viral DNA and the same sequences in the *B. mori* genome.

In another embodiment, the vector is a transposase-based vector. One form of such transposase-based vectors is a viral vector (such as those described above) that further comprises inverted terminal repeats of a suitable transposon, between which the transgene of interest is cloned. One or more genes of interest, under the control of a suitable expression control sequence(s), are cloned into the transposon-based vector. In some systems, the transposon based vector carries its own transposase. However, generally, the transposon based vector does not encode a suitable transposase. In this case, the vector is co-infected into an insect (e.g., an insect larva) with a helper virus or plasmid that provides a transposase. The recombinant vector (along with, generally, a helper) is introduced by conventional methods (such as microinjection) into an egg or early embryo; and the transgene(s) become integrated at a transposon site (such as sequences corresponding the inverted terminal repeat of the transposon) in the insect genome. Suitable types of transposon-based vectors will be evident to the skilled worker. These include, e.g., Minos, mariner, Hermes, sleeping beauty, and piggyBac.

Figure 3:
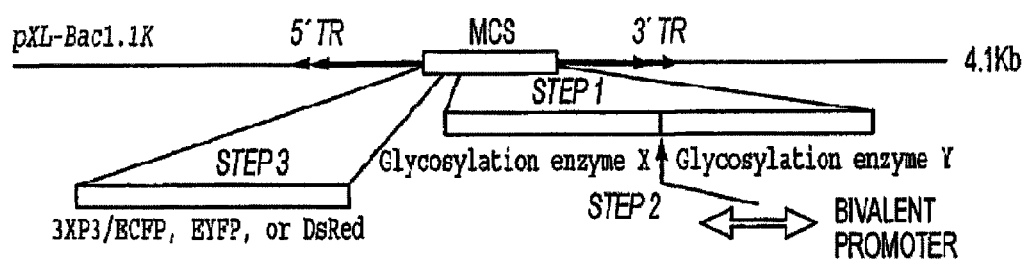
FIG. 3 shows a typical piggyBac vector. The sizes of the promoters, enzyme pairs, piggyBac and GFP marker are as follows.

In a preferred embodiment, the vector is a "piggyBac" vector. A typical piggyBac vector is shown in FIG. 3. The TTAA-specific, short repeat elements are a group of transposons (Class II mobile elements) that have similar structures and movement properties. piggyBac (formerly IFP2) is the most extensively studied of these insertion elements. piggyBac is 2.4 kb long and terminates in 13 bp perfect inverted repeats, with additional internal 19 bp inverted repeats located asymmetrically with respect to the ends (Cary et al. (1989) Virology. 172, 156-69). A piggyBac vector may encode a trans-acting transposase that facilitates its own movement; alternatively, these sequences can be deleted and this function can be supplied on a helper plasmid or virus. In piggyback vectors non-essential genes have been deleted and large inserts can be cloned in their place. Inserts as large as about 15 kB can be cloned into certain piggyBac vectors. This allows, for example, for the insertion of about six or seven genes with their expression control sequences. Thus, a collection of glycosylation enzymes, marker proteins, or the like, can be introduced together via a single transposon vector, into a single site in an insect genome.

Several piggyBac vectors have been developed for insect transgenesis. Two particularly useful constructs, defined as minimal constructs for the movement of piggyBac vectored sequences, were developed by analysis of deletion mutations both within and outside of the boundaries of the transposon (Li et al. (2001) Mol. Genet. Genomics. 266, 190-8). Using constructs such as these it is possible to increase the amount of genetic material mobilized by the piggybac transposase by minimizing the size of the vector. The minimal requirements for movement include the 5' and 3'terminal repeat domains and attendant TTAA target sequences. Nearly all of the internal domain may be removed, although more recent data indicates that some of this region may be required for efficient translocation of the mobilized sequences into the genome of the insect. In addition, a minimum of 50 bases separating the TTAA target sites of the element is required for efficient mobilization (Li et al. (2001), supra).

piggyBac can transpose in insect cells while carrying a marker gene, and movement of the piggyBac element can occur in cells from lepidopteran species distantly related to the species from which it originated. piggybac has been shown to transform *D. melanogaster*, the Carribean fruit fly, *Anastrepha suspena*, the oriental fruit fly, *Bactrocera dorsalis, Bombyx mori, Pectinophora glossypiella, Tribolium castellani*, and several mosquito species. At least three lepidopteran species, *P. gossypiella*, *T. ni* and *B. mori*, have been successfully transformed by the piggyBac element.

Generally, a helper virus or plasmid that expresses a transposase is co-infected with the transposon-based vector as above. Expression of the transposase is determined by the choice of promoter for the insect system being tested. Toward that end, the present inventors have constructed several promoter-driven helper constructs that are useful for lepidopteran transformation, including the *Drosophila* hsp70, baculovirus iel promoter, and *Drosophila* Actin 5C promoter. Of these helper constructs, the hsp70 promoted helper, is particularly useful and serves as the primary helper for the transgenesis experiments in the Examples.

One method according to the invention employs an approach adapted from the techniques presented in Yamao et al., Abstract for poster presentation at the 6th International Conference on the Molecular Biology and Genetics of the Lepidoptera, in Kolympari, Crete Greece, Aug. 25-30, 2003. In this publication, a nonpermissive host, *B. mori*, was infected with two recombinant AcMNPVs. One encoded the piggybac transposase under the control of *Drosophila* heat shock protein 70 promoter and the other encoded the gene of interest (the one to be inserted into the *B. mori* genome) under the control of the *B. mori* actin A3 promoter and flanked by the piggyBac inverted terminal repeats. The design was that the transposase expressed by one virus mobilized the DNA in-between the inverted terminal repeats in the other and integrated that DNA into the host genome.

The presence of resident copies of the piggybac transposon in certain populations of *T. ni* does not appear to interfere with transposition of the transposon. Furthermore, the inventors have isolated a strain of *T. ni* which lacks resident copies of the piggyBac transposon. *T. ni* embryos have been injected with piggBac vectors, and transformants have been successfully recovered and characterized to confirm piggyBac mobilization into the genome.

For further guidance on the use of baculovirus-based vectors, see, e.g., WO01/29204 and U.S. Pat. No. 6,551,825 and U.S. Pat. No. 6,518,064. Other recent references that discuss piggyBac vectors and methods for generating transgenic insects using them include, e.g., Handler et al. (1998) *Proc Natl Acad Sci* 95, 7520-7525; Fraser, M. J (2001) The TTAA-specific family of transposable elements. In: *Insect transgenesis: Methods and Applications*. A. A. James and A. H. Handler, eds. CRC Press, Orlando, Fla.; Lobo et al. (1999) *Mol. Gen. Genetics* 261, 803-810; Grossman et cul. (2000) *Insect Biochem. Mol. Biol.* 30, 909-914; Lobo et al. (2001) *Mol Gen. Genom.* 265, 66-71; Lorenzen et al. (2003) *Insect Mol Biol.* 12, 433-40; Hacker et al. (2003) *Proc Natl Acad Sci USA*. 100, 7720-5; Sumitani et al. (2003) *Insect Biochem Mol Biol.* 33, 449-58; Horn et al. (2003) *Genetics* 163 647-61; and Tomita et al. (2003) *Nat Biotechnol.* 21, 52-6.

Methods for introducing constructs into an embryo to generate a transgenic insect (e.g., by microinjection) are conventional. Survivorship is usually quite high (up to 75%) for microinjected embryos. In general, preblastoderm eggs are stuck with a fine glass capillary holding a solution of the plasmid DNA and/or the recombinant virus. G0 larvae hatched from the virus-injected eggs are then screened for expression of the gene of interest. Breeding transgenic G1's with normal insects results in Mendelian inheritance. The inventors have succeeded in generating transformants using a piggybac transposon. See the Examples herein for a further discussion of such microinjection procedures.

Once a transgene(s) is stably integrated into the genome of an insect egg or early embryo, conventional methods can be used to generate a transgenic insect, in which the transgene(s) is present in all of the insect somatic and germ cells. When a subset of the complete set of glycosylation enzymes is present in a transgenic insect, other transposon-based vectors, which express different subsets of the glycosylation genes, can be introduced sequentially into the insect genome, and transgenic insects can then be generated. In another embodiment, when different subsets of the complete set of glycosylation enzymes are present in two or more individual transgenic insects, these insects can be genetically crossed to produce a transgenic insect that expresses a larger subset, or a complete set, of the glycosylation enzyme genes.

In some embodiments, the transgenic insects are heterozygous for the glycosylation enzyme genes. For example, when potentially toxic glycosylation enzymes are produced constitutively, it may be advantageous for the insects to be heterozygous, to limit the amount of the enzyme that is produced. In other embodiments, the insects are homozygous for the transgenes. Methods for producing homozygous transgenic insects (e.g., using suitable back-crosses) are conventional.

Another embodiment of the invention is an isolated cell, or progeny thereof, derived from a transgenic insect of the invention. Suitable cells include isolated germ line cells, and cells that can be used for the in vitro production of a polypeptide exhibiting a partial or complete pattern of mammalian glycosylation. Methods for obtaining and propagating cells from a transgenic insect, and using them (e g., to generate more insects, or to generate glycosylated proteins) are conventional.

The transgenic insects discussed above can be used to produce polypeptides of interest that exhibit partial or complete patterns of mammalian glycosylation. For example, the insects can be used in methods for glycosylating polypeptides in a mammalian (human) glycosylation pattern.

One embodiment of the invention is a method for producing, in an insect, a mammalianized (e.g., humanized) glycosylated form of a polypeptide of interest that is endogenous to the insect. The method comprises cultivating (culturing, rearing) a transgenic insect as discussed above (preferably in the form of a larva) under conditions effective to produce a mammalianized glycosylated form of said polypeptide of interest. Conditions for cultivating insects, such as insect larvae, are conventional. For example, insects expressing enzymes a), b), c), d), e) (a sialic acid synthase) and f) (CMP-sialic acid synthetase) are generally grown in the presence of the substrate (food), N-acetylmannosamine. If enzyme g) is also being produced by the insect, the substrate N-acetylglucosamine can be supplied, instead of N-acetylmannosamine.

Another embodiment of the invention is a method for producing, in an insect (preferably an insect larva), a mammalianized (e.g., humanized) glycosylated recombinant polypeptide. In embodiments of the invention, the recombinant polypeptide is an endogenous insect protein or, preferably, it is a heterologous protein. In one embodiment, this method comprises introducing into a transgenic insect as above (preferably in the form of a larva) a construct comprising nucleic acid encoding said recombinant protein, operably linked to an expression control sequence. In a preferred embodiment, these sequences are cloned into a suitable viral vector (such as a baculovirus-based vector, entomopox-based vector, or others). The coding sequences may be operably linked to an expression control sequence from the virus, itself, or to another suitable expression control sequence. Suitable virus-based vectors include, e.g., baculovirus vectors (such as vectors based on *Autographa californica* NPV, *Orgyia pseudotsugata* NPV, *Lymantria dispar* NPV, *Bombyx mori* NPV, *Rachoplusia ou* NPV, *Spodoptera exigua* NPV, *Heliothis zea* NPV, *Galleria mellonella* NPV, *Anagrapha falcifera* nucleopolyhedrovirus (AfNPV), *Trichoplusia ni* singlenuclepolyhedrovirus (TnSNPV)); retroviral vectors; and viral vectors that comprise transposon recognition sequences (e.g., piggyBac vectors); etc. As discussed above, baculovirus-based vectors have been generated that allow the cloning of large numbers of inserts, at any of a variety of cloning sites in the viral vector. Thus, more than one heterologous polypeptide may be introduced together into a transgenic insect of the invention. The viral vector can be introduced into an insect (e.g., an insect larva) by conventional methods, such as by oral ingestion.

In one embodiment, the baculovirus replicates until the host insect is killed. The insect lives long enough to produce large amounts of the glycosylated polypeptide of interest. In another embodiment, a baculovirus is used that is attenuated or non-permissive for the host. In this case, the host is not killed by replication of the baculovirus, itself (although the host may be damaged by the expression of the glycosylation enzymes and/or the heterologous protein of interest).

In another embodiment, sequences encoding one or more recombinant proteins of interest, operably linked to an expression control sequence, are cloned into a suitable transposon-based vector (such as a piggyBac vector). Like the baculovirus vectors discussed above, transposon-based vectors can carry large inserts, so more than one heterologous polypeptide may be introduced together into a transgenic insect of the invention. Transposon-based vectors may on occasion insert into the DNA of somatic cells, and thus be stably expressed for relatively long periods of time.

In another embodiment, sequences encoding one or more recombinant proteins of interest, operably linked to an expression control sequence, are cloned into a retrovirus vector, or any other suitable virus vector. Such a construct may insert into the DNA of somatic cells, and thus be stably expressed for relatively long periods of time.

Any heterologous polypeptide of interest may be expressed (and glycosylated) in an insect of the invention. A "heterologous"polypeptide", as used herein, refers to a polypeptide that is not naturally produced by the insect. The polypeptide may be of any suitable size, ranging from a small peptide (e.g., a peptide that contains an epitope that could be useful as a vaccine, or for generating an antibody of interest) to a full-length protein. The terms peptide, polypeptide and protein are used interchangeably herein. Preferably, the polypeptides expressed in this system are glycosylated in their natural mammalian (e.g., human) host. Suitable polypeptides include, e.g., marker proteins and therapeutic proteins.

Among the wide variety of heterologous proteins that can be produced are antibodies, cytokines, blood clotting factors, anticoagulants, viral antigens, enzymes, receptors, pharmaceuticals, vaccines (e.g., for viral or parasite infections), enzymes, hormones, viral insecticides, etc. More specifically, some representative examples of suitable heterologous proteins are human genes, including growth hormone (hGH), macrophage colony-stimulating factor (hM-CSF), beta-interferon (HuIFN-beta), alpha-interferon, interleukins, growth factors, including fibroblast growth factors, and CD4. Other suitable proteins include a surface polypeptide from a pathogen, such as a parasite or virus, which can be useful in a vaccine, e.g., a surface antigen of Plasmodium, a prolylendopeptidase from Flavobacterium, the fusion glycoprotein (F) from Newcastle disease virus (NDV), hepatitis B and C virus antigens, proteins from human T-cell leukemia virus type I, human papillomavirus type 6b E2 DNA binding gene product, influenza virus haemagglutinin, etc.

Other suitable proteins include therapeutic proteins which are currently produced recombinantly by other methods, and sold commercially, including antibodies and antibody fusion proteins [e.g., Campath (BCLL); Enbrel-RA (TNF inhibitor); Remicade-RA (TNF inhibitor); ReoPro (angioplasty); Rituxan (NHL); Synagis (RSV); Zenapax (transplant rejection); Zevalin (NHL); Herceptin (breast cancer); Humira (RA); MRA (RA); anti IL6 receptor (MAB); Xolair (asthma); Amevive (psoriasis); Bexxar (NHL); Antegren (Crohn's disease)]; lysosomal storage proteins [e.g., Cerezyme (Gaucher's disease); Aldurazyme-MPS-1 (Hurlers syndrome); Fabrazyme (Fabry disease)]; therapeutic enzymes [e.g., Epogen (anemia); activase (tissue plasminogen activator, thromobolysis)]; and others [including ABX-EGF (colorectal cancer); LymphoCIDE (NHL)]. See also U.S. Pat. Nos. 5,041,379 and 6,485,937.

The heterologous protein can also be a marker protein. The marker may be introduced by itself, or in conjunction with one or more other heterologous polypeptides. Such a marker may be used, e.g., to confirm that a construct is functioning as desired, to identify those larvae in which the heterologous construct is being expressed, etc. Suitable markers will be evident to the skilled worker and include, e.g., green fluorescent protein (GFP), DsRed, EYFP, ECFP, EVFP and derivatives of EGFP. See also the markers listed at the web site of BD Biosciences (Clontech).

A heterologous polypeptide can be expressed as an unfused polypeptide, a fusion polypeptide, a recombinant occlusion body, etc. If it is desirable to secrete a heterologous protein, a mammalian (e.g., human) signal peptide can be replaced with an insect signal sequence, e.g., an insect signal peptide from the insect cuticle gene or adipokinetic hormone, or prepromellitin protein, from baculovirus gp64 or egt proteins, or others.

Methods for introducing constructs of the invention into insects, such as a transgenic insect of the invention, are conventional. See U.S. Pat. No. 5,593,669 and Example XIV for some typical methods. A skilled worker will recognize appropriate times (a time window) during insect propagation in which such super-infection is possible. In some embodiments, the super-infection results in transient expression of the recombinant gene. In other embodiments, the recombinant gene is stably introduced into a somatic cell of the insect.

The method for producing a mammalianized heterologous polypeptide of interest may further comprise culturing the insect under conditions effective for expressing the heterologous protein and for glycosylating it in a mammalianized (humanized) fashion. The method may further comprise harvesting the mammalianized (humanized) glycosylated heterologous polypeptide. Methods for cultivating and/or breeding the insects are conventional. In some cases, for example when detrimental products, such as certain glycosylating enzymes, are being produced in an insect, specialized cultivating methods may be employed. Some methods for cultivating insects are discussed in U.S. Pat. No. 6,153,409 and in the Examples. Methods for harvesting and, if desired, purifying the heterologous protein, are conventional.

One embodiment of the invention is a transgenic insect of the invention that is infected with a vector (such as a baculovirus-based vector, a transposon-based vector, or a retrovirus vector) that encodes a heterologous polypeptide of interest, operably linked to an expression control sequence. Another embodiment is a transgenic insect of the invention that expresses one or more glycosylation enzymes as discussed herein that allow for the production of a partially or completely mammalianized glycosylated polypeptide in the insect. Another embodiment is a transgenic insect of the invention that expresses such glycosylation enzymes, and that is infected with a vector that encodes a heterologous polypeptide of interest, operably linked to an expression control sequence.

Another method for producing, in an insect, one or more heterologous mammalianized (e.g., humanized) glycosylated polypeptides of interest, comprises using a multiply transgenic insect, which is a transgenic insect as above (whose somatic and germ cells contain genomically integrated nucleic acids encoding glycosylation enzymes), whose somatic and germ cells further comprise genomically integrated recombinant nucleic acid encoding said heterologous polypeptide(s) of interest, operably linked to an expression control sequence. Although the polypeptide of interest may be expressed in a multiply transgenic insect as above, it is still considered to be "heterologous" to the insect.

Methods to generate such multiple transgenic insects are conventional. For example, one can start with an insect that is transgenic for a set of glycosylation enzymes, and then insert into the host genome a transgene that expresses a heterologous polypeptide of interest. Alternatively, one can begin with an insect that is transgenic for a polypeptide of interest (such as collagen, IFN, etc), and then introduce into the host genome DNA encoding a set of glycosylating enzymes. Genetic crosses and/or sequential introduction of suitable constructs may be employed to generate a multiply transgenic insect. A multiply transgenic insect as above can be cultivated, and the glycosylated heterologous polypeptides made therein can be harvested, using conventional procedures.

This aspect of the invention thus relates both to multiple transgenic insects as above, and to methods of using the insects to produce heterologous glycosylated polypeptides.

In some embodiments of the invention, the glycosylation genes in a transgenic insect are under the control of, or "operably linked to" a regulatable control system. Suitable regulatable control systems, which will be evident to the skilled worker, include the inducible expression promoters/enhancers discussed elsewhere herein, such as hsp70, or a Tet-based inducible system, used in conjunction with any suitable constitutive promoter (e.g., the Tet-CMV IE or the Tet-baculovirus iel systems). The use of regulatable control sequences can allow for the glycosylation enzymes to be expressed at low levels, or not to be expressed, until the polypeptide of interest begins to be expressed. "Low levels" refers to levels that are too low to achieve partially or fully mammalianized (e.g., humanized) polypeptides, and/or levels that are not toxic to the host.

In one embodiment, the inducible promoter is a baculovirus-specific promoter. For example, a transgenic insect (preferably a larva) of the invention may comprise a set of glycosylation genes that are under the control of one or more late or very late baculovirus promoters. When the insect is propagated, little if any expression of the glycosylation genes occurs. However, following infection of the insect with a baculovirus vector containing a heterologous gene of interest, the baculovirus infection induces expression of the glycosylation genes, so that the heterologous polypeptide of interest which is expressed from the baculovirus vector is glycosylated as it is produced. This insures that potentially toxic glycosylation enzymes are expressed only, at a significant level, or primarily, during the period during which the enzymatic activity is required.

Similarly, a multiply transgenic insect that comprises genomically integrated copies of both glycosylation enzymes and heterologous polypeptides of interest can be designed such that the polypeptide of interest and the glycosylation enzymes are expressed at suitable levels, at the desired time during insect growth, by selecting appropriate expression control sequences for each of the genes. A skilled worker can readily design suitable constructs, using, e.g., suitable combinations of inducible promoters, constitutive promoters, promoters expressed at different times (temporally regulated) during baculovirus infection, etc.

Another method for producing, in an insect, one or more heterologous mammalianized (e.g., humanized) glycosylated polypeptides of interest, does not involve using transgenic insects. Rather, in this aspect of the invention, an insect (preferably an insect larva) is infected with one or more vectors (preferably viral vectors) that comprise nucleic acid sequences encoding a recombinant polypeptide of interest and/or one or more glycosylation enzymes. The sequences encoding both the polypeptide(s) of interest and the glycosylation enzyme(s) are operably linked to expression control sequences. Any of the combinations of glycosylation enzymes discussed above may be introduced into the insect; and any of the expression control sequences, including regulatable promoters, may be used. A skilled worker will recognize what types of expression control sequences and what combinations of glycosylation enzymes are suitable.

Any of a variety of vectors may be used. Preferably, the vector is a baculovirus-based vector, such as those described elsewhere herein. As noted, such vectors can carry large numbers of large inserts. Thus, a partial or complete set of glycosylating enzymes can be introduced into the insect on a single vector, ensuring that the entire set of enzymes will be expressed in a given cell. In some embodiments, the heterologous polypeptide of interest is encoded on the same vector as the glycosylation enzymes; in other embodiments, it is carried on a separate vector. One, two, or even more baculovirus-based vectors may be introduced into an insect. The vectors may be introduced simultaneously, or sequentially, provided that they are introduced within the allotted time window. In another embodiment, the glycosylating enzyme and polypeptide of interest sequences are cloned into one of the transposon-based vectors described elsewhere herein, such as a piggyback vector, or into a retrovirus vector, and used to infect an insect.

One embodiment of the invention is an insect comprising, in at least some of its cells, glycosylation enzymes as described above that allow the production of partially or completely mammalianized glycoproteins of interest in the insect, and a heterologous polypeptide. Another embodiment is an insect comprising, in at least some of its cells, an expressible recombinant nucleic acid encoding a polypeptide of interest, and expressible nucleic acid encoding glycosylation enzymes as described above that allow the production of partially or completely mammalianized glycoproteins of interest in the insect.

Another embodiment is a method for producing, in an insect larva, a partially or completely mammalianized glycosylated polypeptide of interest that is heterologous to the insect, comprising introducing a vector comprising nucleic acid encoding said heterologous polypeptide, operably linked to an expression control sequence, into a transgenic insect larva, or progeny thereof, whose somatic and germ cells contain recombinant nucleic acid encoding one or more (e.g., two or more) of the glycosylation enzymes:

a) beta-1,2-N-acetylglucosaminyltransferase I,
    b) beta-1,2-N-acetylglucosaminyltransferase II,
    c) a β1,4-galactosyltransferase, and/or
    d) a sialyltransferase,
wherein each recombinant nucleic acid encoding a glycosylation enzyme is integrated in the insect genome, and is present in one or more copies, wherein each recombinant nucleic acid encoding a glycosylation enzyme is operably linked to an expression control sequence, wherein expression of said glycosylation enzymes allows for production of a partially or completely mammalianized glycosylated protein in the insect, and wherein if the insect (particularly if it is *B. mori*) contains genomically integrated nucleic acid encoding enzyme c), then the insect also contains genomically integrated nucleic acid encoding at least one of enzymes a), b) or d).

Another embodiment is a method for producing, in an insect larva, a partially or completely mammalianized glycosylated polypeptide of interest that is heterologous to the insect, comprising introducing a vector comprising nucleic acid encoding said heterologous polypeptide, operably linked to an expression control sequence, into a transgenic insect larva, or progeny thereof, whose somatic and germ cells contain recombinant nucleic acid encoding one or more (e.g., two or more) of the glycosylation enzymes:

a) beta-1,2-N-acetylglucosaminyltransferase I,
b) beta-1,2-N-acetylglucosaminyltransferase II,
c) a β1,4-galactosyltransferase, and/or
d) a sialyltransferase, wherein each recombinant nucleic acid encoding a glycosylation enzyme is integrated in the insect genome, and is present in one or more copies, wherein each recombinant nucleic acid encoding a glycosylation enzyme is operably linked to an expression control sequence, wherein expression of said glycosylation enzymes allows for production of a partially or completely mammalianized glycosylated protein in the insect, and wherein, if the insect is *B. mori*, the glycosylated polypeptide is not expressed in a tissue-specific manner (e.g., is not expressed specifically in the silk glands).

Another embodiment is a library of transgenic insects of the invention (TRANSPILLAR larvae or other forms of the insect) expressing a variety (e.g., more than one, preferably at least about 50 different glycosylated proteins. Preferably, each member of such a library comprises, in its somatic and germ cells, expressible sequences encoding both a suite of glycosylation enzymes and one or polypeptides of interest (which are designated to become glycosylated in a mammalianized fashion). In a preferred embodiment, the sequences encoding the glycosylation enzymes are under the control of a regulatable expression control sequence, so the insect can be maintained without expressing the glycosylation enzymes (which are potentially toxic to the cells), and the glycosylation enzymes are not turned on until they are needed in order to glycosylate the polypeptide of interest.

Another embodiment is a library of transgenic insects of the invention (TRANSPILLAR larvae or other forms of the insect) that can be used to glycosylate proteins in a variety of partial or complete glycosylation patterns. Any of the suites of glycosylation enzymes discussed elsewhere herein can be used. The number of suitable permutations of glycosylation enzymes can range between about one and abut 400. Preferably, at least one of the insects expresses a full complement of glycosylation enzymes, including, e.g., beta-1,2-N-acetylglucosaminyl-transferase II; a β1,4-galactosyltransferase; an alpha 2,6-sialyltransferase; an alpha 2,3-sialyltransferase; a sialic acid synthase; and CMP-sialic acid synthetase (and, optionally, beta-1,2-N-acetylglucosaminyltransferase I). As was the case for the library discussed above, the sequences encoding the glycosylation enzymes are preferably under the control of a regulatable expression control sequence, so the insect can be maintained without expressing the glycosylation enzymes (which are potentially toxic to the cells), and the glycosylation enzymes are not turned on until they are needed in order to glycosylate a polypeptide of interest. For example, the glycosylation enzymes can be placed under the control of one or more late baculovirus promoters, and expression of the glycosylation enzymes can be turned on by infecting such an insect larva with a baculovirus that encodes an expressible polypeptide of interest, which is destined to become glycosylated in a mammalianized fashion.

Another embodiment is a method for producing, in an insect larva, a partially or completely mammalianized glycosylated polypeptide of interest that is endogenous or heterologous to an insect as described herein, or an insect as described herein, wherein the insect is not *Bombyx mori* In the foregoing and in the following examples, all temperatures are set forth in uncorrected degrees Celsius; and, unless otherwise indicated, all parts and percentages are by weight.

The following examples are provided to illustrate certain embodiments of the invention. They are not intended to limit the invention in any way.

EXAMPLES

Example I

General Overview of One Aspect of the Invention

A colony of lepidopteran insect larvae (*Trichoplusia ni*) is stably transformed with a set of genes important for mammalianizing (e.g., humanizing) their protein N-glycosylation pathways. The piggybac system is used in a series of consecutive transpositional events to translocate a set of about 2-8 or more glycosylation genes (preferably a set of about 6-8 glycosylation genes) into the germline of insect embryos. Stable incorporation of these genes results in mammalianization (humanization) of all endogenous glycoproteins. One indication that these genetic modifications are not lethal to these insects is that that the N-glycosylation pathway has been humanized in cultured insect cell lines with no obvious deleterious effects. The risk of such detrimental effects occurring is further assessed by transforming *Drosophila melanogaster*. This model system is amenable to more rapid experiments than is the *T. ni* system. In some experiments, a molecular regulator of expression, the tetracycline repressor, is incorporated into the design for lepidopteran transformations. This design precludes transgene expression until the insects are infected with the baculovirus vector. Transgene expression is switched off until the late phase of infection, when the insects have already been effectively converted to bioreactors for recombinant glycoprotein production and are doomed to die as a result of the viral infection, anyway.

Modular piggyBac expression vector cassettes encoding various mammalian enzymes involved in glycoprotein processing are constructed. These constructs are tested for their ability to induce enzymatic activity during transient transfection of cultured insect cells. Subsequently, these piggybac vectors are used to transform *D. melanogaster* and the overall physiological influence of mammalian glycoprotein processing enzyme expression is examined in these insects. If there are no adverse effects, the piggyBac vectors are used to transform the lepidopteran host, *T. ni*. Alternatively, new constructs designed for regulated or tissue specific (e.g., silk gland) expression of the mammalian genes are constructed, tested, and used to transform other insect species, as described above. After the transgenic insect lines are established, their N-glycosylation capabilities are examined using a model recombinant glycoprotein expressed during baculovirus infection. Subsequently, glycosylation of a biotechnologically relevant recombinant glycoprotein is examined using this virus-host system.

Example II

Experiments in Insect Cell OLines

Aspects of the invention can be carried out by adapting methods used in insect cell culture. See for example, U.S. Pat. No. 6,461,863. Insect cell lines were genetically transformed to create improved hosts for the production of humanized recombinant glycoproteins by baculovirus vectors. Sf9 cells were transformed with an expression plasmid encoding the cDNA for a mammalian beta4Gal-TI to create a transgenic insect cell line called Sfβ4GalT (Hollister et al. (1998) *Glycobiology* 8, 473-80). The B4Gal-TI cDNA was placed under the control of the promoter from a baculovirus immediate early gene called iel, which provides constitutive foreign gene expression in lepidopteran insect cells. Sfβ4GalT cells grew normally, supported baculovirus replication, and constitutively expressed the mammalian β4Gal-TI gene. In addition, unlike the parental Sf9 cells, Sfβ4GalT cells were able to produce terminally galactosylated recombinant glycoproteins, such as human tissue plasminogen activator, when infected with baculovirus expression vectors. An iel expression plasmid encoding a mammalian alpha 2,6-Sial-T (ST6GalI) was used to super-transform Sfβ4GalT cells and produce another transgenic cell line, Sfβ4GalT/ST6. This new cell line encoded and expressed both β4Gal-TI and ST6GalI, grew normally, and supported baculovirus replication (Hollister et al. (2001) *Glycobiology* 11, 1-9). In addition, this cell line could produce terminally sialylated recombinant N-glycoproteins during baculovirus infection. Two analogous transgenic High Five® derivatives, Tnβ4GalT and Tnβ4GalT/ST6, also had the same capabilities as the corresponding Sf9 derivatives (Breitbach et al. (2001) *Biotech. Bioengr.* 74, 230-9).

The major processed N-glycans produced by these cells are monoantennary structures in which only the lower branch, not the upper, is elongated. These results suggested that these cell lines lacked sufficient levels of endogenous GlcNAc-TII activity to initiate elongation of the upper branch, which is necessary to produce conventional biantennary N-glycans (FIG. 1). A new transgenic cell line, designated SfSWT-1, was prepared by transforming Sf9 cells with five different mammalian glycosyltransferase genes, including GlcNAc-TI, GlcNAc-TII, β4Gal-TI, ST6GalI, and alpha-2,3-Sial-T (ST3GalIV). SfSWT-1 cells encode and express all five transgenes under iel control, have normal growth properties, and support baculovirus replication. In addition, these cells can produce biantennary, terminally sialylated N-glycans identical to those produced by mammalian cells. See, e.g., Hollister et al. (2002) *Biochemistry* 41, 15093.

Sfβ4GalT/ST6 and SfSWT-1 cells can also produce sialylated N-glycans even though these cells have no detectable CMP-sialic acid, which is required as the donor substrate for ST6GalI and ST3GalIV. Subsequent experiments showed that both transgenic cell lines require either fetal bovine serum or a purified sialylated glycoprotein in order to produce sialylated glycoproteins (Hollister et al. (2003) *Glycobiology* 13, 487-495). Without wishing to be bound be any particular mechanism, it is suggested that terminal sialic acids from these exogenous sources are probably recycled for incorporation into newly synthesized glycoproteins, an interpretation that is consistent with known mechanisms for sialic acid uptake and reutilization in mammalian cells. However, insect cells were further engineered for de novo CMP-sialic acid production to circumvent the need for an exogenous sialic acid donor (Aumiller et al. (2003) *Glycobiology* 13, 497-507).

Example III

Selecting Mammalian Processing Genes

From the results of a comparative analysis of the mammalian and insect protein N-glycosylation pathways, we incorporate mammalian glycosylation enzyme genes, including GlcNAc-TII, β4Gal-TI, ST6GalI, ST3GalIV, sialic acid synthase (SAS), and/or CMP-sialic acid synthetase (CMP-SAS) genes, into an insect genome to compensate for the lack of these enzymes in insect larvae. GlcNAc-TII initiates elongation of the upper branch, which is necessary to convert N-glycan intermediates to conventional biantennary structures. β4Gal-TI, ST6GalI, and ST3GalIV complete the elongation and terminal sialylation of N-glycans. Both sialyltransferase genes are incorporated because ST6GalI and ST3GalIV transfer sialic acids in alpha-2,6- or alpha-2,3-linkages, respectively, and some human N-glycoproteins have one linkage, some have the other, and some have both. Since transgenic larvae may not be able to scavenge sialic acid, the SAS and CMP-SAS genes are included to ensure a conventional source of CMP-sialic acid. SAS and CMP-SAS convert N-acetylmannosamine, a monosaccharide precursor that can be incorporated into the larval diet, to CMP-sialic acid.

Addition of these transgenically engineered mammalian genes enables transgenic insect larvae to produce complex, terminally sialylated N-glycans. To counteract the possibility that the insects used have too little GlcNAc-TI or too much GlcNAcase activity to efficiently elongate the lower branch of N-glycan intermediates (see FIG. 1), or that the insects lack the transporter needed to move CMP-sialic acid into the Golgi apparatus, additional mammalian genes encoding GlcNAc-TI or a CMP-sialic acid transporter into the transgenic insects are incorporated as deemed necessary. Increasing the level of GlcNAc-TI activity effectively is expected to counteract the negative effect of the GlcNAcase on N-glycan processing, as previously demonstrated in insect cell lines. Down-regulation of GlcNAcase gene expression by RNAi based methods for example, is also used. Additional genes are incorporated into transgenic insects by either super-transformation or cross-breeding.

Example IV

Selecting Expression Control Sequences

The baculovirus iel promoter/hr5 enhancer (iel/hr5) combination is chosen for constitutive foreign gene expression. An advantage of using this combination is that baculovirus infection induces the expression of integrated transgenes under iel/hr5 control, which increases the levels of the enzymes needed for glycoprotein processing prior to the time the glycoprotein of interest is expressed.

The Tet-mediated expression system provides regulatable gene expression when linked to the cytomegalovirus minimal promoter (CMV). This system works effectively in insect systems. In addition, using the appropriate Tet repressor mutation, either repression or induction of gene expression, may be achieved upon exposure to tetracycline or doxycycline. We utilize the TetO and CMV promoter sequences to achieve controlled expression of the mammalian glycoprotein processing enzymes in the insect larvae and test the utility of the Tet expression system for controlled expression from the ie-1/hr5 baculovirus immediate early promoter.

Example V

Selecting a Model Recombinant Glycoprotein

The transgenic insect's ability to process recombinant glycoproteins during baculovirus infection is determined using GST-SfManI as a model. GST-SfManI is a glutathione-S-transferase (GST)-tagged, secreted form of an endogenous class I Sf9 cell alpha-mannosidase. This hybrid protein is well characterized and has been used as a model in previous studies of N-glycan processing in native and transformed insect cell lines. GST-SfManI allows us to progress relatively quickly through an analysis of the glycoprotein processing capabilities of our transgenic insects.

Example VI

Preparation and Testing of Constructs for Transformation of Insects

A. piggybac vectors. The piggyBac element has a demonstrated capacity of at least 9.5 kb of inserted DNA, with an overall transposon size of 9.9 kb. Insertions up to 10 kb, with an overall size of 10.5 kb for the element, can be mobilized at normal frequencies. Gene expression vectors for transformation of D. melanogaster and T. ni are constructed using a cassette approach that allows us to insert different promoter regions between pairs of genes for analysis of expression in our insect systems as described in Shi et al, 2007, BMC Biotechnology 7:5. Each gene is individually PCR amplified to allow positioning of appropriate restriction enzyme sites on either side of the gene. The amplified products are cloned and sequenced to insure integrity. Each gene pair is then assembled from the individual amplified genes in a plasmid clone. The use of different restriction sites at the termini of each gene insures directional cloning of that gene in the plasmid. For example, gene pairs as indicated below can be designed to progressively extend the insect N-glycosylation pathway (FIG. 1). Other gene pairs can also be used, examples of which will be evident to the skilled worker.

Each gene pair is tagged with a different fluorescent reporter gene for transformation. For this purpose we utilize the 3XP3 promoter driving expression of the DsRed, ECFP, and EYFP genes. The 3XP3 promoter is active in nerve tissues, principally the eye of the insect. Visualization of the GFP markers is possible not only in white-eye mutants, but also in pigmented eye wild type insects. Since there is no available white-eye mutant strain in the target insect, T. ni, this promoter is very useful in screening our transgenic lepidopterans. The three fluorescent protein markers chosen are distinguishable from each other using the appropriate wavelength filter, permitting the monitoring of multiple transformations in a single insect.

The following scheme was employed to engineer the plasmids shown in FIG. 4. Steps for assembling the intermediate elements of these constructs, such as gene pair cassettes, cassettes with the marker protein, etc. were conventional. Primers used to amplify sub-portions of the constructs were generated based on known sequences, which are readily available to the skilled worker: Convenient restriction enzyme recognition sites were added during PCR amplification and used to insert the PCR products into recipient plasmids. Some of these restriction sites are indicated in the structures shown in FIG. 4.

1. Amplified HR5-IE1 element and cloned into TOPO to make pHr5IE1R.TOPO.1.
2. Amplified IE1 promoter and cloned into TOPO to make pIE1L.TOPO.1.
3. Excised IE1L from pIELTOPO.1, subcloned into pHr5IE1R.TOPO.1 to make pDIE1.TOPO. 1.
4. Deleted XbaI site in pDIE1.TOPO.1 to make pDIE1.TOPO. 2.
5. Amplified BGH poly A signal, cloned into TOPO to make pBGHPolyA.TOPO. 1.
6. Excised BGH poly A, cloned into pDIE1.TOPO.2 to create pDIE1.TOPO. 3.
7. Amplified 3XP3 promoter, cloned into TOPO to make p3xP3.TOPO. 1.
8. Subcloned BGH poly A signal from pBGHPolyA. TOPO.1 into p3xP3.TOPO. 1 to make p3xP3. TOPO. 2.
9. Amplified DSRed marker, cloned into TOPO to make pDSRed. TOPO. 1.
10. Excised DSRed from pDSRed. TOPO.1, subcloned into p3xP3. TOPO. 2 to make p3xP3DSRed. TOPO. 2.
11. Amplified ECFP marker, cloned into TOPO to make pECFP. TOPO. 1.
12. Excised ECFP marker from pECFP. TOPO.1, subcloned into p3xP3. TOP0.2 to make p3xP3ECFP. TOPO. 2.
13. Amplified EYFP marker, cloned into TOPO to make pEYFP. TOPO. 1.
14. Excised EYFP marker from pEYFP. TOPO. 1, subcloned into p3xP3. TOPO. 2 to make p3xP3EYFP. TOPO. 2.
15. Excised 3xP3DSRed, 3xP3ECFP, and 3xP3EYFP cassettes from p3xP3DSRed. TOPO. 2, p3xP3ECFP. TOPO. 2, and p3xP3EYFP. TOPO. 2, respectively. Subcloned each into pDIE1-TOPO. 3 to create pDIE. DSRed. TOPO. 3, pDIE. ECFP. TOPO. 3, and pDIE. EYFP. TOPO. 3, respectively.
16. Excised BGH Poly A from pBGH. PolyA.TOPO. 1, subcloned into pDIE. DSRed.TOPO. 3, pDIE.ECFP.TOPO. 3, and pDIE. EYFP.TOPO. 3 to create pDIE DSRed. TOPO.4, pDIE.ECFP.TOPO. 4, and pDIE.EYFP. TOPO. 4, respectively.
17. Amplified human GlcNAc-TII, bovine B4GalT, rat ST6GalI, mouse ST3GalIII, mouse SAS, and mouse CMP-SAS, cloned each individual amplimer into TOPO (yielded 6 individual TOPO subclones).
18. Excised human GlcNAc-TII and bovine 134GalT from TOPO clones, subcloned into pDIE. DSRed. TOPO. 4 to create pDIE. GnTII/GalT. DSRed. TOPO. 4.
19. Excised rat ST6GalI and mouse ST3GalHI from TOPO clones, subcloned into pDIE. ECFP. TOPO. 4 to create pDIE. ST6.1/ST3. 4. ECFP. TOPO. 4.
20. Excised mouse SAS, and mouse CMP-SAS from TOPO clones, subcloned into pDIE. EYFP. TOPO. 4 to create pDIE. SAS/CMP. SAS. EYFP. TOPO. 4.
21. Excised each DIE. enzymel/enzyme2. eye marker cassette from the TOPO. 4 clones listed in item #20 and subcloned into the piggybac vector, pXLBac-2, in-between the transposition elements in that vector.

This set of steps resulted in the creation of the three plasmids shown in FIG. 4, each encoding two "glycosylation enzymes" under hr5IE1 control and a marker gene under 3XP3 control.

In a variation of the above method, the bivalent promoter cassettes are excised and replaced with similar cassettes containing alternate control elements, examples of which will be evident to the skilled worker. For example, the hr5IE1 promoter cassette noted above can be replaced with cassettes such as the following (bounded by appropriate restriction enzyme sites):
←hsp70-hr5-hsp70→
←CMV-7xTetO-CMV→
←iel/hr5-7xTetO-iel/hr5→
←p25-X-p25→(wherein X can be an intervening or spacer sequence, a regulatory element or an enhancer)

The three plasmids shown in FIG. 4 are used to create transgenic larvae in conjunction with a plasmid encoding the piggybac transposase.

B. Testing piggybac vectors in vitro. Each constructed piggyBac vector is rapidly tested for its ability to express the relevant mammalian genes under control of the iel/hr5 promoter by transient transfection assays in insect cell lines. Briefly, Sf9 cell cultures are individually transfected with various piggybac vectors encoding the glycosyltransferases or with the empty promoter cassette vectors as negative controls. Immediate early expression plasmids encoding GlcNAc-TII, β4Gal-TI, ST6GalI, or ST3GalIV are available and are used as positive controls. The cells are lysed at 24 h post-transfection and lysates are used for conventional glycosyltransferase assays. Three of these assays have been previously described in detail (Hollister et al. (2001) *Glycobiology* 11, 1-9; Hollister et al. (2002) *Biochemistry* 41, 15093-15104).

A different type of transient expression assay is needed to test the piggybac vectors encoding SAS and CMP-SAS, which are the enzymes involved in sialic acid biosynthesis (See Shi et al., 2007, supra). In these assays, Sfβ4GalT/ST6 cells are transiently transfected with the construct encoding SAS and CMP-SAS, then, 24 h later, the cells are stained with a fluorochrome-conjugated lectin, *Sambucus nigra agglutinin* (SNA), which is specific for terminal alpha 2,6-linked sialic acids. Sfβ4GalT/ST6 cells cannot produce sialylated N-glycoproteins when cultured in serum-free media. If the piggyBac vector encoding SAS and CMP-SAS is functional, it induces Sfβ4GalT/ST6 cells to produce sialylated N-glycoproteins even when cultured in serum-free medium containing N-acetylmannosamine, and the transfected cells are stained with SNA. One negative control for this assay is Sfβ4GalT/ST6 cells transfected with the empty promoter cassette vector and cultured in serum-free medium containing N-acetylmannosamine. Another negative control is to transform these cells with the piggyBac vector encoding SAS and CMP-SAS, but cultured in serum-free medium lacking N-acetylmannosamine. The positive controls are Sfβ4GalT/ST6 cells transfected with the empty promoter cassette and cultured in serum-free medium supplemented with fetuin, which supports N-glycoprotein sialylation by these cells.

piggyBac vectors comprising the constructs shown in FIG. 4 were tested for transient transfection in Sf9 cells in culture. (See Shi et al., 2007, supra). In the final step of constructing piggyBac-based vectors for inserting glycosyltransferase genes into insects or insect cells, the restriction fragments carrying the glycosyltransferase genes (two genes per fragment) and the fluorescent protein marker gene were inserted into the piggyBac plasmid pXLBacII in two different orientations with respect to the piggyBac terminal repeat sequences (TR-L/IR-L and TR—R/IR—R). Hence, for each set of glycosyltransferase genes, two different piggybac vectors were constructed, with the glycosyltransferase genes and the fluorescent protein marker in opposite orientations. The piggyBac vectors were tested to measure the activity of the glycosyltransferase genes. Unexpectedly, it was found that, for each individual glycosyltransferase gene, the vector in which the gene was oriented so that it pointed towards the left-hand piggyBac terminal repeat (TR-L/IR-L) produced significantly more glycosyltransferase activity for that particular gene than the piggybac vector in which the same gene was pointing towards the right-hand terminal repeat (TR—R/IR—R). The glycosyltransferase activity levels for the piggyBac plasmids were also higher than those found with non-piggyBac plasmids carrying the same genes.

Example VII

Testing Transformation Efficiency and the Effect of Transgene Expression in the Model Insect System, *Drosophila melanogaster*

The addition of mammalian processing enzymes extensively modifies the N-glycosylation profile of endogenous proteins in the insect. N-glycans can directly or indirectly influence protein functions in many different ways. To assess whether alterations of endogenous N-glycoproteins resulting from our genetic manipulations are phenotypically acceptable, the expression of the mammalian enzymes is studied in a model insect system. *D. melanogaster* is used as the model insect system for transformation experiments, since it can be efficiently transformed with piggyBac, easily handled, rapidly manipulated, and easily screened for transformation.

An experimental protocol is used to determine whether or not the hr5-IEI promoted, constitutively expressed glycosylation enzyme transposon vectors cause detrimental effects upon expression in transgenic insects. Since severe detrimental effects may result in difficulties detecting transformations at all, we use a co-transformation strategy that is more likely to produce interpretable results than single plasmid transformation attempts.

The injections are performed simultaneously with and without a control piggybac vector expressing a complementary fluorescent eye color gene. This allows us to determine whether the glycosylation plasmids are capable of generating viable transformants. If viable transformants are not found, then we can at least be assured that our transformation experiments are performed correctly and that the glycosylation plasmids themselves are detrimental. In this case, other procedures, such as the use of regulated expression control sequences, are used.

A variety of types of regulatable expression of glycosylation genes are employed. For example, insects transformed with a construct under the control of a regulatable expression control sequence, such as a TetO/CMV—IE construct, are directly compared under repressed and induced conditions in this system, allowing a well-controlled assessment of the effect of gene expression on the insect. The TetO/CMV promoter construct system is useful, at least because this system is already developed in *Drosophila*, and appropriate repressor strains are available. A rtTetR-MT strain is available for these transformations, which produces a mutant version of the Tet repressor protein that acts as an inducer of TetO/CMV expression when flies are fed on media containing tetracycline or doxycycline. Alternatively, a native Tet repressor transformed *Drosophila* strain is used for the transformations; this permits suppression of the CMV promoter activity in the presence of tetracycline or doxycycline. In either case, induction or de-repression of gene expression is examined at various times throughout the life cycle of the transformed insects to determine what effect expression of mammalian glycosylation enzymes has on the insect.

RT-PCR assays are performed on extracts following induction of expression to confirm expression and determine rates of accumulation of transcripts for the transgenes. Glycosylation is assessed using glycosyltransferase assays as described elsewhere herein. If there is no noticeable effect on the transgenic insects with each of the individual constructs, mating and selection are performed to produce lines having two, and then three constructs, and similar analyses of toxicity and expression levels are performed. Alternatively, manipulations in lepidopteran insects include inducible promoters that can be activated upon infection with a baculovirus vector.

Several outcomes of the introduction of mammalian glycosylation pathways are evaluated in this tractable model system. Possible undesirable outcomes that are tested for include, e.g., developmental abnormalities, sterility, incomplete or abnormal embryonic development. In other tests, lethality at any stage is evaluated following heat shock, or through crosses with appropriate Drosophila rTA repressor/activator strains, respectively.

The pXLBacII-SAS/CMP. SAS-EYFP plasmid (the clone #42-3 plasmid) was tested by co-injecting 1052 Drosophila embryos with pXLBacII-SAS/CMP. SAS-EYFP and the pCaSpeR-hs-orf helper plasmid A total of 396 hatched larvae (37.6%) and 100 Adults (51 males and 49 males) were recovered to establish crosses with wild type individuals. Of these, 1 family expressed the yellow fluorescence expected for this construct, verifying that these two enzymes are not toxic when expressed in transgenic insects. In another experiment to confirm these findings, 2038 embryos were injected, again using pXLBacII-SAS/CMP. SAS-EYFP, pBSII ITR1. 1K ECFP and pCaSpeR-hs-of helper plasmid. These embryos are studied as above.

A co-injection experiment was also performed on 982 embryos using the control plasmid pBSII ITR1. 1K ECFP in addition to the pXLBacII-SAS/CMP. SAS-EYFP and the helper plasmid. We recovered 195 hatched larvae (19.8%) and 54 Adults (18 males and 36 males), with one family expressing the cyan fluorescence marker of the pBSII ITR 1.1K ECFP control plasmid.

To evaluate two other sets of constructs:

A) The pXLBacII-ST6. 1/ST3.3M-CFP plasmid (e.g., the clone #21-1 plasmid) is tested by co-injecting the plasmid into Drosophila embryos along with the pCaSpeR-hs-orf helper plasmid. From these injected embryos, larvae are hatched, with some surviving to adulthood. Each of these surviving adults is mated to a wild type individual to produce crosses which are screened for fluorescent eye transformants. Further embryos are also injected and studied as above, to confirm the findings from the first set of injections. For example, injections may include drosophila embryos co-injected with the pXLBacII-ST6.1/ST3. 3M-CFP, the internal control plasmid pBSII ITR1. 1K-EYFP, and the pCaSpeR-hs-orf helper plasmid.

B.) The pXLBacII-GnTII/GalT-DsRed plasmid (e.g., clone #57) is injected along with the helper plasmid into embryos. In one experiment, 1184 embryos, with 272 larvae (22.9%) hatched and 62 Adults (28 males and 34 males) recovered for mating with wild type individuals. Further analysis is performed as above.

For each set of injections, control injections are performed using the pBSII ITR 1.1K ECFP plasmid and the pCaSpeR-hs-orf helper. For example, in one experiment 562 drosophila embryos were injected, 199 larvae (35.4%) hatched and 53 Adults (all males) were recovered and mated. The lack of any female survivors was rather unusual, but attributed to chance. In this case three families expressing the yellow fluorescence were obtained.

In additional studies we drove N-glycosylation toward increased complexity and examined the functional consequences of the resulting shift in N-glycan complexity in Drosophila melanogaster. We constructed three dual piggyback transformation vectors, each encoding a pair of mammalian enzymes: N-acetylglucosaminyltransferase II (GlcNAcT-II) and β4-galactosyltransferase I (GalT); α2,6- and α2,3-sialyltransferases; sialic acid synthase and CMP-sialic acid synthetase. Transformants were obtained with vectors encoding the sialyltransferases or sialic acid synthase and CMP-sialic acid synthetase under the control of constitutive promoters, but not with the vector encoding GlcNAcT-II and GalT under the control of the same promoter. Replacing the constitutive promoter in the latter vector with an inducible promoter made transformation possible, suggesting that constitutive over-production of complex N-glycans is inconsistent with Drosophila viability or fertility. Finally, the three transformed fly strains were crossed to create a strain carrying all six mammalian genes. RT-PCR analysis verified the GlcNAcT-II and GalT genes were inducibly and the other four mammalian genes were constitutively expressed. Glycomic characterization of whole larvae revealed significant increases in sialylated, complex N-glycans (up to 10-fold for some structures) following transgene induction. However, paucimannose N-glycans were still prominent.

Glco6 genotype: w;25.2+10.2+57.1/Cy; 24(1)3+TAM2.2/UbX 25.2=pXLBacII-SAS-CMP.SAS#25(EYFP), 10.2=pXLBacII-ST6.1-ST3.3M#10 (ECFP), 24(1)3=(w+)

57.1=pXLBacII-GnTII-GalT-TetO#57 (dsRed), TAM2.2=pBSIE1.rtTAM2.1.1KITR (EGFP)

The following methods were used in this example.

Induction of transgenes—To induce the genes (GnTII and β4GalT) controlled under TetO promotor, Glyco6 strain adults were cultured on corn-meal media containing 0, 10 or 100 µg/ml doxycyclin (Dox). Media was also supplemented with ManNAc at 1 mg/ml to prime production of CMP-SAS. Climbing $3^{rd}$ instar larva were harvested for subsequent analysis.

Semi-quantitative RT-PCR—Total RNAs were extracted from induced and non-induced larvae with TriReagent (Sigma) and treated with DNaseI (Invtrogen) to remove residual genomic DNA. PCR was performed using oligodT primed cDNA as template and phusion Taq (Finnzyme). Gene-specific primers were designed to amplify 500 bp products. Band intensities were quantified using ImageJ software.

N-glycan analysis of whole larva—Larvae were homogenized in chloroform:methanol:water:4:8:3 and precipitated proteins were washed with acetone, dried and digested with trypsin/chymotrypsin. N-glycans were released from glycopeptides by digestion with PNGaseA (Calbiochem). Following C18 clean-up, glycans were permethylated and analyzed by nanospray ionization (NSI)-mass spectrometry (MS, LTQ-Orbitrap; ThermoFisher). Glycans were identified and quantified using Xcaliber software.

FIG. 5 shows the N-glycan pattern observed using this approach in Drosophila. The data shown in FIG. 6 show that semi-qualitative RT-OCR confirms the induction of expression of the Tet-O regulated. Glyco6 genes (GalT and GnTII).

To investigate the glycan expression changes associated with dox-induction in Glyco6, 3rd instar larva were harvested and homogenized. N-linked glycans were released from larval glycopeptides preparations by digestion with PNGaseA. Following permethylation, released glycans were analyzed by NSI-MS. See FIGS. 7A-7E and FIG. 8. The data show that dox-induced Glyco6 strains exhibit increased expression of sialylated glycans.

The data presented in this example demonstrate that

1) A glycoengineered insect, Drosophila melanogaster Glyco6, expresses transcripts for four constitutive and two doxycyclin-inducible glycogens;

2) The expression of mammalian-type sialylated complex glycans in Glyco6 was detected by NSI-MS. The prevalence of total sialylated glycans was increased 12.5-fold over control by the lowest dose of inducer (10 μg/ml dox).

Example VIII

Producing Transgenic *T. ni*

*T. ni* is transfected with the piggybac element. In brief, the protocol involves the timed harvesting of eggs from wax paper. *T. ni* prefer to lay their eggs when the lights go off. Timing the light cycle for 12 hours on and 12 hours off such that the moths begin laying eggs at 8:00 AM allows harvesting of eggs for the next two hours. The eggs are easily released from the wax paper by brushing, and collected into a glass petri dish. They are then washed in 2% formalin, rinsed with water, air dried for 15 minutes, and then picked up from the filter paper with a fine brush. The eggs are secured with double-sided tape to a slide for microinjection. *T. ni* eggs have a top and bottom symmetry, but the embryo develops horizontally around the egg. It is therefore impossible to determine where germ line nuclei are developing. Instead, we use the rapid diffusion of the injected DNA throughout the embryo, coupled with slow cellularization (up to 4 hours), to permit the injected DNA to make its way into germ line nuclei. A protocol for establishment of transgenic *T. ni* is outlined below:

A. Establishing transgenic *T. ni* expressing mammalian glycosylation enzymes: Surviving insects from microinjections with the constructs discussed above are individually mated with wild-type *T. ni*. These matings are performed by combining five female wild type moths with each surviving microinjected G0 male. All G0 females are mass mated to wild type males. Expression of the fluorescent marker in these G0 insects is not necessarily a prerequisite for their selection for mating, since establishment of the transgene in germ line tissue is not necessarily reflected as an expressed fluorescence.

The progeny F1 insects from these matings are screened for expression of the fluorescent marker in the eyes of adults, or in any other tissues. Some position effects can generate fluorescence in tissues other than the eye as well. The screening of these adults is performed immediately upon emergence from the puparium and prior to mating. These adults are anesthetized by exposure to ether, $CO_2$, or cold. Positive insects are selected for individual mating to wild type insects of the other sex. The proportion for mating is one F1 positive to five wild type of the opposite sex. F2 progeny is screened from each F1 line and fluorescent positive males and females from each line are mated to establish a homozygous lineage for each line. Once homozygous lines are established for each enzyme, they are examined for expression of the transgene. In each case, RT-PCR are used to measure expression of the transgene.

Glycosylation is assessed as described elsewhere herein.

B. Establishing a Baculovirus-Induced Tet-Responsive System for Expression of Mammalian Glycosylation Enzymes in *T. ni*:

It may be advantageous, or even necessary, to have these mammalian glycosylation enzymes expressed only during a baculovirus infection. We adapt the Tet-inducible strategy already shown to be effective in *Drosophila* (Stebbins et al. (2001) *Proc. Natl. Acad Sci.* 98, 10775-10780) to the baculovirus infected lepidopteran system by generating a transgenic *T. ni* line that expresses the rtTA-M2 mutation of the Tet repressor protein (TetON) under the control of the baculovirus p6.9 late promoter gene (Hill-Perkins et al. (1990) *J. Gen. Virol.* 71, 971-976). A similar strategy has been employed to effect controlled expression of genes from the baculovirus very late p10 promoter during baculovirus infections of cell cultures (Wu et al. (2000) *J. Biotech.* 80, 75-83). In our case, the p6.9 promoter, which is only active during baculovirus infection and is silent in the absence of baculovirus early gene expression, is used to ensure that expression of the N-glycan processing enzymes (in this case, under the control of a TetON inducible promoter) occurs before the recombinant glycoprotein of interest is expressed under polyhedrin control by the baculovirus vector. The TetON protein gene is linked to this promoter and assembled within a piggyBac transposon with a 3XP3-GFP marker gene for transfer into the genome of *T. ni*. The inducible expression of this protein is assessed once transgenic strains are established by RT-PCR assays after baculovirus infection. Since there are only three GFP derivatives that can be used simultaneously in a given insect (Example V), this TetON strain must be constructed independently of the mammalian glycosylation strains.

Matings and screening by southern hybridization and baculovirus-inducible expression of glycosyltransferases establish the final combined homozygous strains. In these strains, the mammalian N-glycan processing enzymes are only expressed during baculovirus infection in the presence of tetracycline or doxycycline.

Example IX

Expressing and Purifying GST-SfManI from Normal and Transgenic Insects

GST-SfManI is the recombinant model glycoprotein that is used to evaluate the N-glycan processing capabilities of our transgenic insects, as discussed above. A. recombinant baculovirus encoding a secreted form of this product under the control of the strong polyhedrin promoter is available from a previous study (Kawar et al. (2000) *Glycobiology* 10, 347-55). This virus is used to produce GST-SfManI for structural analyses of the N-glycans produced by parental and transgenic insect larvae. To avoid wound-induced stress from injection, viral inoculations are done orally. Inoculum stocks suitable for oral infection (consisting of the pre-occluded virus) are prepared according to conventional protocols and the potency is determined by conventional bioassay procedures. For experimental infections, groups of synchronized early fifth instar *T. ni* larvae are given a small (50 μl) plug of diet with the desired dose of viral inoculum. The insect is allowed to feed for a defined time interval and only larvae that have consumed the entire diet plug are included in the experiment. In experiments determining optimal times of harvest, larvae are harvested at preset time intervals (e.g., 84, 96, and 108 h post infection), and about 25 μl haemolymph is collected from each larva in a tube with buffer containing 1-phenyl-2-thiourea to inhibit melanization. For production experiments, recombinant GST-SfManI is harvested at the optimal time post infection and purified by glutathione affinity chromatography, using a slight modification of a previously described method (Hollister et al. (2001) *Glycobiology* 11, 1-9). Briefly, the hemolymph is harvested from infected larvae in the presence of 1-phenyl-2-thiourea, the samples are clarified by low speed centrifugation, and budded virus is removed by ultracentrifugation. The resulting supernatant is concentrated with polyethylene glycol and the precipitate harvested by centrifugation. The pellet is dissolved in glutathione column binding buffer [25 mM Tris-HCl pH 8.0, 250 mM NaCl and 1.5% (v/v) Triton X-100] and extensively dialyzed against this same buffer. The dialyzed material is then applied at room temperature to an immobilized glutathione-agarose column prepared from a commercial affinity matrix and equilibrated with column binding buffer. The column is then washed with excess column binding buffer, washed again with excess glycosidase buffer (5 mM $Na_2HPO_4$, pH 7.5), and the GST-SfManI is eluted with a small volume of glycosidase buffer supplemented with 10 mM reduced glutathione. Affinity-purified GST-SfManI preparations are re-dialyzed against glycosidase buffer (5 mM $Na_2HPO_4$, pH 7.5) to remove the glutathione and the total protein concentration is determined using a commercial Bradford assay. Samples of the starting material, flow-through, washes, and eluants are analyzed by SDS-PAGE with Coomassie blue staining or immunoblotting to monitor the purification procedure.

To address a potential problem in the purification of GST-SfManI from baculovirus-infected insect larvae (lipids in the larval hemolymph that may interfere with binding of the recombinant glycoprotein to the glutathione affinity column), we significantly dilute the material to be applied to the column, then circulate it over the affinity column for an extended time period in a cold room. Alternatively, a different affinity purification method is used. We produce a recombinant baculovirus that encodes a 6xHIS-tagged version of GST-SfManI. The 6x-HIS tag allows us to use metal affinity column chromatography as an alternative approach to purify essentially the same model glycoprotein. The properties of this protein, including expression levels, secretion efficiencies, glycosylation, and N-glycan processing, are evaluated to ensure that it has the same desirable features as the GST-tagged form of SfManI.

Example X

Characterizing N-Glycans Produced by Normal and Transgenic Insects

Lectin blotting assays, together with stringent specificity controls, are a simple and effective way to analyze N-glycans on recombinant glycoproteins. See, for example, Hollister et al. (2001) *Glycobiology* 11, 1-9; Breitbach et al. (2001) *Biotech. Bioengr.* 74, 230-9; Jarvis et al. (1995) *Virology* 212, 500-11; Jarvis et al (1996) *Nature/Biotech.* 14, 1288-92. The advantages of the lectin blotting method include simplicity and rapidity. Although lectin binding is an indirect method, when properly controlled, lectin blotting experiments are uniformly confirmed using more direct and sophisticated analytical methods. Lectin blotting assays are coupled with competing sugar and glycosidase controls, as previously described (Hollister et al. (2001) *Glycobiology* 11, 1-9), to examine the compositions of the N-glycans on the GST-SfManI produced by normal or transgenic insect larvae. These analyses provide an initial view of the N-glycan processing capabilities in our transgenic insects and provide a justification for performing more labor-intensive and expensive, but more definitive and comprehensive, structural analyses.

The N-glycans from GST-SfManI or other model glycoproteins produced by the normal or transgenic insect larvae are removed in preparation for the latter structural analyses. We have previously shown that GST-SfManI can be quantitatively deglycosylated using an endoglycosidase called peptide-N-glycosidase-F (PNGase-F). The behavior of GST-SfManI produced by baculovirus-infected *Trichoplusia ni* larvae is examined. If the latter protein is core-fucosylated, it is not completely deglycosylated with PNGase-F. This problem is addressed by using a mixture of PNGase-F and another endoglycosidase, PNGase-A (Tretter et al. (1991) *Eur. J. Biochem.* 199, 647-652). About 1 mg of purified GST-SfManI is required from each source for comprehensive N-glycan structural analyses. The N-glycans are released from 1 mg samples of the recombinant protein from each source by exhaustive endoglycosidase digestion, as described previously (Hollister et al. (2001) *Glycobiology* 11, 1-9). The released N-glycans in the spent reactions are bound to graphitized carbon cartridges. The protein and salts are washed out with water, then total N-glycans eluted with acetonitrile. Alternatively, trifluoroacetic acid is used to separately elute neutral and charged (sialylated) N-glycan species for independent structural analyses (Handler et al. (2001) *Biotechniques* 31, 820, 824-8). After elution from these cartridges, the N-glycans are analyzed by various chromatographic and mass spectroscopic methods, as described below. In addition, one can couple the PNGase-F-mediated release of N-glycans with various exoglycosidase treatments (Packer et al. (1998) *Glycoconj J* 15, 737-47). A comparison of the chromatographic or spectroscopic profiles of the N-glycans released with. PNGase-F alone and those released and partially degraded by combined digestions with PNGase-F and an exoglycosidase are used to identify the terminal monosaccharides on N-glycans. For example, if one couples PNGase-F and sialidase treatments and the profile changes in the predicted fashion, then this provides direct evidence that the original N-glycan was sialylated. Many specific exoglycosidases are commercially available for this purpose, including β-galactosidases, alpha-fucosidases, β-N-acetylhexosaminidases, and alpha-mannosidases, and these reagents can be applied to effectively "sequence" N-glycans. While each specific endo- and exoglycosidase reaction requires specific buffers and other conditions, these are readily available from the literature and manufacturer's recommendations.

There are many conventional ways to analyze N-glycan structures. We use one common chromatographic method known as high pH anion exchange chromatography with pulsed amperometric detection (HPAEC-PAD). See, e.g., Hollister et al. (2001) *Glycobiology* 11, 1-9; Hollister et al. (2002) *Biochemistry* 41, 15093-15104. N-glycans are isolated from the GST-SfManI produced by various larvae, as described above, then injected into an HPAEC-PAD system equipped with a Carbo-Pac PA100 column equilibrated with 50 mM NaOH. This column is specifically designed for oligosaccharide separations. After being injected, the column is washed with 50 mM NaOH, then N-glycans are eluted with a linear gradient of 0 to 125 mM sodium acetate over 45 minutes at a flow rate of 1 ml/min. Commercial N-glycans and/or N-glycans from the GST-SfManI produced by our normal and transgenic insect cell lines are used as standards. The latter structures have been unequivocally determined using mass spectroscopic and tandem mass spectroscopic methods. In addition, some commercial monosaccharide standards, particularly sialic acid, can be useful for these experiments. Using these standards, we are able to identify any co-eluting N-glycan structures isolated from the GST-SfManI or other recombinant glycoproteins produced by normal or transgenic insect larvae. Together with the data obtained from exoglycosidase sequencing experiments, we are able to identify N-glycan structures with great confidence. The unequivocal, comprehensive determination of N-glycan structures are carried out using mass spectroscopic and tandem mass spectroscopic analysis of N-glycan samples, (e.g., see FIGS. 7 and 8).

The presence of contaminants in the N-glycan preparations that can interfere with pulsed amperometric detection can be circumvented by using established methods to label N-glycans with various fluorochromes, such as 2-aminobenzamide, which enables their specific detection if a fluorescence detector is added to the HPAEC-PAD system (Kotani et al. (1998) *Anal Biochem* 264, 66-73).

Example XL

Introducing Multiple Glycosylating Enzymes into *T. ni*

The iel/hr5 subset of the piggybac vectors described above is used to introduce the mammalian processing enzymes directly into the baculovirus genome. A baculovirus encoding each of the mammalian processing enzymes discussed above is used as the parental virus for the production of baculovirus expression vectors encoding recombinant glycoproteins with mammalian glycan profiles.

The piggyBac vectors encoding GlcNAc-TII, β4Gal-TI, ST6GalI, ST3GalIV, SAS, and CMP-SAS under the control of the iel promoter are used to introduce these genes into the genome of the baculovirus, *Autographa califbrnica* multicapsid nucleopolyhedrovirus (AcMNPV). Briefly, viral genomic DNA isolated by a conventional method is mixed with the appropriate piggybac vector DNA in the presence of a helper plasmid encoding the transposase. Expression of the transposase helper is driven by polh, and the mixture is used to transfect Sf9 cells by conventional transfection procedures. Medium from the transfected cells is harvested four days later and budded virus progeny resolved, using conventional baculovirus plaque assays (see, e.g., O'Reilly et al (1992) "Baculovirus expression vectors." W. H. Freeman and Company, New York). Recombinants are identified by the presence of fluorescent protein markers, which can be visualized directly in the infected cells. This is done in a stepwise fashion, inserting each vector construct independently and sequentially, or by simultaneous insertion of all three constructs. Recombinant baculovirus clones that have all three fluorescent protein markers are amplified and checked for each of the transgenes of interest by dot blot assays. Virus clones that have all of the mammalian genes of interest are examined for their ability to express those genes during infection of Sf9 or Sfβ4GalT/ST6 cells, as described above. This yields a novel baculovirus expression vector with the mammalian glycoprotein processing genes that are needed to extend the insect N-glycosylation pathway. An existing transfer plasmid is used to introduce an *E. coli* LacZ marker and three Bsu361 sites into the polyhedrin locus of this virus, by analogy to a previously described baculovirus vector (Kitts et al. (1993) *Biotechniques* 14, 810-7). This greatly facilitates the subsequent use of the resulting recombinant virus as a parental strain for the isolation of secondary recombinant baculovirus expression vectors encoding glycoproteins of interest under the control of the strong polyhedrin promoter.

We introduce the polyhedrin-driven GST-SfManI gene into this parental virus using conventional protocols, and use the resulting virus to express GST-SfManI in normal insect larvae. The existing virus, AcGST-SfManI, which lacks the mammalian glycoprotein processing genes, is used as a negative control. Subsequently, both forms of GST-SfManI are affinity-purified and analyzed by lectin blotting assays, as described above. In addition, the N-glycans are removed from each protein preparation and used for more comprehensive structural analyses, as described above.

Example XII

Negative Regulation of Endogenous GlcNAcase Activity

A recent study suggests that it might be possible to enhance the efficiency of N-glycan. processing in insect cells by inhibiting the endogenous GlcNAcase activity (Watanabe et al. (2001) *J. Biol. Chem.* 277, 5090-5093). While this approach is economically is not feasible for large scale protein production using insect larvae, an attractive alternative approach uses RNA-interference (RNAi) to reduce or eliminate GlcNAcase activity. This approach requires at least partial GlcNAcase gene sequences, which have now been determined from *S. frugiperda* (Geisler et al., 2008, Journal of Biological Chemistry, 283:11330-11339), as well as from *B. mori* and *T. ni* (Geisler and Jarvis, 2009, Biotechnology Progress, epub PMID: 19882694).

This inhibition can enhance the efficiency of producing mammalianized proteins in the transgenic insects of the invention. Inhibiting the GlcNAcase in normal insects, which contain no mammalian glycosyltransferase genes, may be desirable when subjecting proteins to N-glycan processing by these organisms.

Methods to design and generate RNAi specific for a nucleic acid sequence are conventional. In one embodiment, short selected double stranded sequences are synthesized chemically and annealed. In another embodiment, the two strands of the double strand siRNA are transcribed from a suitable expression vector in vitro, annealed, and transfected as dsRNA into the cells. In another embodiment, the GlcNAcase cDNA is used to construct a piggyBac vector encoding an inverted repeat corresponding to all or part of the GlcNAcase coding sequence, with a short spacer sequence in-between. This sequence is placed under the control of the iel or iel-tet$^{on}$ promoter for constitutive or regulated production of a dsRNA molecule with a stem-loop structure, which mediates post-transcriptional gene silencing (Kennerdell et al. (2000) *Nat Biotechnol* 18, 896-8). The GlcNAcase stem-loop construct is assembled from two PCR products encoding the entire open reading frame flanked by unique restriction sites, essentially as described (Kennerdell et al. (2000), supra). One PCR product begins with a unique BglII site and the other begins with a unique SpeI site. Each has a slightly different SfiI site on its 3'end, which, when digested and religated, produces dimers with a nonpalindromic, central 5 bp sequence. This sequence serves as the spacer between the inverted repeats and will create the loop in the RNA stem-loop structure. The PCR amplimers are digested with SfiI, ligated, and dimers are gel-purified, digested with BglII and SpeI, and subcloned downstream of the iel or iel-tet$^{on}$ promoter in the piggybac vectors described above. The resulting piggybac vector is used to transform or supertransform *T. ni* larvae, as described above. Ultimately, GST-SfManI is produced in larvae known to be expressing the RNAi construct, affinity-purified, and its N-glycans are isolated and analyzed, as described above. siRNAs specific for the cloned GlcNAcase, or for a portion thereof, are expected to reduce or eliminate this enzyme activity in cultured Sf9 cells, and thus possibly to increase the efficiency of glycoprotein sialylation.

Expression or introduction of an interfering RNA is also expected to reduce or eliminate GlcNAcase activity in transgenic insects expressing mammalian glycosyltransferases. See, e.g., Kramer and Bentley (2003) *Metabolic Engineering* 5, 183-190, which reports that an siRNA against GFP (green fluorescent protein) is effective to inhibit expression of that protein in *T. ni* larvae.

Example XIII

Overcoming Potential Immunogenicity Problems

Some insects (e.g., *T. ni*) have an alpha-1,3-fucosyltransferase (FT3) that can add alpha 1,3-linked fucose residues to the linkage sugar of N-linked glycans (Marz et al. (1995). Protein glycosylation in insects. In "Glycoproteins" (J. Montreuil, J. F. G. Vliegenthart, and H. Schachter, Eds.), Vol. 29a, pp. 543-563. Elsevier, Amsterdam; Kubelka et al. (1994) *Arch. Biochem. Biophys.* 308, 148-157; Staudacher et al. (1992) *Eur. J. Biochem.* 207, 987-993). This activity has been observed, and genes encoding this enzyme have been cloned and sequenced from, e.g., *Arabidopsis, Drosophila* and *C. elegans*. The presence of this enzyme is a potential problem because the addition of this fucose residue generates an immunogenic carbohydrate epitope related or identical to the horseradish peroxidase (HRP) epitope found on some plant glycoproteins (Fabini et al. (2001) *J Biol Chem* 276, 28058-67). One method to address this problem is to first identify whether the transgenic insects have alpha 1,3-linked core fucose residues by structural analyses of the N-glycans isolated from recombinant glycoproteins they produced. If they have this moiety, the problem is addressed in one or more of the following ways.

A. Post Production Enzyme Treatment:

The simplest solution is to treat the purified recombinant glycoprotein with alpha-fucosidase. This enzyme is absolutely specific for terminal, alpha-linked fucose residues and is widely used to remove fucose residues from N-glycans (Jacob et al. (1994) *Meth. Enzymol.* 230, 280-99). Samples of the purified recombinant glycoprotein taken before and after treatment are analyzed by western blotting with a commercially available anti-HRP antibody, which only binds to the glycoprotein if it has alpha 1,3-linked fucose (Fabini et al. (2001) *J Biol Chem* 276, 28058-67). If alpha-fucosidase treatment is effective, the recombinant glycoprotein is separated from the enzyme and the preparation is complete. The completed preparation is deglycosylated and the structures of the released N-glycans directly determined, as described above, to confirm defucosylation at a higher level of sensitivity. If the western blots or direct structural analyses indicate that alpha-fucosidase treatment did not effectively defucosylate the recombinant glycoprotein, an alternative solution is undertaken.

B. Characterization of Alternative Lepidopteran Fucosylation Properties:

Another method is to identify an AcMNPV-permissive insect species with no FT3 activity by analyzing the FT3 status of different lepidopteran insect species, including *T. ni, Spodoptera frugiperda, Estigmene acrea, Heliothis virescens,* and *Spodoptera exigua*. For these assays, a BEV is used to express a recombinant glycoprotein of interest in each insect, then the product is isolated and probed for alpha 1,3-fucose using the anti-HRP antibody. Any glycoprotein preparation that fails to react with this antibody is deglycosylated with a mixture of PNGase-F and PNGase-A and the N-glycans are recovered and their structures directly analyzed using HPLC or mass spectroscopy, which provide a higher level of sensitivity, as described above. An AcMNPV-permissive host that lacks FT3 is used in place of *T. ni* as the parental insect for the transgenesis experiments described above. Alternatively *T. ni* can be used because this is the insect used in mass larval rearing and infection for recombinant protein expression.

C. RNAi Suppression of FT3 Expression:

Another method is to prepare an insect by using the RNAi approach, by analogy to the experiments described above for knocking out the GlcNAcase gene. This solution to the immunogenicity problem requires isolation of the FT3 gene from *T. ni*, which is needed to produce a transgenic insect that constitutively expresses a fragment of this gene as DS RNA.

A partial sequence of a *Trichoplusia ni* core α1, 3 fucosyltransferase has been cloned and sequenced. Amino acid sequences from the demonstrated core α1, 3 fucosyltransferase from *Drosophila melanogaster* (Fabini et al. (2001) *J Biol Chem* 276, 28058) and putative core α1, 3 fucosyltransferases of *Anopheles gambiae* and *Apis mellifera* were aligned with each other by ClustalW. Regions of high sequence conservation among the three sequences were identified and used to design degenerate oligonucleotides for PCR. Degenerate PCR with one pair of primers yielded a product of the predicted size. When this 218 bp PCR product was cloned and sequenced, it found to encode an amino acid sequence with a high level of sequence identity to the other insect core α1, 3 fucosyltransferase sequences. When a BLAST-p homology search of non-redundant amino acid sequences was carried out using the *T. ni* PCR product amino acid sequence as a query, the highest match was with the *Apis mellifera* core 60 1,3 fucosyltransferase.

The sequence of the *T. ni* fragment is:

```
                                           (SEQ ID NO: 1)
GTGGCGTGGTTTGTTTGGAACTGCCACGCCCGCAACCGCCGCCTGCAGTA

CGCGCGGCAGCTCAGCAGGCACATCCAGGTGGACATCTACGGTGCGTGCG

GCTCGCACCACTGCCCCCGCACTGACCCCAACTGCCTGGAGATGCTCGAC

AGGGACTACAAGTTCTACCTCGCATTTGAAAATTCTAACTGTCGTGATTA

CATCACAGAGAAGTTCTT
``` siRNAs are designed, using conventional procedures, that are specific for the entire sequence of SEQ ID NO: 1, or for fragments thereof. The siRNAs are first tested for efficacy in cell culture, and are then introduced into insects of the invention. Other conventional methods for suppressing FT3 expression are also employed. These methods include, for example, the use of antisense nucleic acid, or generating "knockouts" of the gene by, e.g., homologous recombination.

The elimination of FT3 activity is useful, not only in the context of insects that produce mammalianized glycoproteins, but also for insects that are not modified to produce mammalianized glycoproteins. For example, insect-like glycoproteins that have been treated to remove alpha 1,3-linked fucose residues, and thus lack that immunogenic carbohydrate epitope, can be useful as vaccines; the major epitopes in such a vaccine are from the polypeptide of interest, itself, rather than the "non-mammalian" carbohydrate residue.

Accordingly, a form of "non-insectivized" polypeptide is one in which alpha 1,3-linked core fucose residues are absent from the linkage sugar of an N-linked glycan. Such a "non-insectivized" heterologous polypeptide can be generated in an insect (e.g., a transgenic insect), wherein the insect is selected or modified so as not to express FT3 in its cells, using any of the methods described above. Optionally, such an insect may also express in its cells suitable recombinant glycosylation enzymes, as is discussed elsewhere herein.

Example XIV

Methods for Introducing Polypeptides of Interest into a Transgenic Animal that Expresses Mammalianizing Glycoproteins Typically, inoculation of larvae has been done by injection with budded virus or feeding of occluded virus. Preferably, a different route is used in methods of the invention, because automated injection of larvae is not feasible and oral infection with occluded virus is detrimental for product protein yield (competition of polyhedrin synthesis) and complicates sanitation. A preferable form of inoculation is oral inoculation, using a pre-occluded virus (POV) form. This is virus localized in the nucleus and destined to be occluded in a paracrystalline matrix of the protein polyhedrin, except that the polyhedrin gene is deleted from the viral genome. Conventional methods may be used. Guidance regarding oral inoculation with POV inoculum is provided in U.S. Pat. Nos. 6,090,379 and 5,593,669. An exemplary embodiment is described below:

Preparation of POV Inoculum.

Early 5th instar *T. ni* larvae are injected with budded virus and incubated. Larvae are monitored for symptoms of infection and mortality. Moribund larvae are collected and frozen. The frozen larvae are then lyophilized.

When lyophilized cadavers are removed from the freeze dryer the % solids of the lyophilized cadavers is confirmed to be between 21% and 23%. The dry cadavers are then milled into bulking material to form a wettable powder which serves as the POV inoculum. The WP is stored at −80° C. and serves as POV inoculum stock.

Inoculation of Larvae with POV

A suspension of the POV stock is prepared in water containing 2.5% sucrose. This suspension is screened through a 48 mesh sieve to remove debris that would plug hypodermic needles on the inoculator, and is then ready for use.

The virus inoculator consist of four parts:
a) a pump, connected to
b) a manifold with hypodermic needles in a pattern fitting that of the wells in the trays with insects
c) a platform that moves the manifold with the needles up and down
d) guardrails that allow the trays with insects to be placed directly under the needles The operation of the machine depends on a foot-pedal switch-activated and compressed air-powered depression of the platform. This action forces the hypodermic needles through the topfilm of the trays while at the same time a defined amount of inoculum is sprayed in the chambers. The platform then pulls the needles out of the wells, and a new tray can be placed under the platform. The sequence and coordination of events is controlled by microswitches. The effective dose applied by the inoculator machine to each well is equivalent to 33 µg lyophilized cadaver/well. This may be adjusted based on potency of POV inoculum.

Example XV

Growth Conditions (Insect Mass Rearing: Process Variables)

The mass rearing of *Trichoplusia ni* for protein manufacturing falls into two functionally different processes. The first is maintenance of a breeding colony, based on the insect's life cycle of approximately 4 weeks. The second process pertains to the diversion of large numbers of larvae from the breeding colony to serve as production larvae.

Maintenance of the Breeding Colony.

Breeding methods for some Lepidoptera are well established, and in this category fall noctuid moths such as the cabbage looper (*Trichoplusia ni*). The life cycle consists of 4 stages: egg stage, larval stage, pupal stage, and adult stage. The inventors have determined optimal conditions under which the insects need to be kept, and have established protocols for handling of the insects during each of these stages. The following lists the tolerances in conditions and indicates some alternative handling procedures for *T. ni*.

Eggs.

The egg stage is short (about 3 days). Eggs are typically laid on a solid substrate such as paper towels or muslin cloth. *T. ni* deposits its eggs separately on the substrate to which the eggs stick. Eggs are removed from the substrate and collected using a dilute bleach solution. After rinsing the eggs they are incubated in a moist bulking agent until one day before egg hatch. Then the eggs are "packaged" by a form-fill-and-seal machine in a continuous, automated process. This process starts with indentations (wells) being thermoformed in a sheet of PVC film (the web), and flash-sterilized, liquid, semi-synthetic insect diet is distributed into the wells via a manifold. The web then moves through a cooling tunnel where the diet solidifies. Next the eggs in the bulking agent are deposited onto the diet which has solidified. Finally, at the end of the line, perforated film is thermosealed over the wells. For a period of approximately one day the eggs remain on the diet under standard incubation conditions until the larvae hatch. Process variables to be optimized include: Substrate for oviposition; egg removal procedure (% bleach, immersion time); bulking agent; type of diet; type of top film and perforations (gas exchange); and incubation conditions (temperature, relative humidity, light regimen)

Larvae.

Larvae hatch as neonates and after eating the remains of the egg shell, they start feeding on the synthetic diet. The larvae when incubated under standard conditions grow over a period of 12 days through 5 instars and pupate. Process variables to be optimized include: incubation conditions, such as temperature, relative humidity, and light regimen.

Pupae.

Pupae embedded in a cocoon stay in average for 3 days in the wells under the same conditions as for larval growth. Then the pupae are released from their cocoons and placed into the adult emergence cages. Process variables to be optimized include: cocoon removal procedure (manually, % bleach, immersion time); and incubation conditions (temperature, relative humidity, light regimen).

Adults.

After 1-2 days both female and male adults emerge and they are allowed to mate and lay eggs. Eggs are collected daily. Process variables to be optimized include: type of adult emergence cage (carton, wire cage); number of adults per cage; incubation conditions (temperature, relative humidity, light regimen).

Production Larvae.

Massive numbers of larvae are diverted from the colony maintenance cycle and are used as the hosts for protein production. The sheer numbers involved make automation a necessity. Essentially 99.9% of the insects packaged in the form-fill-and-seal-machine are inoculated with recombinant baculovirus as late instars. While the inoculated larvae keep eating and growing for several days more, their development is halted by the viral infection and they do not pupate. These larvae are harvested at the appropriate time, frozen and are

Example XVI

Transformed *Bombyx mori* with Mammalian Glycosylation Capabilities for Production of Mammalian Proteins in the Silk Gland The development of transgenic silkworms as a novel system for the production of recombinant glycoproteins is described in the present example. Successful development of the silkworm for this purpose will facilitate basic research on glycoprotein structure and function. This approach also could be used by industry to produce recombinant glycoproteins for direct clinical use as vaccines or therapeutics. The biotechnological impact of this system could be huge, considering that many high profile, clinically relevant proteins, such as antibodies (e.g., Herceptin®), cytokines (e.g., EPOGEN), and anticoagulants (e.g., Tenecteplase™) are glycoproteins. At a more basic level, the metabolic engineering effort underlying this project is an elaborate "ectopic expression" experiment that will broadly address the biological significance of the differences in protein N-glycosylation pathways of lower and higher eukaryotes. These results will be of great interest to basic scientists, particularly glycobiologists studying protein N-glycosylation in lower organisms and the evolution of protein glycosylation pathways. Finally, these results will be of great interest to bioengineers working to overcome the evolutionary limitations of lower eukaryotic systems for recombinant glycoprotein production.

The p25 promoter of the silkworm, *Bombyx mori*, is used to obtain organ-specific expression of genes in the posterior silk gland. The silk fibroin light or heavy chain gene promoter is used to obtain organ specific expression of genes in the median silk gland. The piggyBac transposon vector technology, as described elsewhere herein, is used.

Silkworms can be maintained in the absence of silk production. Using conventional procedures, piggyBac-based transformation vectors are constructed which can introduce mammalian glycosylation enzymes for restricted expression (or restricted and controlled expression) in the silk gland.

Bivalent promoter cassettes are constructed that allow for the expression of two mammalian glycosylation enzymes simultaneously from one transformation vector and a selectable fluorescent marker gene. Using conventional microinjection protocols, the vector and a helper plasmid that provides the transposase protein are introduced into embryos of *Bombyx mori* and transformed insects are selected. Conventional tests (e.g., PCR Protocols) are used to test for expression of the mammalian glycosylation enzymes in the silk gland of transformed insects. A second vector is then applied which contains additional mammalian glycosylation enzymes, and successful transformants are selected for as above. These steps are repeated until all the desired mammalian glycosylation enzymes are established in the genome of *Bombyx mori*. Transformed strains expressing individual combinations of glycosylation enzymes are mated to establish a single strain expressing all the desired mammalian glycosylation enzymes. Alternatively, a single strain is transformed to establish a multiply transformed strain expressing all the desired mammalian glycosylation enzymes.

Genetic Transformation of the Silkworm for Recombinant Protein Production.

The first successful transformation of *B. mori* was accomplished using the *Bombyx* actin 3 promoter (BmAc3) to drive expression of the transposase on a helper plasmid, pHA3PIG, together with a piggyBac vector encoding a BmAc3-controlled gene encoding enhanced green fluorescent protein (EGFP). Successful transformation was clearly evidenced by whole body fluorescence in the F1 generation. Subsequent studies explored the utility of alternate *Bombyx* promoters for expression and detection of fluorescent protein markers, including the 3XP3 eye-specific promoter, the immune-inducible cecropin B promoter, and two silk gland-specific promoters, one from the silk fibroin light chain (Flc) gene and the other from the silk fibrohexamerin (Fhx) gene. Importantly, the Flc and Fhx promoters provided tissue-specific transgene expression in the silk gland in each of the latter studies. In fact, foreign gene expression was strictly limited to the posterior silk gland cells, which is the usual site of fibroin light chain and fibrohexamerin biosynthesis.

The recombinant glycoproteins that will be used to assess the new silkworm-based production system should be (1) easy to purify and analyze and (2) biomedically significant. The first gene to be used will encode a model glycoprotein, GST-SfManI, which is a fusion product composed of a secretory signal peptide, glutathione-S-transferase (GST), and the soluble domain of a *S. frugiperda* class I α-mannosidase (SfManI). The chimeric gene, *Spodoptera furgiperda* class I Golgi α-mannosidase fused to gultathion S-teransferase (GST-SfManI), encodes the model glycoprotein for analysis of complex glycosylation patterns. This gene is cloned into the appropriate restriction enzyme sites between the *Bombyx mori* P25 promoter and the P25 polyadenylation signal. In this example the parent plasmid for this manipulation is pBSII-ITR1.1k 3XP3 ECFP. See FIG. 9. A general advantage of using GST-SfManI as a model glycoprotein for this project is that we have extensive previous experience using it as a model to document metabolic engineering of insect glycosylation pathways. The specific advantages of using GST-SfManI for this purpose are that it can be expressed and secreted at high levels (typical yield is ≥1 mg/50 mL of baculovirus-infected Sf9 cells), it has a single N-glycosylation site, which greatly simplifies downstream glycan structural analyses, the N-glycan is efficiently processed beyond the high mannose form, it is easily and efficiently purified using the GST affinity tag, and it is easily and efficiently enzymatically de-glycosylated. The only disadvantage of using this model glycoprotein is that it has no direct biomedical significance.

The second gene to be used in our proposed project will encode human erythropoietin (hEPO), a more complex product with obvious biomedical significance. hEPO is a soluble glycopeptide produced mainly by the kidneys in response to hypoxia. The major function of hEPO is to induce production of mature, oxygen-carrying cells by stimulating the proliferation and differentiation of erythroid precursors. Recombinant forms of hEPO are produced commercially in CHO cells and used to treat human anemia patients, including cancer patients and patients with chronic renal failure (86). hEPO has three N-glycans and one O-glycan and sialylation of the N-glycans extends its half-life in vivo and enhances its therapeutic efficacy. The N-glycans of hEPO can have bi-, tri-, and tetra-antennary structures. A transgenic silkworm with a humanized N-glycosylation pathway is unlikely to support higher level N-glycan branching, as it would presumably lack the requisite N-acetylglucos-aminyltransferases. However, this silkworm should produce bi-antennary, sialylated N-glycans.

One of the starting materials that will be used to construct the piggyBac vectors encoding either GST-SfManI or hEPO will be pTOPO-FhxReg, prepared as described above. The other starting materials will be plasmids containing cloned copies of the GST-SfManI or hEPO sequences, which are available in our labs. These latter two plasmids will be used as templates for PCRs designed to amplify the sequences encoding mature (without their signal peptides) GST-SfManI or hEPO and to add unique 5'-AvrII and 3'-NsiI, HindIII sites for subsequent in-frame subcloning into the corresponding unique sites of pTOPO-FhxReg. The products will be gel-purified, cloned into pCR2.1-TOPO, and recombinants with error-free inserts will be identified by restriction mapping and DNA sequencing. Each insert will then be excised with AvrII and HindIII, gel-purified, and individually subcloned into the corresponding sites of pTOPO-FhxReg to produce pFhxGSfMI and pFhxhEPO. The desired recombinants will be identified by restriction mapping and the upstream junction sequences, which must be in-frame, will be checked by DNA sequencing. A bgh polyadenylation sequence with 5'-NsiI and 3'-HindIII, PmeI sites will subsequently be produced by PCR and an existing plasmid as the template, and the products will be gel-purified, and cloned into pCR2.1-TOPO. After identifying a recombinant with an error-free insert by restriction mapping and DNA sequencing, the bgh polyadenylation signal will be excised with NsiI and HindIII and finally subcloned into the unique NsiI and HindIII sites of pFhxGSfMI and pFhxhEPO to produce pFhxGSfMI-pA and pFhxhEPO-pA. The plasmids described above will encode secretable forms of the recombinant glycoproteins of interest under the control of a strong silk gland-specific promoter. However, further manipulations will be necessary to assemble these genes into a piggyBac vector, which can be used to introduce the genes into the silkworm genome, and to add a whole body marker, which can be used to presumptively identify transformants containing these genes. We will use a whole body marker for the vectors encoding the recombinant glycoproteins of interest rather than another eye-specific marker to avoid problems with overlapping emission spectra. In this case, the marker will be an EGFP gene positioned under the transcriptional control of the *B. mori* actin 3C (Ac3C) promoter. This element will be assembled in three steps and then subcloned as a single fragment into pFhxGSfMI-pA and pFhxhEPO-pA, with the promoters positioned in opposite orientations. Briefly, PCR and an existing plasmid as the template will be used to produce a copy of the Ac3C promoter (nt 1763 to 2654, inclusive) flanked by 5'-PmlI and 3'-XhoI sites. This same promoter sequence has been used previously to obtain whole body EGFP expression in a transgenic silkworm (113). The PCR product will be gel-purified, cloned into pCR2.1-TOPO, and a recombinant with an error-free insert positioned upstream of the vector XhoI site will be identified by restriction mapping and DNA sequencing. Subsequently, PCR and an existing plasmid as the template will be used to produce a copy of the EGFP open reading frame beginning with the second codon and flanked by XhoI sites. This product also will be gel-purified, cloned into pCR2.1-TOPO, and a recombinant with an error-free insert will be identified by restriction mapping and DNA sequencing. The EGFP fragment will then be excised with XhoI, gel-purified, and used to replace the XhoI fragment of the pCR2.1-TOPO clone containing the Ac3C promoter to produce pAc3C-EGFP. A recombinant will be identified by restriction mapping and the 5' junction will be sequenced to ensure that the actin and EGFP coding sequences are in-frame. Subsequently, PCR will be used to produce a copy of the bgh polyadenylation signal with 3'-NsiI and 5'-NotI, PmlI, NsiI sites and the fragment will be gel-purified, cloned, and an error-free clone identified, as usual. This bgh polyadenylation signal will then be excised from the pCR2.1-TOPO clone, gel-purified, and subcloned into the unique NsiI site in pAc3C-EGFP, which is located immediately downstream of the EGFP sequence. The Ac3C-EGFP-bgh gene will then be excised from the resulting plasmid with PmlI and individually subcloned into the unique PmlI sites of pFhxGSfMI-pA and pFhxhEPO-pA. This will yield two pCR2.1-TOPO-based plasmids encoding the recombinant glycoproteins of interest in secretable forms under Fhx control and also encoding the whole body color marker EGFP under Ac3C control. Finally, each of these dual gene elements will be excised as single units with NotI (unique site located on 5' side of marker gene) and PmeI (unique site located on 5' end of GST-SfManI and hEPO genes) and subcloned into the corresponding unique sites of a modified version of pXLBac-II, in which an adaptor was used to add a unique PmeI site in-between HindIII and BglII in the multiple cloning site. This will position the genes encoding the glycoproteins of interest in the rightward orientation, with respect to the piggyBac terminal repeats, for optimal expression.

FIG. 10 shows a representative vector containing two genes expressing a α2,6-sialyltransferase (ST6GalI) and a α2,3-sialylytransferase (ST3GalIII) using the *Bombyx mori* P25 promoter and the P25 polyadenylation signal. Genes and promoters are PCR amplified and separately cloned into appropriate restriction enzyme sites. The enzyme coding domains are separated by a Picornavirus 2A fragment to permit simultaneous expression of both proteins from a single transcript. Other features of the plasmid include a 3XP3-expressed fluorescent protein gene, in this example, the ECFP gene. In this example the parent plasmid for this manipulation is pBSII-ITR1.1k 3XP3 ECFP.

FIG. 11 shows a vector containing two genes expressing a N-acetylglucosaminyl-transferase II (GnTII) and a β1,4-galactosyltransferase (GalT) gene using the *Bombyx mori* P25 promoter and the polyadenylation signal. Genes and promoters are PCR amplified and separately cloned into appropriate restriction enzyme sites. The enzyme coding domains are separated by a Picornavirus 2A fragment (e.g., GSGATNFSLLKQAGDVEENPGP (SEQ ID NO: 2) or NFDLLKLAGDVESNPG (SEQ ID NO: 3)) to permit simultaneous expression of both proteins from a single transcript. Other features of the plasmid include a *Bombyx mori* Actin3 promoter expressing the EYFP gene. In this example the parent plasmid for this manipulation is pBSII-ITR1.1k.

FIG. 12 shows an example of a two gene construct expressing a sialic acid synthase (SAS) and a CMP-sialic acid synthase (CMP-SAS) using the *Bombyx mori* P25 promoter and the P25 polyadenylation signal. Genes and promoters are PCR amplified and separately cloned into appropriate restriction enzyme sites. The enzyme coding domains are separated by a Picornavirus 2A fragment to permit simultaneous expression of both proteins from a single transcript. Other features of the plasmid include a 3XP3-expressed fluorescent protein gene, in this example, the DsRed gene. This example the parent plasmid for this manipulation is pBSII-ITR1.1k 3XP3DsRed.

Three dual gene cassettes (eg. FIGS. 10, 11 and 12), each including the P25 promoter, two glycosylation enzyme genes separated by a 2A peptide, and the P25 polyadenylation signal, can be individually cloned into a pBSII-ITR1.1K-3xP3ECFP plasmid to form a six glycoprotein genes expressing construct, pBSII-3xP3/ECFP-P25/6enzymes. See FIG. 13. The advantage of this configuration is that one transgenic may be made expressing all six enzymes necessary to reconstitute the mammalian complex glycosylation pathway. In this example the parent plasmid for this manipulation is pBSII-ITR1.1k 3XP3 ECFP.

Functional Analysis of Piggy Bac Vectors
Ex Vivo Silk Gland Assay.

Briefly, silk glands will be surgically removed from fifth instar silkworm larvae reared on diet with or without 1 mg/mL N-acetylmannosamine, placed in a plastic culture dish containing Grace's insect cell culture medium, and positioned at the optimal distance (6 cm) from the particle gun. The tissues will be bombarded with particles coated with the supercoiled piggyBac vectors encoding the various glycosylation enzymes or recombinant glycoproteins. The empty vector, pXLBac-II, will be used as a negative control. After bombardment, the silk glands will be re-implanted into the hemocoelic cavities of fifth instar silkworm larvae using an albumin-coated glass capillary tube inserted into an abdominal incision. The silk glands will be removed 72 h later and used for various assays of gene expression. The silk glands bombarded with piggyBac vectors encoding the glycosylation enzymes will be homogenized in the relevant assay buffers plus nonionic detergent and used for direct glycosyltransferase activity, sialic acid, or CMP-sialic acid assays, each of which is established in the Jarvis lab. Silk glands bombarded with the empty piggyBac vector or spiked with the relevant glycosyltransferase, sialic acid, or CMP-sialic acid, will serve as negative and positive controls, respectively. The silk glands bombarded with piggyBac vectors encoding the recombinant glycoproteins of interest will be examined by in situ immunohistochemistry, using polyclonal antisera against GST, anti-SfManI, or hEPO, which are available either commercially or in our labs. Alternatively, these tissues may be homogenized and used for western blotting analyses. We expect to be able to detect a precursor subpopulation of GST-SfManI and hEPO in the silk glands, despite the fact that they are destined for secretion, as previously observed for GFP by Royer and coworkers (2005).

These preliminary results demonstrate that we can, in fact, metabolically engineer intact insects to constitutively express mammalian protein N-glycosylation functions.

Production and Initial Characterization of Transgenic Silkworms.

The new piggyBac vectors described above will be utilized to produce transgenic silkworms. We plan to use two basic approaches to produce transgenic insects with humanized glycosylation pathways encoding either GST-SfManI or hEPO. One will be to simultaneously introduce the entire set of piggyBac vectors, including three vectors encoding the six glycosylation enzymes and one encoding GST-SfManI or hEPO, into single eggs in an attempt to produce the desired transgenic silkworms as quickly as possible. The other approach will be to individually introduce the piggyBac vectors into single eggs to produce transgenic silkworms encoding each pair of glycosylation enzymes, GST-SfManI, or hEPO. These insects will then be mated to ultimately produce a silkworm strain containing genes encoding all six glycosylation enzymes and either GST-SfManI or hEPO. Importantly, this latter approach will yield transgenic silkworms that will produce the recombinant glycoproteins with N-glycans derived from the native B. mori protein N-glycosylation pathway, which will be needed as negative controls to assess our efforts to humanize this pathway. In yet another approach, we will introduce a single construct comprising all six enzymes as shown in FIG. 13.

Silkworm Transformation and Identification of Transgenic Offspring

Generally, silkworm transformation involves introducing a mixture of one or more piggyBac vectors and a helper plasmid, encoding the piggyBac transposase, into pre-blastoderm embryos by microinjecting silkworm eggs. Blastoderm formation does not occur for as long as four hours after eggs are laid. Thus, collection and injection of embryos can be done at room temperature over a relatively long time period. The technical hurdle for microinjection is the need to breach the egg chorion, which poses a hard barrier. Tamura and coworkers perfected the microinjection technique for silkworms by piercing the chorion with a sharp tungsten needle and then precisely introducing a glass capillary injection needle into the resulting hole. This is now a relatively routine procedure in the Fraser lab, which is accomplished with an eppendorf robotic needle manipulator calibrated to puncture the chorion, remove the tungsten needle, insert the glass capillary, and inject the DNA solution. The eggs are then re-sealed using a small drop of glue and maintained under normal rearing conditions of 28° C. and 70% humidity until the larvae hatch. The surviving injected insects are then mated to generate F1 generation embryos for the subsequent identification of putative transformants, based on expression of the DS-Red or other eye color markers. Putative male and female transformants identified by this method are then mated to produce homozygous lineages for more detailed genetic analyses.

Once putative F1 transformants have been identified by eye or whole-body fluorescence, homozygous lineages will be produced and bona fide transformants identified by Southern blotting, as described previously. The Fraser lab has developed a standard method for the isolation of genomic DNA from adult silkworm tissues using a commercial reagent (DNAzol; MRC). The results of the Southern blotting analyses will establish the presence and number of transgenes in each lineage. The genomic locations of the piggyBac insertions then will be examined by an inverse PCR/DNA sequencing method developed in the Fraser lab. Briefly, genomic DNAs will be digested completely with either Hinp1I for 3' end analyses or Taq1 for 5' end analyses. The digestion products will be purified using a commercial kit (Geneclean; Q-Biogene), self-ligated, and used for first round PCR. The first-round PCR products will then be used as templates for second-round PCRs. The resulting PCR products will be cloned into pCRII (Invitrogen) and sequenced. Finally, the resulting junction sequences will be used to query the Silkbase database to identify the location of the insertions.

Characterization of Transgene Expression in Transgenic Silkworms

An established RT-PCR method will be used to evaluate transgene expression in homozygous transgenic silkworm lineages at the RNA level. Total RNA will be extracted from homogenized tissue using a commercial reagent (Trizol; Invitrogen), used for first-strand cDNA synthesis with a commercial SuperScript II kit (Invitrogen), and the first strand cDNA will be amplified with Taq polymerase and appropriate primer pairs under standard PCR conditions. The Southern blotting, inverse PCR, and RT-PCR results will clearly identify homozygous silkworm lineage(s) that have acquired the transgene(s) encoding the glycosylation enzymes and recombinant glycoproteins of interest by bona fide piggyBac transposition. These results also will identify transgenic insects that express these genes at the transcriptional level and these will be the animals used to assess recombinant glycoprotein production, secretion, and glycosylation.

Assessing Recombinant Glycoprotein Production and Secretion

Initially, we will examine the silk glands of the relevant transgenic insects for the presence of GST-SfManI and hEPO. Wild type silkworms and/or transgenic silkworms encoding one or more glycosylation enzymes will be used as negative controls. Known amounts of GST-SfManI and hEPO purified from Sf9 cells infected with recombinant baculoviruses will be used as positive controls. Silk glands will be dissected from fifth instar silkworms, homogenized in 60% LiSCN, diluted five-fold with 10 mM Tris-HCl (pH 7), 2% SDS, and 5% β-mercaptoethanol, and samples will be mixed with an equal volume of Laemmli sample buffer and analyzed by SDS-PAGE and western blotting, in parallel with various amounts of the positive control samples. Polyclonal antisera specific for GST, SfManI, and hEPO are available commercially or in our labs, as are other polyclonal antisera that can be used as negative controls for antibody specificity. Expression levels will be estimated by comparing band intensities to the positive controls. As expression should occur in the posterior silk gland, it might be of interest to physically separate the posterior and middle silk glands during dissection to more accurately assess the expression site. Alternatively, we could perform in situ immunocytochemistry assays using the relevant antisera, with negative controls including silk glands from wild type and/or irrelevant transgenic animals and an irrelevant antiserum, and positive controls including silk glands bombarded with the appropriate piggyBac vector DNA, as described above.

Subsequently, we will assess recombinant glycoprotein secretion. Cocoons will be harvested from the relevant transgenic silkworms and from irrelevant transgenic and/or wild type silkworms as the negative controls. The floss will be separated and loosely associated proteins extracted by sonicating for 10 min in 10 mM Tris-HCl (pH 7), followed by a low speed centrifugation. The supernatant will be mixed with Laemmli sample buffer and the pellet will be solubilized with 60% LiSCN, diluted, and mixed with Laemmli sample buffer, as described above. Proteins will be extracted from deflossed cocoons by homogenizing in 60% LiSCN, diluting, and mixing with Laemmli sample buffer, as described above. Finally, all fractions will be examined for the presence of the relevant recombinant glycoprotein by SDS-PAGE and western blotting, in parallel with various amounts of the purified protein controls, as described above. We also will use scanning electron microscopy to directly examine the silk fibers produced by transgenic silkworms, with wild type and/or irrelevant transgenics as negative controls, to determine if the fibers are associated with recombinant glycoprotein particles, as was observed with GFP.

Assessing Protein N-glycosylation

Two different approaches will be used to assess the protein N-glycosylation capabilities of the transgenic silkworms produced in this project. One will be to measure the various enzyme activities in silk gland extracts. The other will be to examine the structures of the N-glycans isolated from the recombinant glycoprotein products.

Glycosylation enzyme activities. The glycosyltransferase activities will be directly measured in silk gland homogenates, while SAS and CMP-SAS activities will be inferred from total sialic acid and CMP-sialic acid determinations, respectively. Each assay is established in the Jarvis lab and has been previously described. Each assay requires 0.1 mg of total protein and is performed in triplicate. Thus, preliminary work will be performed to estimate the total protein content per silk gland by the BCA method. Subsequently, the requisite number of silk glands will be harvested from fifth instar silkworms reared on diet with or without N-acetylmannosamine. Silkworms carrying the relevant transgenes will provide the experimental tissues and wild type and/or irrelevant transgenics will provide the negative controls. The silk glands will be homogenized in the appropriate assay buffers supplemented with nonionic detergents, total protein concentrations will be determined by the BCA method, and triplicate aliquots containing 0.1 mg of total protein will be used to measure the glycosylation enzyme activities, as described above. Homogenates spiked with the relevant glycosyltransferase or sugar will serve as positive controls. All results will be presented in terms of enzyme activity units per hour (or sugar content) per mg of total protein, with background activities (boiled homogenates for enzyme assays, blanks for spectrophotometric sugar determinations) subtracted from the experimental values and endogenous activities measured in the negative controls presented as such, to inform the reader about the levels of those activities in wild type *B. mori*.

N-glycan structures. Structural analysis of the N-glycans on SfManI and hEPO produced by our transgenic silkworms will provide a more direct view of their N-glycan processing capabilities. One fast and simple approach that can provide structural information without having to purify the glycoproteins or remove and recover the glycans is lectin blotting. Other approaches, such as HPLC and mass spectroscopic analyses, have been described herein previously.

Lectin blotting is similar to western blotting, as a crude target glycoprotein is resolved by SDS-PAGE and then transferred to a membrane, but it is probed with a lectin, rather than an antibody. Various lectins with defined carbohydrate binding specificities are available, lectin binding can be detected with a secondary reagent, and the results can reveal the carbohydrate compositions of glycoprotein glycans. We have used lectin blotting for this purpose in many previous studies and have validated our lectin blotting method using more direct and sophisticated methods, including HPLC and mass spectroscopy. Hence, we will use lectin blotting for our initial structural analysis of the N-glycans on the recombinant GST-SfManI and hEPO produced by transgenic silkworms. The starting material will be aqueous extracts of the silk floss from the relevant transgenic insects, prepared as described above. Floss extracts from transgenic insects expressing the recombinant glycoproteins without the mammalian glycosylation enzymes will be the negative controls. The recombinant glycoproteins produced by humanized lepidopteran insect cell lines will be the positive controls. The proteins will be analyzed in parallel with various lectins, as described previously. The biotinylated lectins used for these analyses will be ConA, RCA, SNA, and MAA, which bind to α-linked mannose, β-linked galactose, α-2,6-linked sialic acid, and α-2,3-linked sialic acid residues, respectively. Lectin binding will be detected using alkaline phosphatase-conjugated streptavidin and competing sugar and glycosidase pre-treatments will be included to control for lectin binding specificity, as usual.

N-glycans removed from the purified recombinant glycoproteins will be prepared for the proposed HPLC and mass spectroscopic analyses. Again, the starting material will be aqueous extracts of the floss from the relevant transgenic insects, including negative controls expressing the recombinant glycoproteins without the mammalian glycosylation enzymes. The recombinant glycoproteins should be the major, if not the only glycoprotein component in these extracts. Total protein content will be assessed by SDS-PAGE with Coomassie Blue staining and total glycoprotein content will be assessed by lectin blotting with ConA. The results will reveal whether or not further purification is needed. If necessary, GST-SfManI will be further purified by using a glutathione affinity chromatography method established in the Jarvis lab and hEPO will be further purified by adapting a published method, which will be simplified by the nature of the starting material. The purity of the final recombinant glycoprotein preparations will be re-assessed, as above, and if the recombinant glycoproteins represent the major (≥90%) glycoprotein bands, the preparations will be pure enough for our purposes. Past experience suggests we will need about 1 mg of each purified recombinant glycoprotein from the experimental and control insects for comprehensive N-glycan structural analyses. Thus, 1 mg samples of the recombinant glycoproteins from each source will be denatured and exhaustively digested with PNGase-F, as described previously. The released N-glycans will be bound to graphitized carbon cartridges, the proteins and salts will be washed away with water, and total N-glycans will be eluted with acetonitrile or trifluoroacetic acid will be used to separately elute the neutral and charged (sialylated) N-glycans for independent analyses. After being eluted, the N-glycans will be analyzed by HPLC or mass spectroscopy.

The transgenic silkworms created in accordance with this invention will produce GST-SfManI or hEPO. This expectation stems from project design, as the piggyBac vectors will be pre-screened for the ability to induce recombinant glycoprotein production in silk glands and the transgenic silkworms will be pre-screened for the presence of the transgene and transgene expression at the RNA level. Moreover, we expect the recombinant glycoproteins to be secreted with silk proteins, based on the piggyBac vector design and the previous results of Royer et al. (2005). Various amounts of GST-SfManI and hEPO should be found in each of the silk protein fractions described above.

We also expect to observe induction of the glycosyltransferase activities and increased levels of sialic acid and CMP-sialic acid in silk gland homogenates from the relevant transgenic insects. As above, this expectation stems from project design, which includes pre-screening of the piggyBac vectors for the ability to induce glycosylation enzyme activity in silk glands and pre-screening the transgenic silkworms for the presence of the transgene and transgene expression at the RNA level. This expectation is also based on our previous success using these same genes to humanize the protein N-glycosylation pathway in lepidopteran insect cell lines and to induce relevant activities in Drosophila. From our past experience with transformed insect cell lines and transgenic fruit flies, we expect to see a wide range of induction levels, from about 3 fold to 30-fold above background or endogenous levels, depending upon the activity.

Summary.

In accordance with the present invention, we have described how the N-glycosylation pathway of a multicellular animal, the silkworm, can be humanized by introducing genes encoding mammalian functions. The silkworm so engineered can produce and secrete recombinant glycoproteins at high levels which can be easily recovered in highly enriched form due to their loose association with silk fibers. The transgenic silkworms with a humanized protein N-glycosylation pathway can be used to advantage to produce biomedically relevant human glycoproteins with structurally authentic N-glycans. The results in Drosophila demonstrate the power of recombinant glycoprotein production in transgenic insects which is of great interest to the biotechnology community. The successful production of a transgenic silkworm for humanized recombinant glycoprotein production provides a new option for recombinant glycoprotein production that could have a large impact on human health, like the baculovirus-insect cell expression system.

Example XVII

TRANSPILLAR Larvae Commercialization

Chesapeake PERL has developed an automated process to generate large numbers of T. ni larvae in thermoformed habitats. These larvae are inoculated at the appropriate stage and harvested in a labor-extensive, semi-automated step. Finally, after processing the larvae, the protein product is recovered and purified to the required purity. This process is currently operational and enables at capacity the rearing and processing of circa 1 million larvae per week. While yields vary significantly for different types of proteins, 200, μg/larvae is a reasonable average yield estimate, in our experience. This indicates a production capacity of ca 200 grams of recombinant protein per week.

This methods disclosed herein help solve the crisis in biopharmaceutical manufacturing by making the development cycle for new biotechnology-based therapeutics more predictable and less difficult. A suite of technologies is developed based on inventive transgenic-modified caterpillars-TRANSPILLARs. Combining TRANSPILLAR larvae with fully developed protein manufacturing process enables efficient, high-volume, cost-competitive development of a broad range of biopharmaceuticals. It eliminates scale-up issues and enables the entire development cycle, from discovery to manufacturing, to be carried out using one expression process. This helps the biopharmaceutical industry fulfill its promise of improved health and eradication of disease by removing years from drug development, reducing costs by millions, and in some cases ensuring the marketing of new therapeutics from emerging innovators that would have otherwise failed.

The process uses whole cabbage looper caterpillars in an assembly line type procedure, which transforms the caterpillars into near-perfect, self-regulating "mini-bioreactors," with self-optimized cell growth and protein expression. The transformation occurs via infection with a baculovirus. The baculovirus vector delivers the gene encoding the protein of interest to susceptible host cells while providing the control elements needed to express at extraordinarily high levels. The infected cell provides the complex enzymatic machinery for expression and post-translational processing.

Each insect serves as a discrete and predictable unit of production: it sustains exquisite homeostasis; it has a rudimentary immune system, which maintains internal sterility; it respires, which maintains optimal dissolved oxygen for cell growth; and it eats and excretes, which maintains optimal pH and nutrient concentration. And by being more densely packed than any possible concentration in vitro, the insect system optimizes space. Further, using a whole, self-contained organism greatly reduces operator intervention, sterile handling, process controls, and ultimately possible process variables and deviations. The overall process is enabled by the patent-protected use of the orally infectious pre-occluded virus morphotype (POV) used to infect cells via the diet (rather than physical injection).

Mass production of protein in insects is similar to bioreactor-based cell culture, but there are important differences. Both require a vector, growth phase, infection/induction, expression and harvest, and clarification and product separation. However, unlike insect-based production, cell culture processes require sterile seed trains, multiplicity of infection, cell counts, more stringent process controls, and more capital and labor.

Moreover, the inventive manufacturing method requires fewer steps, and most importantly, it vastly improves scale-up, because no process engineering is required. Instead, with each larva treated as a unit, you scale up simply by growing more TRANSPILLAR larvae. In other words, the system completely removes the exorbitant process development and scale-up cycle. Reactor scale up issues, such as oxygen mass transfer, shear, and gas mixing, are obviated, as the system has demonstrated scalability from microgram research quantities to multiple kilograms-commercial scale quantities-easily and linearly, within one to two weeks.

Three commercially valuable components of the invention are:

TRANSPILLAR larvae (Transgenic Insects): A tool for biopharmaceutical manufacturing. A stable line of transgenic-modified caterpillars to be used as a platform that expresses recombinant proteins with human glycosylation without the immunogenicity associated with insect-mediated expression.

PERL SOLUTIONS (Process Out-Licensing): A complete commercial process licensing package, optimized for efficient manufacture of proteins using TRANSPILLAR larvae, and constant regardless of the protein.

C-PERL CONTRACT MANUFACTURING: Complete contract manufacturing expanding over time: from research grade, to final semi-purified bulk for final purification, to final purified bulk API for fill and finish.

TRANSPILLAR larvae decrease development, scale-up, and rework costs. Because failures account for 75% of the $880 million to develop a new drug, TRANSPILLAR larvae should therefore drastically reduce costs, thus often enabling market entry before funding is exhausted.

The benefits to direct customers during each phase of drug development:

1) Discovery: Biotechnology companies, universities, federal laboratories, and research institutions discover proteins that scientists seek to produce in the effort to find those with applications to treat diseases. They need to produce milligram quantities of large numbers of widely varying proteins for testing. As experts in protein expression vectors, they can readily transition to the baculovirus vector required to utilize the TRANSPILLAR larvae. They can use the TRANSPILLAR larvae kit on the bench top without additional capital investment or specialized equipment. The TRANSPILLAR larva is easier to use, does not need sterile conditions, and can produce the needed glycosylation. The customer benefits from ease of use, low capital investment, high yields, and a clear path to development.

2) Development (defining and producing proteins that may become drugs): Development requires larger amounts of proteins, mg to gram quantities, which can be produced in the TRANSPILLAR larva, without the pilot plant, at about half the size and cost. The cycle time is weeks rather than months.

3) Preclinical (early FDA-mandated safety and properties testing): Depending on the type of protein, anywhere from ten to hundreds of grams are needed. These could be produced by contract manufacturing or under license, in-house, with 10,000 to 100,000 insects in one bench top incubator.

4) Clinical trials (three phases): Companies produce enough material for all three trials, often 100s of grams, and with TRANSPILLAR larvae can use essentially the same process.

For example: Company X identifies a promising recombinant protein drug candidate.

The drug has the desired pharmacological characteristic, and Company X is ready to produce milligram quantities for lead optimization and preclinical studies. The preferred method of expression: C-PERL Solutions from Chesapeake PERL (Protein Expression and Recovery Labs). C-PERL's transgenic insects (TRANSPILLAR larvae) produce the same quality product as cell culture, without immunogenicity, and add full mammalian-type glycosylation for full biologic activity and stability in serum.

Company X is now ready to develop the drug. During discovery and development, the R&D staff purchases kits from C-PERL, uses a few dozen TRANSPILLAR larvae on the bench top, and gets the same quality product as the pilot plant. Next, the plant purchases TRANSPILLAR larvae and licenses the completely developed C-PERL Solutions process to manufacture early clinical material—without process development. Further, because the process scales linearly, Company X knows the needed commercial manufacturing capacity early in development. They decide to contract manufacture with C-PERL, and save 5 years in the development phase and millions cutting out technology transfer and scale-up. Their completed Phase I trial data and clear path to commercial manufacturing help oversubscribe a Series B round of financing. C-PERL Solutions manufactures enough drug for Phase II and III trials, and immediately after Phase I Company X begins treating patients under the Investigational New Drug Treatment policy. As they break ground on a new research facility for new lead compounds, the Agency approves the Biologics License Application.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications (including priority document, U.S. provisional application 60/514,741), cited above and below and in the figures are hereby incorporated by reference.

What is claimed is:

1. A transgenic silk worm comprising a plurality of recombinant nucleic acids encoding mammalian glycosylation enzymes and optionally a nucleic acid encoding a heterologous protein of interest to be glycosylated, said silkworm having a genome in which is integrated, in one or more copies:
   a) first construct being pBSII-A3/EYFP-P25/Gal/GnT encoding both a beta 1,4-galactosyltransferase (Gal) and a beta-1,2-N-acetylglucosaminyltransferase II (GnT);
   b) a second construct being pBSII-3xP3/ECFP-P25/ST6/ST3 encoding both alpha-2,6-sialyltransferase (ST6) and alpha 2,3-sialyltransferase (ST3); and
   c) a third construct being pBSII-3xP3/DsRed2-P25/CMP/SAS encoding both a sialic acid synthetase (SAS) and a CMP sialic acid synthetase (CMP),
   wherein each recombinant nucleic acid encoding a glycosylation enzyme is operably linked to an expression control sequence, and wherein expression of said glycosylation enzymes in said transgenic silk worm allows for production of a partially or completely mammalianized glycosylated protein in the silk worm.

2. The silk worm of claim 1 comprising a nucleic acid encoding a heterologous protein of interest.

3. The silk worm of claim 2, wherein said protein is selected from the group consisting of an antibody, a cytokine, erythropoietin, TPA, an interferon, a hormone, insulin, a receptor and an adhesion molecule.

4. The silk worm of claim 3, wherein said protein is erythropoietin.

5. The silk worm of claim 1, wherein said expression control sequence is selected from the group consisting of a P25 promoter of Bombyx mori (P25), a silk fibroin light chain gene promoter, and a silk fibrohexamerin promoter.

6. A transgenic silk worm comprising a plurality of recombinant nucleic acids encoding mammalian glycosylation enzymes and optionally a nucleic acid encoding a heterologous protein of interest to be glycosylated, said silkworm having a genome in which is integrated, in one or more copies, a single construct which expresses six glycosylation enzymes, wherein said construct is pBSII-3xP3/ECFP-P25/6enzymes and encodes ST6, ST3, CMP, SAS, Gal, and Gnt, wherein each recombinant nucleic acid encoding a glycosylation enzyme is operably linked to an expression control sequence, and wherein expression of said glycosylation enzymes in said transgenic silk worm allows for production of a partially or completely mammalianized glycosylated protein in the silk worm.

* * * * *